United States Patent
Nozawa et al.

(10) Patent No.: US 8,044,235 B2
(45) Date of Patent: Oct. 25, 2011

(54) (METH)ACRYLOYL GROUP-CONTAINING AROMATIC ISOCYANATE COMPOUND AND PRODUCTION PROCESS THEREOF

(75) Inventors: Kaneo Nozawa, Aizu-Wakamatsu (JP); Katsutoshi Ohno, Aizu-Wakamatsu (JP); Yotaro Hattori, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 840 days.

(21) Appl. No.: 11/886,487

(22) PCT Filed: Mar. 15, 2006

(86) PCT No.: PCT/JP2006/305620
§ 371 (c)(1),
(2), (4) Date: May 7, 2008

(87) PCT Pub. No.: WO2006/103979
PCT Pub. Date: Oct. 5, 2006

(65) Prior Publication Data
US 2009/0054543 A1    Feb. 26, 2009

Related U.S. Application Data

(60) Provisional application No. 60/663,728, filed on Mar. 22, 2005.

(30) Foreign Application Priority Data

Mar. 15, 2005   (JP) .................................. 2005-073223

(51) Int. Cl.
*C07C 263/10*   (2006.01)
*C07C 263/00*   (2006.01)
(52) U.S. Cl. ........ 560/347; 560/142; 560/144; 560/183; 560/184; 560/188; 560/189; 560/221; 560/223; 560/224; 560/330; 560/336; 560/338; 560/355; 560/358
(58) Field of Classification Search ............. 560/142, 560/144, 183, 184, 188, 189, 221, 223, 224, 560/330, 336, 338, 347, 355, 358
See application file for complete search history.

(56) References Cited

U.S. PATENT DOCUMENTS

| | | | |
|---|---|---|---|
| 2,821,544 A | 1/1958 | Holtschmidt et al. | |
| 5,213,934 A * | 5/1993 | Sacripante et al. | 430/110.2 |
| 6,646,156 B2 * | 11/2003 | Nishioka et al. | 560/222 |
| 7,579,066 B2 * | 8/2009 | Nozawa et al. | 428/209 |
| 7,632,965 B2 * | 12/2009 | Nozawa et al. | 560/213 |
| 2002/0192596 A1 | 12/2002 | Ueda et al. | |

FOREIGN PATENT DOCUMENTS

| | | |
|---|---|---|
| JP | 9-316046 A | 12/1997 |
| JP | 10-316759 A | 12/1998 |
| JP | 2000-86302 A | 3/2000 |
| JP | 2000-204125 A | 7/2000 |
| JP | 2001-200007 A | 7/2001 |
| JP | 2003-12632 A | 1/2003 |
| JP | 2004-14327 A | 1/2004 |
| WO | WO 2005/114331 A1 | 12/2005 |

* cited by examiner

*Primary Examiner* — Rabon Sergent
(74) *Attorney, Agent, or Firm* — Sughrue Mion, PLLC

(57) ABSTRACT

A monomer is provided which is excellent in reactivity, can give high heat resistance and high refractive index, and has two or more polymerizable functional groups with different polymerization properties and an aromatic ring in the molecule. An industrial advantageous process for producing the monomer is also provided. The monomer is an aromatic isocyanate compound containing a (meth)acryloyl group, and is represented by Formula (I):

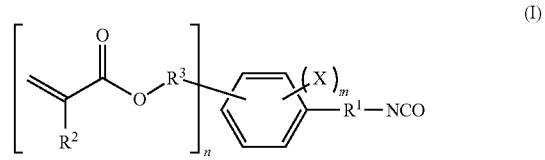

(I)

wherein $R^1$ is a single bond or a linear or branched alkylene group of 1 to 5 carbon atoms, $R^2$ is a hydrogen atom or a methyl group, $R^3$ is a single bond or a linear or branched alkylene group of 1 to 3 carbon atoms, X is independently a halogen atom or an electron-withdrawing group, m is an integer ranging from 0 to 4, n is an integer ranging from 1 to 3, and $1 \leq m+n \leq 5$.

7 Claims, 8 Drawing Sheets

[Fig. 2]
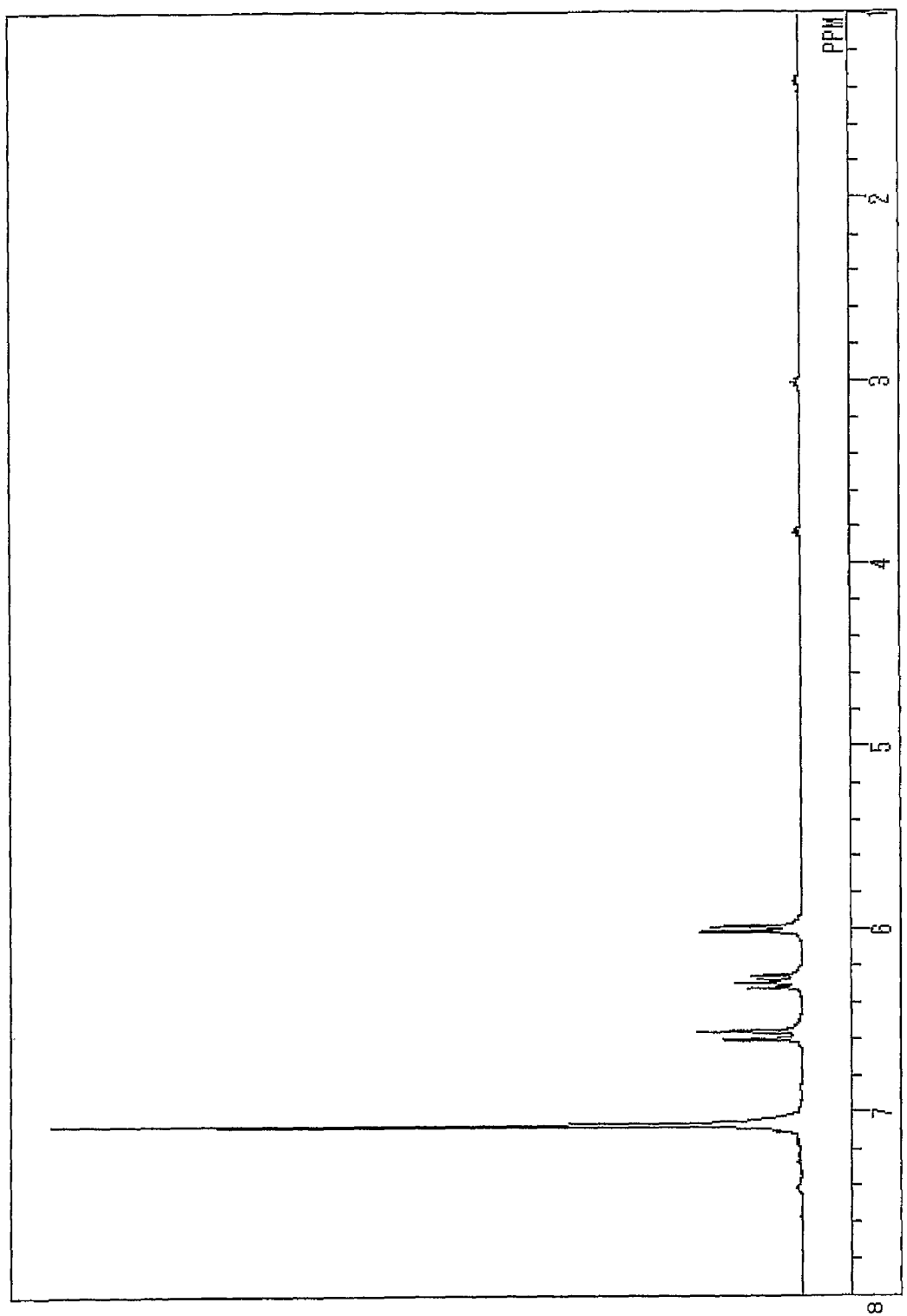

[Fig. 3]
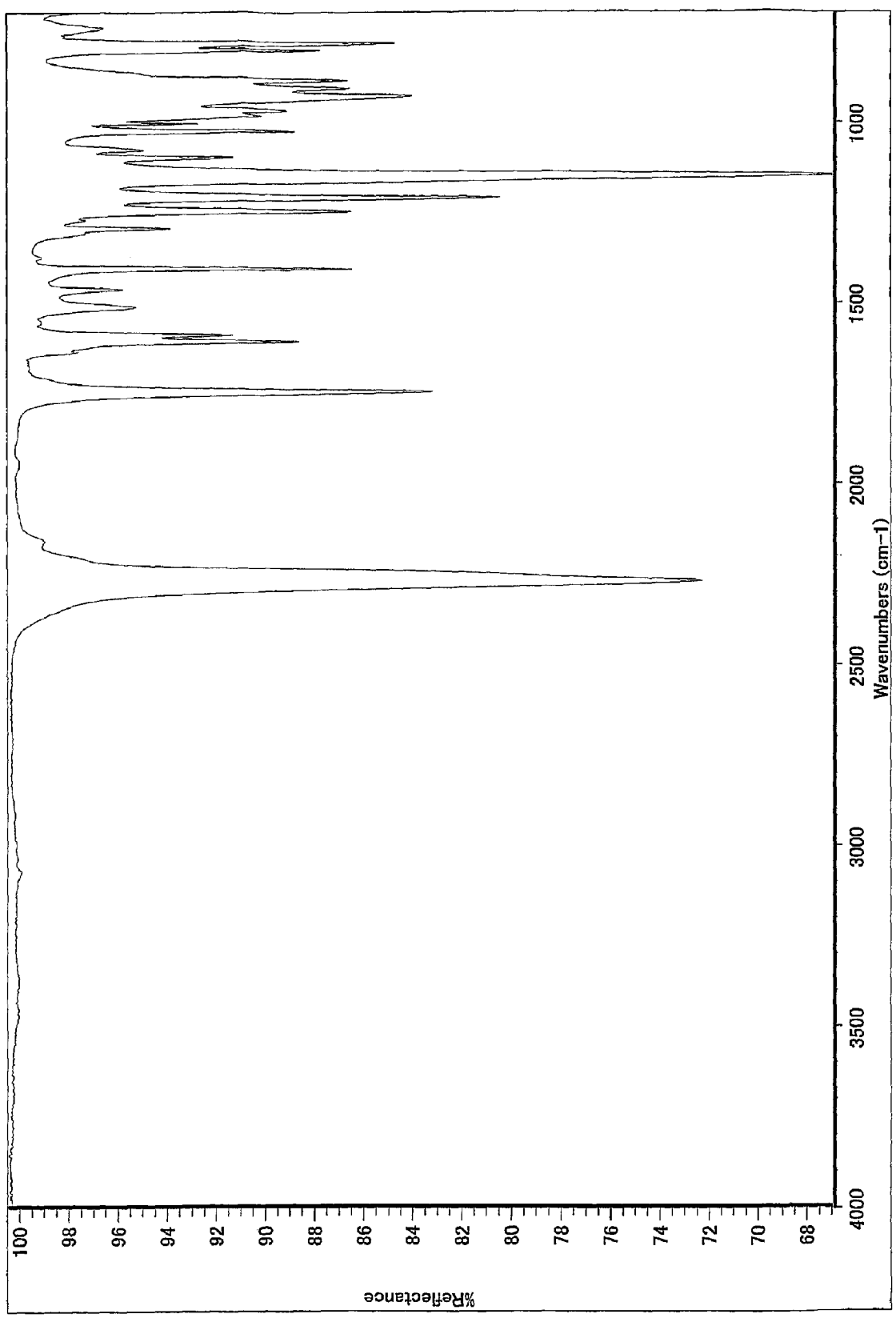

[Fig. 4]
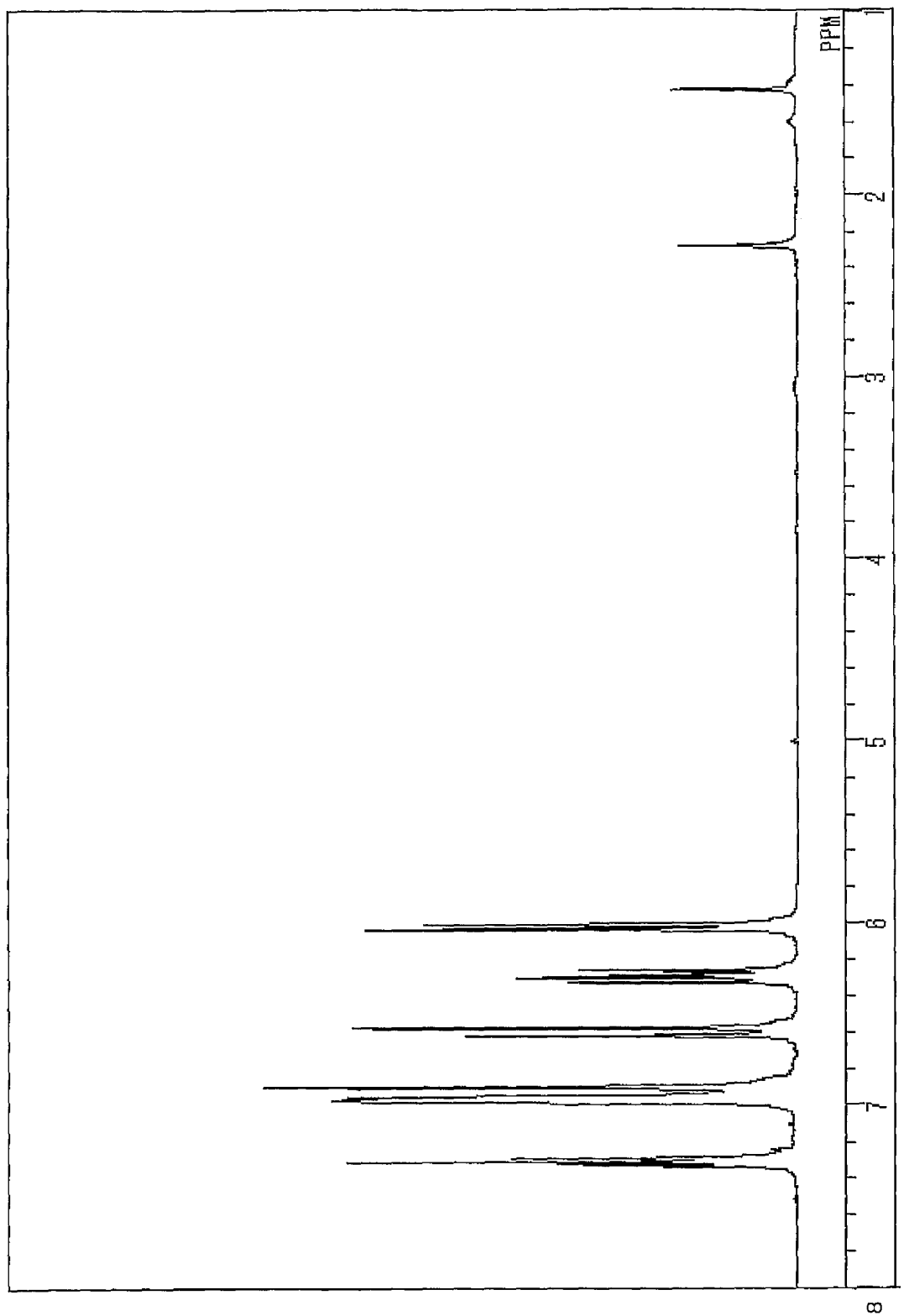

[Fig. 5]
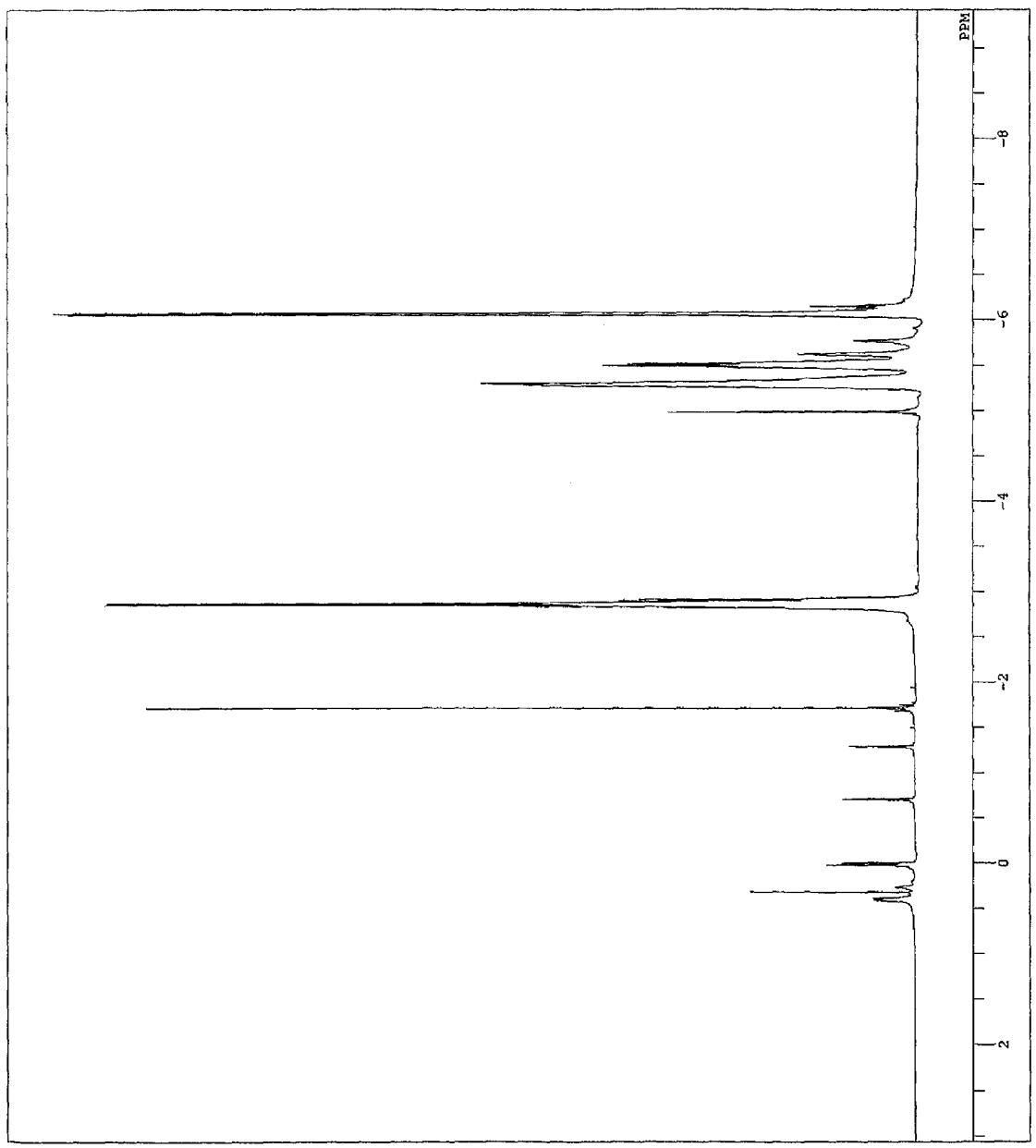

[Fig. 6]
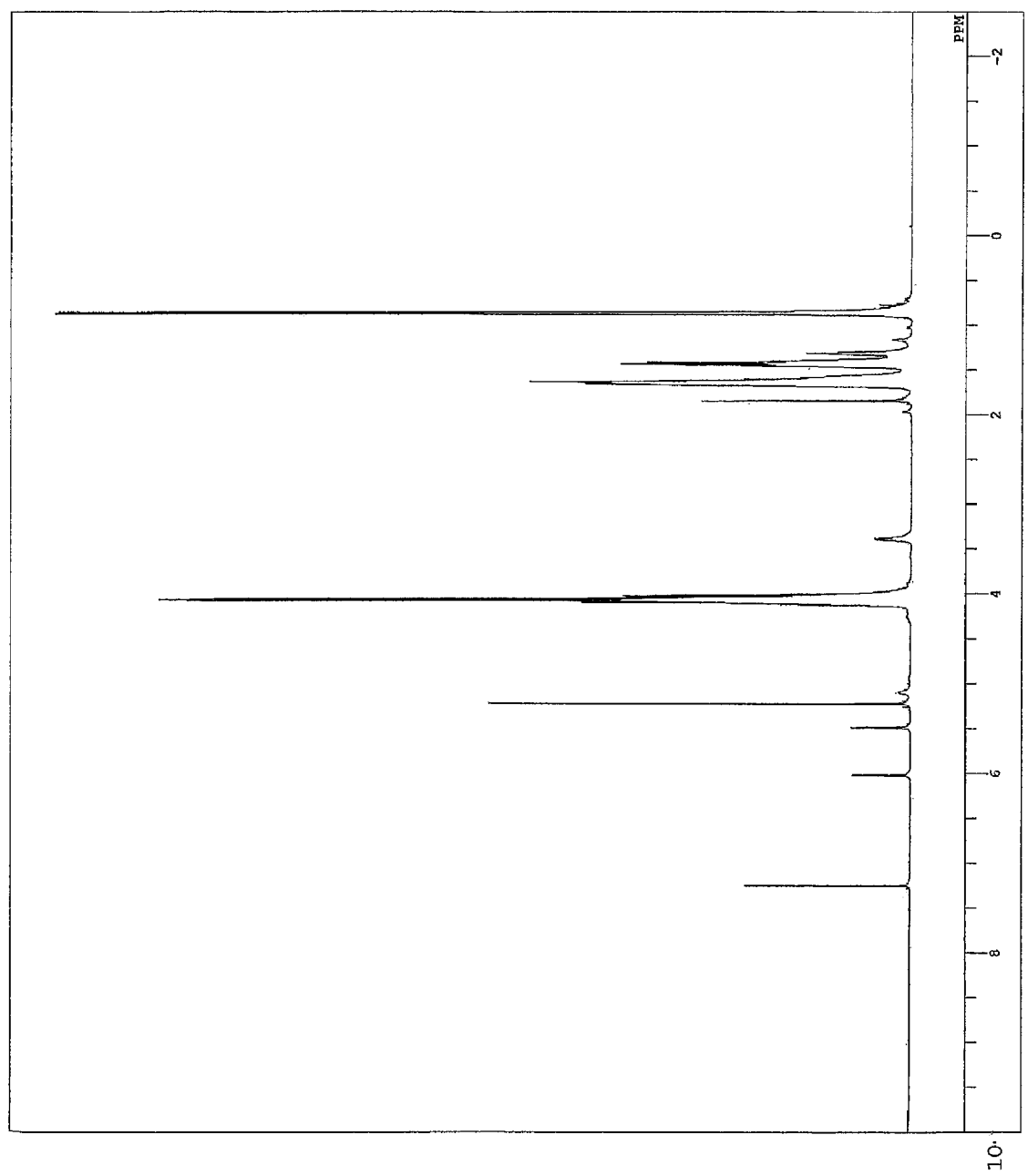

[Fig. 7]
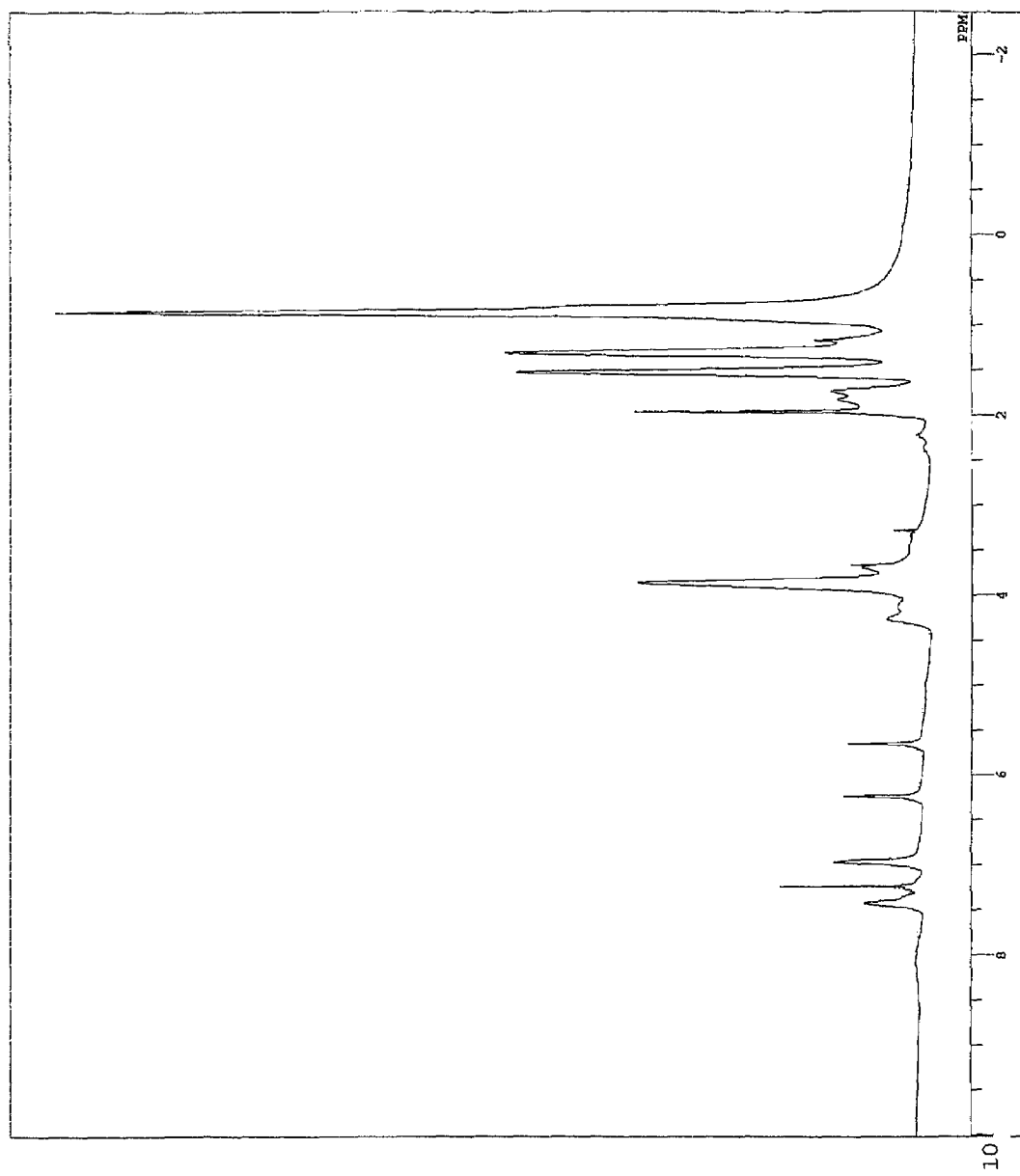

[Fig. 8]
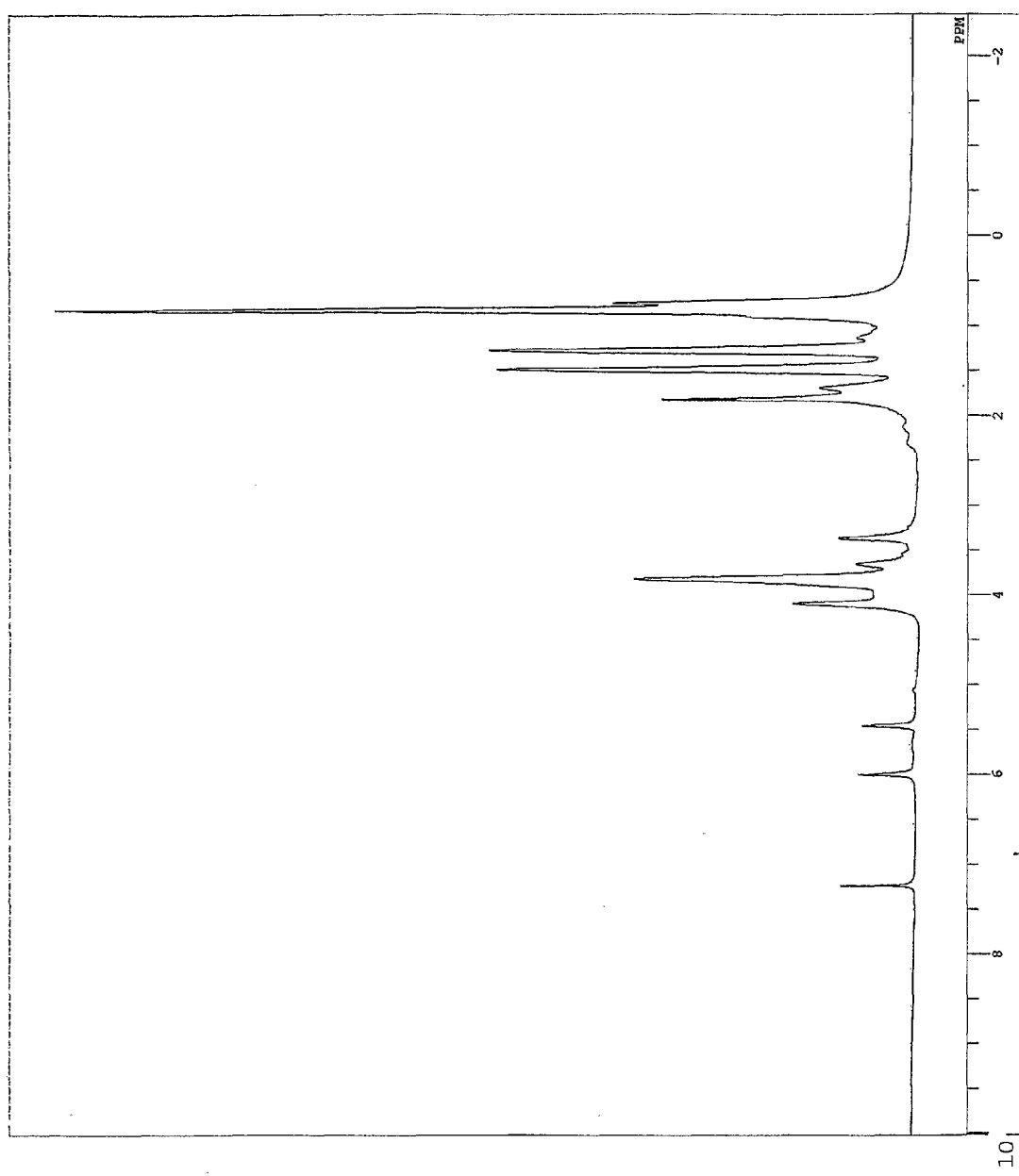

(METH)ACRYLOYL GROUP-CONTAINING AROMATIC ISOCYANATE COMPOUND AND PRODUCTION PROCESS THEREOF

CROSS REFERENCES OF RELATED APPLICATION

This application is an application filed under 35 U.S.C. §111(a) claiming benefit pursuant to 35 U.S.C. §119(e) of the filing date of Provisional Application 60/663,728 filed on Mar. 22, 2005, pursuant to 35 U.S.C. §111(b).

TECHNICAL FIELD

The present invention relates to a novel aromatic isocyanate compound containing a (meth)acryloyl group that has two or more polymerizable functional groups with different polymerization properties and has a sufficient reactivity at the isocyanate group, and a process for producing the compound. The invention is also concerned with a reactive monomer that is obtained from the isocyanate compound and is particularly suited for optical materials, a curable composition containing the monomer, and a cured product of the composition.

BACKGROUND ART

Compounds having an unsaturated group and an isocyanate group in the molecule, with examples including 2-isocyanatoethyl methacrylate (Karenz MOI manufactured by Showa Denko K.K.), are known as monomers having polymerizable functional groups with different polymerization properties in the molecule. Such monomers having in the molecule two functional groups with different polymerization properties, namely, an unsaturated group and an isocyanate group, are compounds that are useful as raw materials for resins in the fields of coating materials, UV curable paints, thermosetting paints, forming materials, adhesives, inks, resists, optical materials, stereolithography resins, printing matrix materials, dental materials, polymer battery materials and the like.

For the production of such compounds, U.S. Pat. No. 2,821,544 (Patent Document 1) discloses a method for preparing an aliphatic compound containing an unsaturated group and an isocyanate group in the molecule. Specifically, the method comprises reacting an unsaturated carboxylic acid chloride with an amino alcohol hydrochloride to synthesize an unsaturated carboxylic acid aminoalkyl ester hydrochloride, and thereafter reacting it with carbonyl chloride to afford an unsaturated carboxylic acid isocyanatoalkyl ester.

The method of Patent Document 1, however, causes problems that the reaction yield is low and the purification entails undue work, because the compound obtained contains much byproducts assumed to be based on the unsaturated group (for example, addition of HCl to the unsaturated group).

For the meanwhile, there have recently been demands for high refractive index and high heat resistance in the optical field and the like, and monomers having an aromatic ring in the molecule have been desired. Such compounds include 3-isopropenyl-α,α-dimethylbenzyl isocyanate compound that has an unsaturated group and an isocyanate group, and an aromatic ring in the molecule, as disclosed in JP-A-2003-12632 (Patent Document 2).

However, the compound of Patent Document 2 has the unsaturated group at the benzyl position, and therefore a cured product of the compound shows low weathering resistance and the reacting rate of the isocyanate group is low.

With respect to the adducts of isocyanate compounds as discussed above, JP-A-2000-086302 (Patent Document 3) discloses a composition including a polyester polyurethane (meth)acrylate oligomer. The oligomer is obtained by urethanization of a polyester polyol obtained by reaction between a specific diol component and a polybasic acid component; a (meth)acrylate having a hydroxyl group; and a polyisocyanate. The document describes that because of containing the oligomer, the composition can show high photocuring properties and high heat resistance even when it includes highly water absorptive acryl monomers such as N-vinylpyrrolidone or when the concentration of urethane groups is increased.

Further, JP-A-2000-204125 (Patent Document 4), JP-A-2001-200007 (Patent Document 5) and JP-A-2004-014327 (Patent Document 6) disclose that urethane acrylate compounds having specific chemical structures provide high heat resistance.

However, according to the description in these documents, the synthesis of urethane compounds entails any of high reaction temperature, long reaction time, and use of environmentally hazardous tin catalyst. These unfavorable factors must be improved.

DISCLOSURE OF INVENTION

It is an object of the present invention to provide a monomer that is excellent in reactivity, can give high heat resistance and high refractive index, and has two or more polymerizable functional groups with different polymerization properties and an aromatic ring in the molecule. It is another object of the invention to provide an industrial advantageous process for producing the monomer. It is a further object of the invention to provide an adduct of the monomer obtained under mild conditions, and a curable composition having high heat resistance and curing properties.

The present inventors studied diligently to solve the aforementioned problems, and have found an aromatic isocyanate compound containing a (meth)acryloyl group that has an aromatic ring in the molecular skeleton and two or more polymerizable functional groups with different polymerization properties in the molecule, and have also found a process for producing the compound. The present invention has been completed based on the findings.

The present invention concerns the following.

[1] An aromatic isocyanate compound containing a (meth)acryloyl group, the compound being represented by Formula (I):

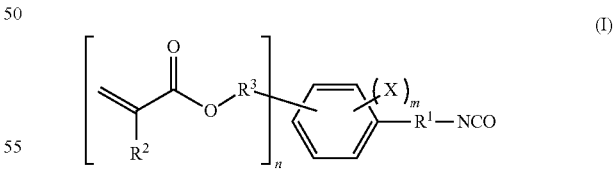

wherein $R^1$ is a single bond or a linear or branched alkylene group of 1 to 5 carbon atoms, $R^2$ is a hydrogen atom or a methyl group, $R^3$ is a single bond or a linear or branched alkylene group of 1 to 3 carbon atoms, X is independently a halogen atom or an electron-withdrawing group, m is an integer ranging from 0 to 4, n is an integer ranging from 1 to 3, and $1 \leq m+n \leq 5$.

[2] The aromatic isocyanate compound containing a (meth)acryloyl group as described in [1], wherein $R^3$ in Formula (I) is a single bond.

[3] The aromatic isocyanate compound containing a (meth)acryloyl group as described in [1] or [2], wherein n in Formula (I) is 1.

[4] The aromatic isocyanate compound containing a (meth)acryloyl group as described in any one of [1] to [3], wherein $R^1$ in Formula (I) is a single bond.

[5] The aromatic isocyanate compound containing a (meth)acryloyl group as described in [1], which is represented by Formula (II):

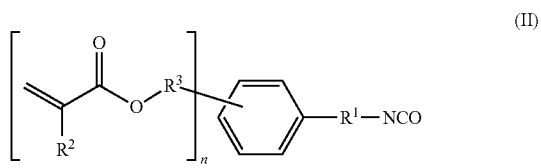

wherein $R^1$, $R^2$, $R^3$ and n are as defined in Formula (I).

[6] The aromatic isocyanate compound containing a (meth)acryloyl group as described in [1], which is represented by Formula (III):

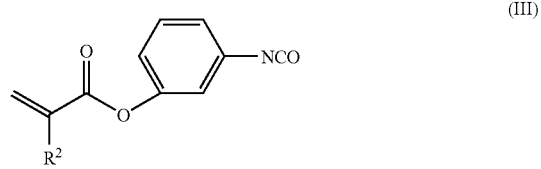

wherein $R^2$ is a hydrogen atom or a methyl group.

[7] The aromatic isocyanate compound containing a (meth)acryloyl group as described in [1], which is represented by Formula (IV):

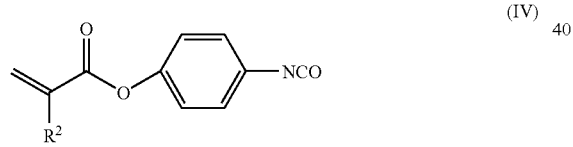

wherein $R^2$ is a hydrogen atom or a methyl group.

[8] The aromatic isocyanate compound containing a (meth)acryloyl group as described in [1], wherein in Formula (I), the substituent group containing the (meth)acryloyloxy group has a substituent constant σ of $-0.2<\sigma<0.8$ relative to the isocyanate-containing group on the aromatic ring.

[9] A process for producing an aromatic isocyanate compound containing a (meth)acryloyl group, the compound being represented by Formula (I):

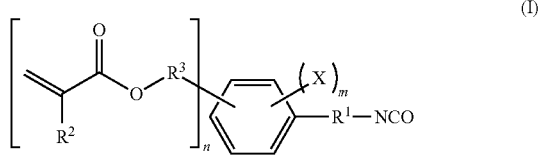

wherein $R^1$ is a single bond or a linear or branched alkylene group of 1 to 5 carbon atoms, $R^2$ is a hydrogen atom or a methyl group, $R^3$ is a single bond or a linear or branched alkylene group of 1 to 3 carbon atoms, X is independently a halogen atom or an electron-withdrawing group, m is an integer ranging from 0 to 4, n is an integer ranging from 1 to 3, and $1\leq m+n\leq 5$, the process comprising the following steps (1) to (4):

(1) a step of obtaining a hydroxyphenylamino mineral acid salt compound from a hydroxyphenylamine compound and a mineral acid, the hydroxyphenylamine compound being represented by Formula (V):

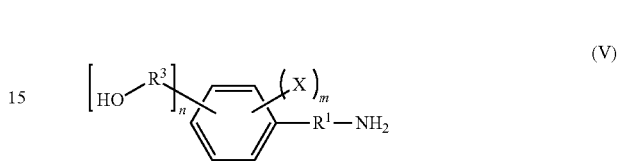

wherein $R^1$, $R^3$, X, m and n are as defined in Formula (I), the hydroxyphenylamino mineral acid salt compound being represented by Formula (VI):

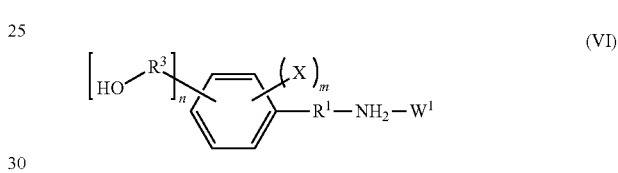

wherein $R^1$, $R^3$, X, m and n are as defined in Formula (I), and $W^1$ is the mineral acid;

(2) a step of obtaining a hydroxyphenyl isocyanate compound from the hydroxyphenylamino mineral acid salt compound obtained in the step (1) and a compound represented by Formula (VII):

wherein $Z^1$ and $Z^2$ are each a fluorine atom, a chlorine atom, a bromine atom, an imidazole, a pyrazole or R'O— wherein R' is an alkyl or alkenyl group of 1 to 6 carbon atoms that may have a branch, or an aryl group that may have a substituent group, the hydroxyphenyl isocyanate compound being represented by Formula (VIII):

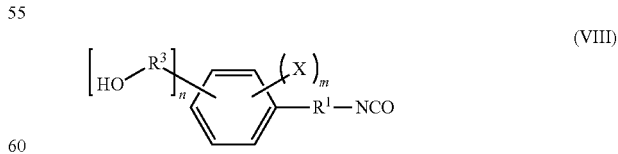

wherein $R^1$, $R^3$, X, m and n are as defined in Formula (I);

(3) a step of obtaining a phenyl ester compound containing an isocyanate group from the hydroxyphenyl isocyanate compound obtained in the step (2) and a compound represented by Formula (IX):

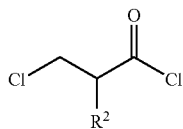

wherein $R^2$ is as defined in Formula (I), the phenyl ester compound containing an isocyanate group being represented by Formula (X):

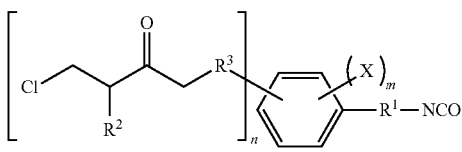

wherein $R^1$ to $R^3$, X, m and n are as defined in Formula (I); and (4) a step of dehydrochlorinating the phenyl ester compound containing an isocyanate group that is obtained in the step (3), in the presence of a basic nitrogen compound.

[10] The process for producing an aromatic isocyanate compound containing a (meth)acryloyl group as described in [9], wherein the mineral acid is at least one acid selected from the group consisting of sulfuric acid, nitric acid, hydrochloric acid, carbonic acid and phosphoric acid.

[11] The process for producing an aromatic isocyanate compound containing a (meth)acryloyl group as described in [9], wherein the reactions in the steps (1) to (4) are performed in solvents.

[12] The process for producing an aromatic isocyanate compound containing a (meth)acryloyl group as described in [11], wherein the solvent used in the step (1) is at least one solvent selected from the group consisting of water, alcohols, esters, ethers, aromatic hydrocarbons, aliphatic hydrocarbons and halogenated hydrocarbons.

[13] The process for producing an aromatic isocyanate compound containing a (meth)acryloyl group as described in [11], wherein the solvent used in the steps (2) to (4) is at least one solvent selected from the group consisting of esters, ethers, aromatic hydrocarbons, aliphatic hydrocarbons and halogenated hydrocarbons.

[14] The process for producing an aromatic isocyanate compound containing a (meth)acryloyl group as described in [12], wherein the step (2) is performed after the solvent used in the step (1) is distilled away.

[15] The process for producing an aromatic isocyanate compound containing a (meth)acryloyl group as described in [9], wherein the basic nitrogen compound used in the step (4) is triethylamine.

[16] The process for producing an aromatic isocyanate compound containing a (meth)acryloyl group as described in [9], wherein a basic nitrogen compound is added as catalyst in the step (3).

[17] A process for producing an aromatic isocyanate compound containing a (meth)acryloyl group, the compound being represented by Formula (I):

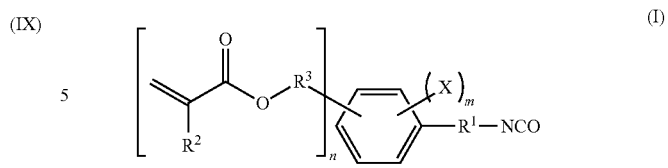

wherein $R^1$ is a single bond or a linear or branched alkylene group of 1 to 5 carbon atoms, $R^2$ is a hydrogen atom or a methyl group, $R^3$ is a single bond or a linear or branched alkylene group of 1 to 3 carbon atoms, X is independently a halogen atom or an electron-withdrawing group, m is an integer ranging from 0 to 4, n is an integer ranging from 1 to 3, and $1 \leq m+n \leq 5$, the process comprising the following steps (1') to (3'):

(1') a step of obtaining a hydroxyphenylamino mineral acid salt compound from a hydroxyphenylamine compound and a mineral acid, the hydroxyphenylamine compound being represented by Formula (V):

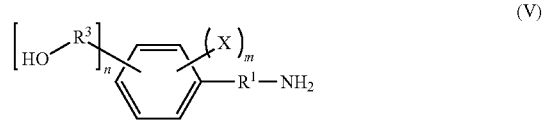

wherein $R^1$, $R^3$, X, m and n are as defined in Formula (I), the hydroxyphenylamino mineral acid salt compound being represented by Formula (VI):

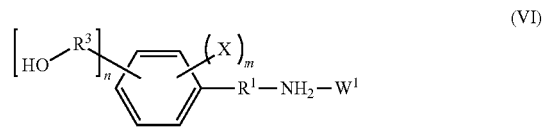

wherein $R^1$, $R^3$, X, m and n are as defined in Formula (I), and $W^1$ is the mineral acid;

(2') a step of obtaining a hydroxyphenyl isocyanate compound from the hydroxyphenylamino mineral acid salt compound obtained in the step (1') and a compound represented by Formula (VII):

wherein $Z^1$ and $Z^2$ are each a fluorine atom, a chlorine atom, a bromine atom, an imidazole, a pyrazole or R'O— wherein R' is an alkyl or alkenyl group of 1 to 6 carbon atoms that may have a branch, or an aryl group that may have a substituent group, the hydroxyphenyl isocyanate compound being represented by Formula (VIII):

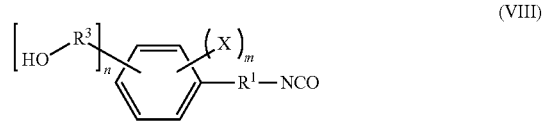

wherein $R^1$, $R^3$, X, m and n are as defined in Formula (I); and (3') a step of reacting the hydroxyphenyl isocyanate compound obtained in the step (2') with a compound represented by Formula (XI):

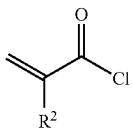
(XI)

wherein R² is as defined in Formula (I).

[18] The process for producing an aromatic isocyanate compound containing a (meth)acryloyl group as described in [17], wherein the mineral acid is at least one acid selected from the group consisting of sulfuric acid, nitric acid, hydrochloric acid, carbonic acid and phosphoric acid.

[19] The process for producing an aromatic isocyanate compound containing a (meth)acryloyl group as described in [17], wherein the reactions in the steps (1') to (3') are performed in solvents.

[20] The process for producing an aromatic isocyanate compound containing a (meth)acryloyl group as described in [19], wherein the solvent used in the step (1') is at least one solvent selected from the group consisting of water, alcohols, esters, ethers, aromatic hydrocarbons, aliphatic hydrocarbons and halogenated hydrocarbons.

[21] The process for producing an aromatic isocyanate compound containing a (meth)acryloyl group as described in [19], wherein the solvent used in the steps (2') and (3') is at least one solvent selected from the group consisting of esters, ethers, aromatic hydrocarbons, aliphatic hydrocarbons and halogenated hydrocarbons.

[22] The process for producing an aromatic isocyanate compound containing a (meth)acryloyl group as described in [20], wherein the step (2') is performed after the solvent used in the step (1') is distilled away.

[23] The process for producing an aromatic isocyanate compound containing a (meth)acryloyl group as described in [17], wherein a basic nitrogen compound is added as catalyst in the step (3').

[24] A urethane compound containing a (meth)acryloyl group, the compound being represented by Formula (XII):

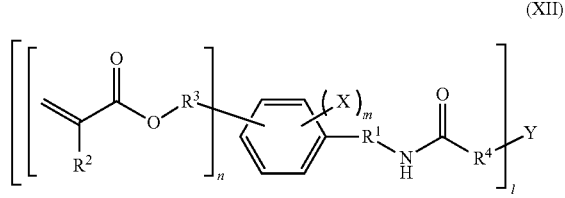
(XII)

wherein R¹ is a single bond or a linear or branched alkylene group of 1 to 5 carbon atoms, R² is a hydrogen atom or a methyl group, R³ is a single bond or a linear or branched alkylene group of 1 to 3 carbon atoms, R⁴ is an ether group, a thioether group or an NH group, X is independently a halogen atom or an electron-withdrawing group, Y is an aliphatic group, an aromatic ring-containing group, a heterocyclic ring-containing group, a polycarbonate residue, a polyurethane residue, a polyester residue or a residue of polyhydroxy compound having repeating units, l is an integer ranging from 1 to 50, m is an integer ranging from 0 to 4, n is an integer ranging from 1 to 3, and $1 \leq m+n \leq 5$.

[25] The urethane compound containing a (meth)acryloyl group as described in [24], wherein R³ in Formula (XII) is a single bond.

[26] The urethane compound containing a (meth)acryloyl group as described in [24] or [25], wherein n in Formula (XII) is 1.

[27] The urethane compound containing a (meth)acryloyl group as described in any one of [24] to [26], wherein R¹ in Formula (XII) is a single bond.

[28] The urethane compound containing a (meth)acryloyl group as described in [24], which is represented by Formula (XIII):

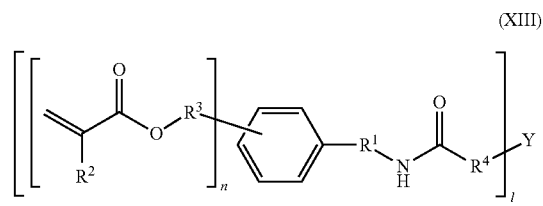
(XIII)

wherein R¹, R², R³, R⁴, Y, l and n are as defined in Formula (XII).

[29] The urethane compound containing a (meth)acryloyl group as described in [24], which is represented by Formula (XIV):

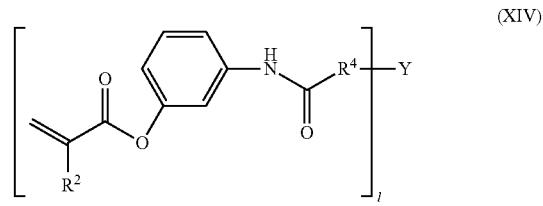
(XIV)

wherein R², R⁴, Y and l are as defined in Formula (XIII).

[30] The urethane compound containing a (meth)acryloyl group as described in [24], which is represented by Formula (XV):

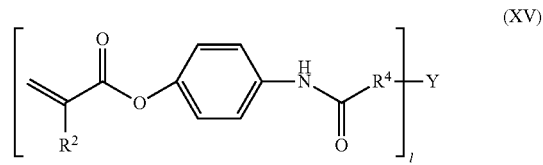
(XV)

wherein R², R⁴, Y and l are as defined in Formula (XIII).

[31] A reactive monomer represented by Formula (XII) of [24] wherein the substituent group containing the acryloyloxy group has a substituent constant σ of 0<σ<0.8 relative to the urethane linkage-containing group on the aromatic ring.

[32] A reactive monomer represented by Formula (XII) of [24] wherein R⁴ is an ether group, Y is an alkyl group, a xylylene group, a fluorine-containing group or a norbornane group, and l is 1 or 2.

[33] The reactive monomer as described in [32], wherein Y in Formula (XII) is a group represented by $-(CH_2)_p(CF_2)_qF$ (wherein p is an integer ranging from 0 to 2, q is an integer ranging from 0 to 8, and p and q cannot be 0 at the same time).

[34] A reactive monomer represented by Formula (XII) of [24] wherein R⁴ is an ether group, Y is a group having a fluorene skeleton, and n is 2.

[35] A reactive monomer represented by Formula (XII) of [24] wherein $R^4$ is an NH group, Y is an alkyl group, a xylylene group, a fluorine-containing group or a norbornane group, and n is 1 or 2.

[36] The reactive monomer as described in [35], wherein in Formula (XII), Y is a group represented by —$CH_2(CF_2)_8F$, or —$R^4$—Y is a residue of 2,6-difluoroaniline.

[37] A reactive monomer represented by Formula (XII) of [24] wherein $R^4$ is a thioether group, and Y is a linear or branched, saturated aliphatic group or a phenyl group.

[38] A process for producing a reactive monomer as described in any one of [31] to [37], the process comprising reacting the aromatic isocyanate compound containing a (meth)acryloyl group of Formula (I) of [1], with a compound containing a functional group with active hydrogen.

[39] The urethane compound containing a (meth)acryloyl group as described in [24], wherein in Formula (XII):

Y has a structure comprising a polycarbonate skeleton which has a molecular weight of 500 to 5000, and includes at least one residue selected from the group consisting of:
aliphatic dihydric alcohol residue in which the alkylene group is trimethylene group;
aliphatic dihydric alcohol residue in which the alkylene group is tetramethylene group;
aliphatic dihydric alcohol residue in which the alkylene group is pentamethylene group;
aliphatic dihydric alcohol residue in which the alkylene group is hexamethylene group;
aliphatic dihydric alcohol residue in which the alkylene group is heptamethylene group;
aliphatic dihydric alcohol residue in which the alkylene group is octamethylene group; and
residues of 1,9-nonanediol, 1,10-decanediol, 1,11-undecanediol, 1,12-dodecanediol, 1,20-eicosanediol and 1,4-cyclohexanedimethanol; and
n is 2.

[40] The urethane compound containing a (meth)acryloyl group as described in [39], wherein
the aliphatic dihydric alcohol residue in which the alkylene group is trimethylene group is selected from 2-methyl-1,3-propanediol, 1,3-butanediol, 2,4-heptanediol, 2,2-diethyl-1,3-propanediol, 2-methyl-2-propyl-1,3-propanediol, 2-ethyl-1,3-hexanediol, 2-methyl-2,4-pentanediol, 2,2,4-trimethyl-1,3-pentanediol and 2-butyl-2-ethyl-1,3-propanediol residues;
the aliphatic dihydric alcohol residue in which the alkylene group is tetramethylene group is 1,4-butanediol residue;
the aliphatic dihydric alcohol residues in which the alkylene group is pentamethylene group is selected from 1,5-pentanediol, 3-methyl-1,5-pentanediol and 1,5-hexanediol residues;
the aliphatic dihydric alcohol residues in which the alkylene group is hexamethylene group is selected from 1,6-hexanediol and 2-ethyl-1,6-hexanediol residues;
the aliphatic dihydric alcohol residues in which the alkylene group is heptamethylene group is 1,7-heptanediol residue;
the aliphatic dihydric alcohol residues in which the alkylene group is octamethylene group is selected from 1,8-octanediol and 2-methyl-1,8-octanediol residues.

[41] A process for producing a reactive (meth)acrylate polymer, comprising reacting the aromatic isocyanate compound containing a (meth)acryloyl group of Formula (I) of [1], with the urethane compound containing a (meth)acryloyl group of [39].

[42] A process for producing a reactive (meth)acrylate polymer, comprising reacting the aromatic isocyanate compound containing a (meth)acryloyl group of Formula (I) of [1], with a polymer compound that includes repeating units containing a functional group with active hydrogen.

[43] The process for producing a reactive (meth)acrylate polymer as described in [42], wherein the polymer compound is a polyhydroxy compound including repeating units.

[44] The process for producing a reactive (meth)acrylate polymer as described in [41] or [42], wherein the aromatic isocyanate compound containing a (meth)acryloyl group is represented by Formula (III) of [6] or Formula (IV) of [7].

[45] The process for producing a reactive (meth)acrylate polymer as described in [43], wherein the polyhydroxy compound including repeating units is a polyester polyol compound, a polycarbonate polyol compound, a polyether polyol compound, a polyurethane polyol compound, a hydroxyalkyl (meth)acrylate homopolymer or copolymer, or an epoxy (meth)acrylate compound.

[46] The process for producing a reactive (meth)acrylate polymer as described in [43], wherein the polyhydroxy compound including repeating units contains a carboxyl group.

[47] A reactive (meth)acrylate polymer produced by reacting the aromatic isocyanate compound containing a (meth)acryloyl group of Formula (I) of [1], with a polymer compound that includes repeating units containing a functional group with active hydrogen.

[48] The reactive (meth)acrylate polymer as described in [47], wherein the polymer compound is a polyhydroxy compound including repeating units.

[49] The reactive (meth)acrylate polymer as described in [47] or [48], wherein the aromatic isocyanate compound containing a (meth)acryloyl group is represented by Formula (III) of [6].

[50] The reactive (meth)acrylate polymer as described in [47] or [48], wherein the aromatic isocyanate compound containing a (meth)acryloyl group is represented by Formula (IV) of [7].

[51] The reactive (meth)acrylate polymer as described in [48], wherein the polyhydroxy compound including repeating units is a polyester polyol compound, a polycarbonate polyol compound, a polyether polyol compound, a polyurethane polyol compound, a hydroxyalkyl (meth)acrylate homopolymer or copolymer, or an epoxy (meth)acrylate compound.

[52] The reactive (meth)acrylate polymer as described in [48], wherein the polyhydroxy compound including repeating units contains a carboxyl group.

[53] The reactive (meth)acrylate polymer as described in [48], wherein the polyhydroxy compound is an acrylic copolymer of molecular weight of 5,000 to 50,000, the copolymer including repeating units represented by Formula (XVI) or (XVII):

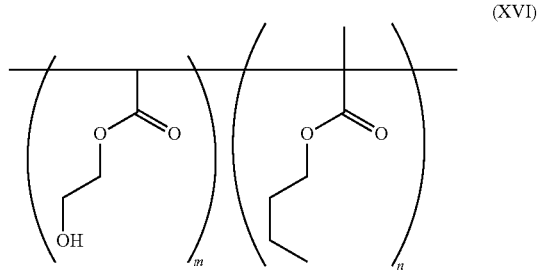

-continued

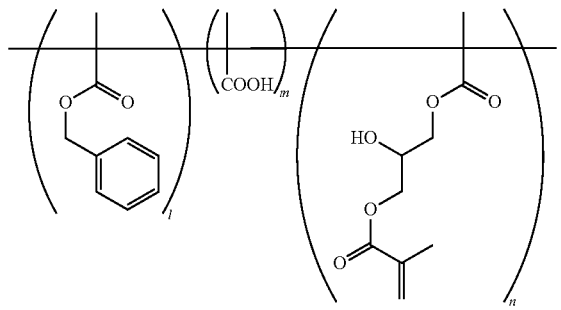

(XVII)

[54] A curable composition comprising the reactive monomer as described in any one of [31] to [37] and a polymerization initiator.

[55] A cured product produced by curing the curable composition as described in [54].

[56] The curable composition as described in [54], wherein the polymerization initiator is a photopolymerization initiator.

[57] The curable composition as described in [56], further comprising an ethylenically unsaturated monomer.

[58] A curable composition comprising:
(A) 10 to 40% by mass of the reactive (meth)acrylate polymer as described in any one of [47] to [53];
(B) 25 to 60% by mass of a pigment;
(D) 2 to 25% by mass of a photopolymerization initiator;
(F) 5 to 20% by mass of an ethylenically unsaturated monomer; and
(G) an organic solvent.

[59] A curable composition comprising:
(A) 10 to 40% by mass of the reactive (meth)acrylate polymer as described in any one of [47] to [53];
(B) 25 to 60% by mass of a pigment;
(D) 2 to 20% by mass of a photopolymerization initiator;
(F) 5 to 20% by mass of an ethylenically unsaturated monomer;
(G) an organic solvent; and
(H) 2 to 20% by mass of a polyfunctional thiol.

[60] The curable composition as described in any one of [57] to [59], which is used for forming a color filter.

[61] The curable composition as described in [58] or [59], wherein the pigment (B) is carbon black.

[62] A curable composition comprising:
(A) the reactive (meth)acrylate polymer as described in any one of [47] to [53];
(C) a thermosetting polymer;
(D) a photopolymerization initiator; and
(E) a thermal polymerization catalyst.

[63] The curable composition as described in [62], which is used as a solder resist.

[64] An insulating protective film produced from the curable composition as described in [62].

[65] A printed wiring board including the insulating protective film as described in [64].

The aromatic isocyanate compound containing a (meth)acryloyl group according to the present invention is excellent in reactivity and can give functions such as high heat resistance and high refractive index. Therefore, the compound can find use as raw material monomer in widespread fields including coating materials, UV curable paints, thermosetting paints, forming materials, adhesives, inks, resists, optical materials, stereolithography resins, printing matrix materials, dental materials and polymer battery materials.

The aromatic isocyanate compound containing a (meth)acryloyl group according to the present invention, can yield the reactive monomer of the invention under mild conditions in a short time. This synthesis does not involve any catalyst for accelerating the reaction, and therefore the monomer can produce a cured product having reduced coloration and impurities.

BRIEF DESCRIPTION OF THE DRAWINGS

FIG. 2 is an NMR chart of the compound obtained in Example 1;

FIG. 3 is an IR chart of the compound obtained in Example 2;

FIG. 4 is an NMR chart of the compound obtained in Example 2;

FIG. 5 is an NMR chart of the compound obtained in Production Example 1;

FIG. 6 is an NMR chart of the compound obtained in Comparative Production Example 1;

FIG. 7 is an NMR chart of the compound obtained in Production Example 3; and

FIG. 8 is an NMR chart of the compound obtained in Comparative Production Example 2.

BEST MODE FOR CARRYING OUT THE INVENTION

Figure 1:
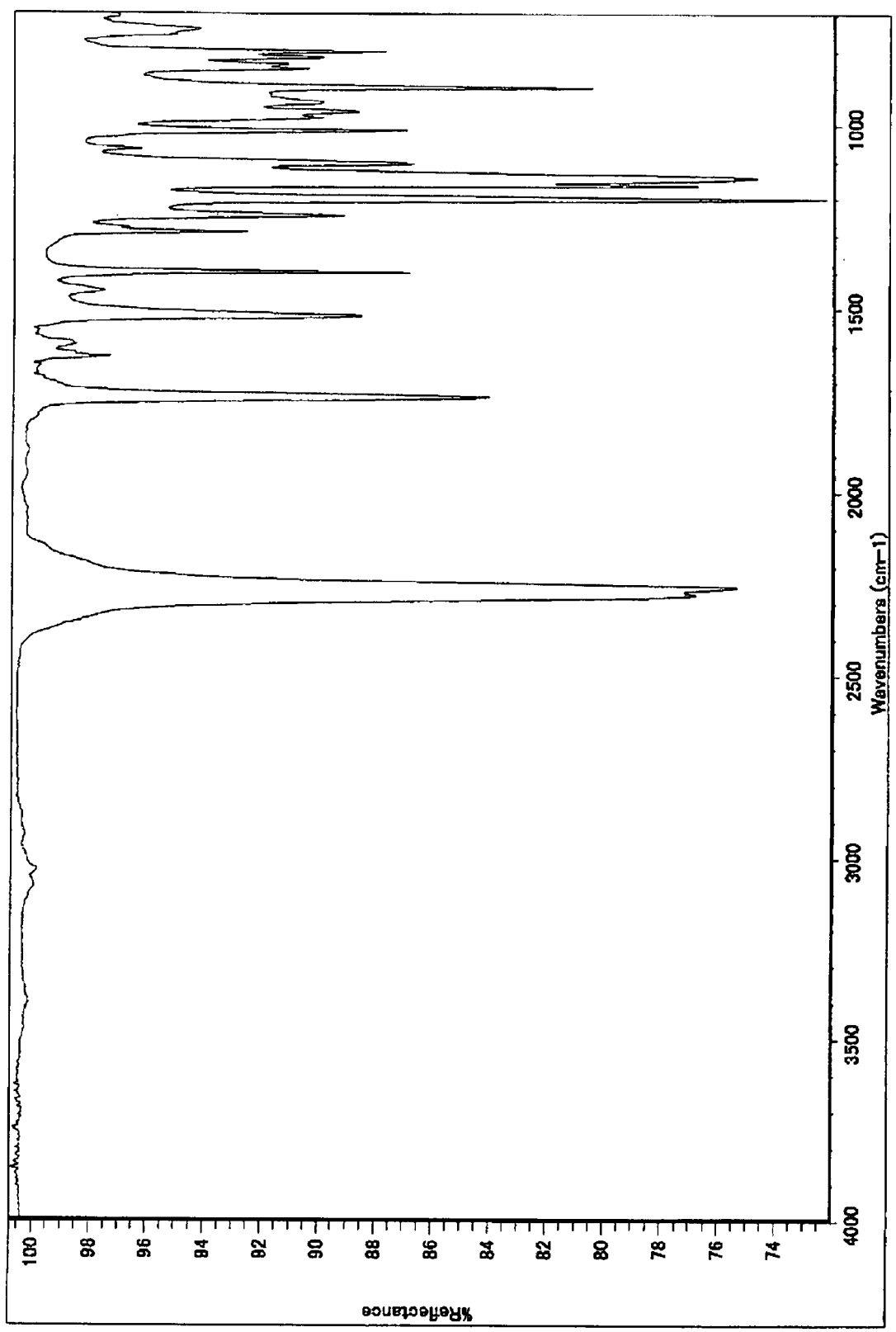
FIG. 1 is an IR chart of the compound obtained in Example 1.

The aromatic isocyanate compound containing a (meth)acryloyl group, the process for production thereof, and synthesis of the urethane compound according to the present invention will be hereinafter described in detail. Herein, the general formulae will comprehend all possible stereoisomers such as cis-stereoisomers and trans-stereoisomers.

(i) Aromatic Isocyanate Compound Containing (meth)acryloyl Group

The aromatic isocyanate compound containing a (meth)acryloyl group of the present invention is represented by Formula (I):

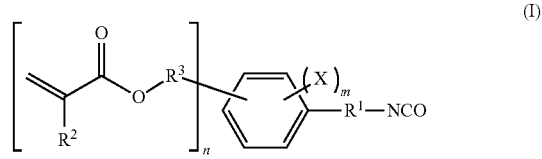

(I)

In Formula (I), $R^1$ is a single bond or a linear or branched alkylene group of 1 to 5 carbon atoms, with specific examples including single bond, methylene group, ethylene group, propylene group, isopropylene group, butylene group and isobutylene group. Of these, single bond, methylene group and ethylene group are preferred. $R^2$ is a hydrogen atom or a methyl group. $R^3$ is a single bond or a linear or branched alkylene group of 1 to 3 carbon atoms, with specific examples including single bond, methylene group, ethylene group, propylene group and isopropylene group. Of these, single bond, methylene group and ethylene group are preferred. X is independently a halogen atom or an electron-withdrawing group. The letter m is an integer ranging from 0 to 4; the letter n is an integer ranging from 1 to 3, and is particularly preferably 1; and $1 \leq m+n \leq 5$.

Preferred examples of the compounds represented by Formula (I) (hereinafter the compounds (I)) include those having Formulae (III) and (IV).

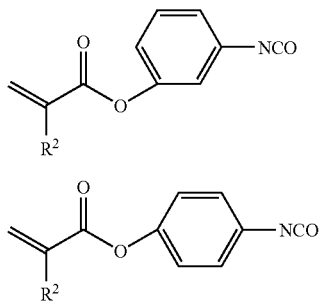

(III)

(IV)

Specific preferred examples of the compounds (I) include 4-acryloyloxyphenyl isocyanate, 3-acryloyloxyphenyl isocyanate, 2-acryloyloxyphenyl isocyanate, 4-methacryloyloxyphenyl isocyanate, 3-(acryloyloxymethyl)phenyl isocyanate, 2-(acryloyloxymethyl)phenyl isocyanate, 3,5-bis(methacryloyloxyethyl)phenyl isocyanate and 2,4-bis(acryloyloxy)phenyl isocyanate.

In particular, the substituent group containing a reactive (meth)acryloyl group is preferably an electron-withdrawing group that has a substituent constant σ of 0<σ<0.8 relative to the isocyanate-containing group on the aromatic ring. Specific examples include methacryloyloxy group and acryloyloxy group.

In the isocyanate compounds described above as preferred examples of the compounds (I), the reactivity of the isocyanate group can be controlled by the substituent constant of the substituent group containing a reactive (meth)acryloyl group. Consequently, the addition reaction can take place at room temperature or without a catalyst.

(ii) First Process for Producing Aromatic Isocyanate Compound Containing (meth)acryloyl Group The first process for producing the compounds (I) includes:

(1) a step of synthesizing a hydroxyphenylamino mineral acid salt compound represented by Formula (VI) (hereinafter the compound (VI)) from a hydroxyphenylamine compound represented by Formula (V) (hereinafter the compound (V)) and a mineral acid;

(2) a step of synthesizing a hydroxyphenyl isocyanate compound represented by Formula (VIII) (hereinafter the compound (VIII)) from the compound (VI) obtained in the step (1) and a compound represented by Formula (VII);

(3) a step of synthesizing a phenyl ester compound containing an isocyanate group that is represented by Formula (X) (hereinafter the compound (X)) from the compound (VIII) obtained in the step (2) and a compound represented by Formula (IX); and (4) a step of dehydrochlorinating the compound (X) obtained in the step (3) in the presence of a basic nitrogen compound.

The process will be hereinafter described step by step.

<Step (1)>

The step (1) is illustrated in the reaction scheme below in which the compound (VI) represented by Formula (VI) is synthesized from the compound (V) represented by Formula (V) and the mineral acid ($W^1$).

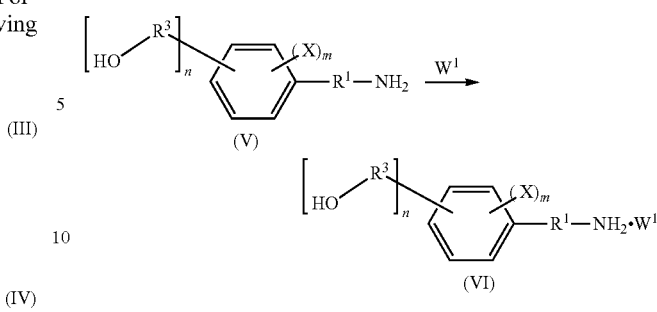

(V)

(VI)

Examples of the compounds (V) used as raw material in the step (1) include 4-aminophenol, 3-aminophenol, 2-aminophenol, 4-(aminomethyl)phenol, 3-(aminomethyl)phenol, 2-(aminomethyl)phenol, 4-(1-aminoethyl)phenol, 3-(1-aminoethyl)phenol, 2-(1-aminoethyl)phenol, 4-(1-aminopropyl)phenol, 3-(1-aminopropyl)phenol, 2-(1-aminopropyl)phenol, 4-(2-aminopropyl)phenol, 3-(2-aminopropyl)phenol, 2-(2-aminopropyl)phenol, 4-(3-aminopropyl)phenol, 3-(3-aminopropyl)phenol, 2-(3-aminopropyl)phenol, 4-(1-amino-1-methylethyl)phenol, 3-(1-amino-1-methylethyl)phenol, 2-(1-amino-1-methylethyl)phenol, 4-(2-amino-1-methylethyl)phenol, 3-(2-amino-1-methylethyl)phenol, 2-(2-amino-1-methylethyl)phenol, 4-amino-1,2-benzenediol, 3-amino-1,2-benzenediol, 5-amino-1,3-benzenediol, 4-amino-1,3-benzenediol, 2-amino-1,3-benzenediol, 3-amino-1,4-benzenediol, 2-amino-1,4-benzenediol, 5-aminomethyl-1,3-benzenediol, 4-aminomethyl-1,3-benzenediol, 2-aminomethyl-1,3-benzenediol, 4-aminomethyl-1,2-benzenediol, 3-aminomethyl-1,2-benzenediol, 4-(2-aminoethyl)-1,2-benzenediol, 3-(2-aminoethyl)-1,2-benzenediol, 5-(2-aminoethyl)-1,3-benzenediol, 4-(2-aminoethyl)-1,3-benzenediol, 2-(2-aminoethyl)-1,3-benzenediol, 3-(3-aminopropyl)-1,4-benzenediol, 2-(3-aminopropyl)-1,4-benzenediol, 4-(3-aminopropyl)-1,2-benzenediol, 3-(3-aminopropyl)-1,2-benzenediol, 3-(2-aminopropyl)-1,4-benzenediol, 2-(2-aminopropyl)-1,4-benzenediol, 4-(2-aminopropyl)-1,2-benzenediol, 3-(2-aminopropyl)-1,2-benzenediol, 4-(2-amino-1-methylethyl)-1,2-benzenediol, 3-(2-amino-1-methylethyl)-1,2-benzenediol, 2-amino-1,3,5-benzenetriol, 6-amino-1,2,4-benzenetriol, 5-amino-1,2,4-benzenetriol, 3-amino-1,2,4-benzenetriol, 5-amino-1,2,3-benzenetriol, 4-amino-1,2,3-benzenetriol, 5-aminomethyl-1,2,3-benzenetriol, 4-aminomethyl-1,2,3-benzenetriol, (4-aminophenyl)methanol, (3-aminophenyl)methanol, (2-aminophenyl)methanol, 2-(4-aminophenyl)ethanol, 2-(3-aminophenyl)ethanol, 2-(2-aminophenyl)ethanol, 2-[4-(aminomethyl)phenyl]ethanol, 2-[2-(aminomethyl)phenyl]ethanol and 3,5-bis(1-aminophenyl)ethanol.

Of these, 5-amino-1,3-benzenediol, 3,5-bis(1-aminophenyl)ethanol, 2-[4-(aminomethyl)phenyl]ethanol, 4-(aminomethyl)phenol, 2-(aminomethyl)phenol, 4-aminophenol, 3-aminophenol and 2-aminophenol are preferred.

The mineral acid used in the step (1) is not particularly limited and examples thereof include sulfuric acid, nitric acid, hydrochloric acid, carbonic acid and phosphoric acid. Hydrochloric acid, carbonic acid and dry hydrogen chloride gas are preferred, and hydrochloric acid and dry hydrogen chloride gas are more preferred, and dry hydrogen chloride gas is particularly preferred.

The amount of the mineral acid is not particularly limited and may vary depending on the type of the amine compound (V). The amount is generally in the range of 1 to 5 mol, preferably 1 to 1.2 mol per mol of the amine compound (V). When the mineral acid is used in amounts less than the above range, the yield can be lowered and the subsequent steps can be adversary affected. The amount exceeding the above range is unfavorable because it causes a burden on waste liquid treatment and dischargers and the like.

The step (1) may use a solvent which is not particularly limited and may vary depending on the type of the amine compound (V). The use of solvent is generally preferable, but may be omitted when the raw-material amine compound (V) and/or amino mineral acid salt compound (VI) formed is liquid or molten.

Examples of the solvents include water; alcohols such as methanol, ethanol, n-propanol, isopropanol, n-butanol and n-hexanol; esters such as methyl acetate, ethyl acetate, propyl acetate, isopropyl acetate and butyl acetate; chain ethers such as diethyl ether, dipropyl ether and dibutyl ether; cyclic ethers such as dioxane, dioxolane and tetrahydrofuran; aromatic hydrocarbons such as toluene, xylene, ethylbenzene, mesitylene and cumene; aliphatic hydrocarbons such as propane, hexane, heptane and cyclohexane; and halogenated hydrocarbons such as methylene chloride, 1,2-dichloroethane and 1,2-dichlorobenzene. Of these, dioxane, dioxolane, tetrahydrofuran and ethyl acetate are preferable because of their high polarity.

The solvent may generally be used in an amount of 2 to 100 parts by mass, preferably 3 to 20 parts by mass, more preferably 5 to 10 parts by mass per part by mass of the amine compound (V). When the amount of the solvent is less than the above range, it is unfavorable because controlling the reaction can be difficult. When the amount of the solvent exceeds the above range, it is unfavorable because the reaction rate can be remarkably lowered.

The reaction temperature is not particularly limited and may vary depending on the type of the compound used. For example, the reaction temperature is generally in the range of 0 to 150° C., preferably 15 to 120° C., more preferably 30 to 100° C. When the reaction temperature is below the above range, it is unfavorable because the reaction rate can be lowered. When the reaction temperature exceeds the above range, it is unfavorable because the salt formed can be thermally decomposed.

The amino mineral acid salt compound (VI) obtained in the step (1) may be directly subjected to the subsequent step (2). However, it is preferable that the compound be subjected to the step (2) after the solvent is distilled away. It is also appropriate to purify the compound by conventional methods such as extraction and recrystallization before the step (2).

<Step (2)>

The step (2) is illustrated in the reaction scheme below in which the compound (VIII) represented by Formula (VIII) is synthesized from the compound (VI) obtained in the step (1) and the compound (VII) represented by Formula (VII).

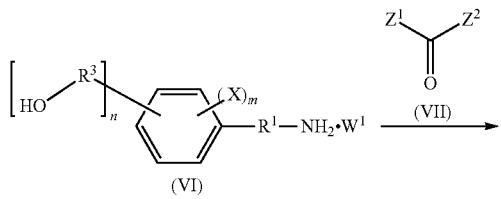

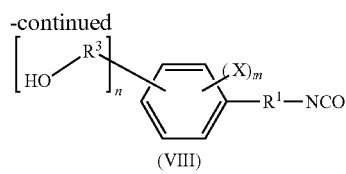

Referring to Formula (VII), preferred examples of $Z^1$ and $Z^2$ include fluorine atom; chlorine atom; bromine atom; alkyloxy groups such as methoxy group, ethoxy group, propoxy group, isopropoxy group, butoxy group, pentoxy group, hexoxy group and cyclohexoxy group; alkenyloxy groups such as vinyloxy group and allyloxy group; aryloxy groups such as phenyloxy group, tolyloxy group, xylyloxy group, biphenyloxy group, naphthyloxy group, anthryloxy group and phenanthryloxy group; imidazoles such as imidazole, 2-imidazoline, 3-imidazoline, 4-imidazoline, imidazolidine, imidazolidone, ethyleneurea and ethylenethiourea; and pyrazoles such as pyrazole, 1-pyrazoline, 2-pyrazoline, 3-pyrazoline and pyrazolidone. Of these, chlorine and fluorine atoms are more preferable, and chlorine atom is particularly preferable.

Dimers and trimers of the above compound are also employable. The dimers are made up of two molecules of the compound (VII) and, when $Z^1$ and $Z^2$ are chlorine atoms, are represented by Formula (XVIII).

The trimers are made up of three molecules of the compound (VII) and, when $Z^1$ and $Z^2$ are chlorine atoms, are represented by Formula (XIX).

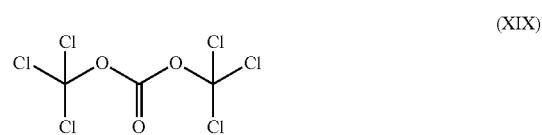

The amount of the compound (VII) to the amino mineral acid salt compound (VI) is not particularly limited and may vary depending on the type of the compound (VII) used. Theoretically, the reaction between the compound (VI) and the compound (VII) takes place in a 1:1 molar ratio. However, the use of an excess of the compound (VII) is preferable for the reaction to proceed smoothly. For example, the amount of the compound (VII) is generally in the range of 1 to 10 mol, preferably 1 to 5 mol per mol of the compound (VI). When the compound (VII) is used in amounts less than the above range, unreacted amino mineral acid salt compound (VI) increases to possibly lower the yield and increase impurities. Although the amount exceeding the above range does not adversary affect the reaction, such excessive use is unfavorable because it requires dischargers and the like and can increase load on the environment.

The step (2) may use a solvent which is not particularly limited and may vary depending on the type of the raw-material amine compound (V). The use of solvent is generally preferable, but may be omitted when the amino mineral acid salt compound (VI) is liquid or molten. Examples of the solvents include the organic solvents described in the step (1) except water and the alcohols.

The solvent may generally be used in an amount of 1.5 to 200 parts by mass, preferably 2 to 20 parts by mass per part by mass of the amino mineral acid salt compound (VI). When the amount of the solvent is less than the above range, it is unfavorable because the reaction often cannot proceed smoothly. When the amount of solvent exceeds the above range, it is unfavorable because it increases the amount of solvent to be disposed and can increase load on the environment.

The reaction temperature in the step (2) may vary depending on the type of the compounds used. For example, the reaction temperature is generally in the range of 30 to 150° C., preferably 50 to 120° C. When the reaction temperature is below the above range, it is unfavorable because the reaction rate can be lowered. When the reaction temperature exceeds the above range, it is unfavorable because the mineral acid salt is liberated from the amino mineral acid salt compound (VI) to possibly cause formation of impurities.

The resultant isocyanate compound (VIII) may be subjected to reaction in the subsequent step (3) directly or after purified by methods such as extraction, recrystallization and distillation.

<Step (3)>

The step (3) is illustrated in the reaction scheme below in which the compound (X) represented by Formula (X) is synthesized from the compound (VIII) obtained in the step (2) and the compound (IX) represented by Formula (IX).

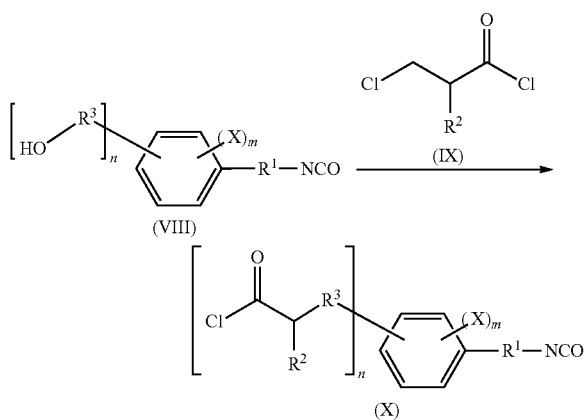

The compound (IX), for example 3-chloropropionic acid chloride, may be obtained by reacting methacrylic acid with phosgene in dimethylformamide as solvent. These compounds may be commercially available as reagents.

The amount of the compound (IX) to the isocyanate compound (VIII) may vary depending on the type of the compound used. For example, the amount is generally in the range of 1 to 10 mol, preferably 3 to 6 mol per mol of the compound (VIII). When the amount of the compound (IX) is less than the above range, it is unfavorable because the yield can be lowered and impurities can be increased. When the amount of the compound (IX) exceeds the above range, it is unfavorable because it increases wastes and can increase load on the environment.

In the step (3), the use of solvent is generally preferable, but may be omitted when the isocyanate compound is liquid or molten. Examples of the solvents include those mentioned in the step (2).

The solvent may be used in an amount 1.5 to 200 times, preferably 2 to 20 times the mass of the isocyanate compound (VIII). When the amount of the solvent is less than the above range, it is unfavorable because the reaction often cannot proceed smoothly. When the amount of the solvent exceeds the above range, it is unfavorable because it increases the amount of solvent to be disposed and can increase load on the environment.

The reaction temperature in the step (3) may vary depending on the type of the compound used. For example, the reaction temperature is generally in the range of 30 to 150° C., preferably 50 to 120° C. When the reaction temperature is below the above range, it is unfavorable because the reaction rate can be lowered. When the reaction temperature exceeds the above range, it is unfavorable because impurities can increase and unsaturated bonds can polymerize.

In the step (3), a basic nitrogen compound is preferably added as catalyst for accelerating the reaction. The basic nitrogen compound refers to a nitrogen-containing compound showing basicity for dehydrochlorination.

Examples of the basic nitrogen compounds include trimethylamine, triethylamine, tripropylamine, dimethylethylamine, dimethylisopropylamine, diethylmethylamine, dimethylbutylamine, dimethylhexylamine, diisopropylethylamine, dimethylcyclohexylamine, tetramethyldiaminomethane, dimethylbenzylamine, tetramethylethylenediamine, tetramethyl-1,4-diaminobutane, tetramethyl-1,3-diaminobutane, tetramethyl-1,6-diaminohexane, pentamethyldiethylenetriamine, 1-methylpiperidine, 1-ethylpiperidine, N,N-methylpiperazine, N-methylmorpholine, 1,8-diazabicyclo[5.4.0]-7-undecene (DBU), 1,5-diazabicyclo[4.3.0]-5-noene (DBN), 2,4-diazabicyclo[2.2.2]octane (DABCO), N,N-dimethylaniline, N,N-diethylaniline and ion-exchange resins containing tertiary nitrogen.

The basic nitrogen compounds may be used singly or in combination of two or more kinds. Of the above basic nitrogen compounds, trimethylamine, triethylamine and tripropylamine are preferred.

The resultant phenyl ester compound containing an isocyanate group (X) may be subjected to reaction in the subsequent step (4) directly or after purified by methods such as extraction, recrystallization and distillation.

<Step (4)>

The step (4) is illustrated in the reaction scheme below in which the aromatic isocyanate compound containing a (meth)acryloyl group that is represented by Formula (I) is synthesized by dehydrochlorinating the compound (X) obtained in the step (3) in the presence of the basic nitrogen compound.

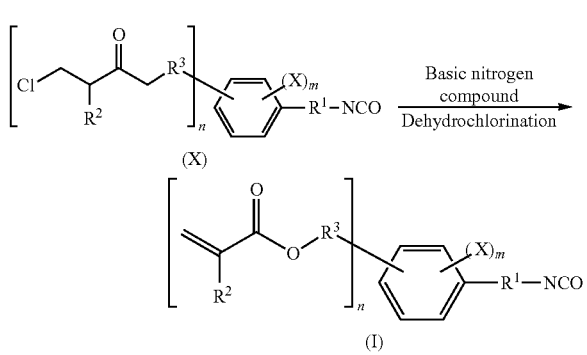

Examples of the basic nitrogen compounds used in the step (4) include those mentioned in the step (3). The basic nitrogen compound used in the step (4) preferably contains a tertiary nitrogen atom, and more preferably contains a tertiary nitrogen atom that has at least one group other than an aromatic ring group, for example alkyl group. Also preferably, not more than one aromatic ring group is bonded to the tertiary nitrogen atom. Specific preferable examples include trimethylamine, triethylamine and tripropylamine, with triethylamine being particularly preferable.

The amount of the basic nitrogen compound may vary depending on the type of the compound used. Desirably, the amount of the basic nitrogen compound is determined depending on the concentration of alkali decomposable chlorine in the reaction liquid after the step (3). Specifically, the basic nitrogen compound is used in an amount of 0.5 to 10 mol, preferably 0.8 to 5.0 mol, more preferably 0.9 to 2.0 mol per mol of the alkali decomposable chlorine.

When the amount of the basic nitrogen compound is less than the above range, it is unfavorable because the yield can be lowered. When the amount of the basic nitrogen compound exceeds the above range, it is unfavorable because the stability of the compound formed can be deteriorated and the cost is increased.

The content of the alkali decomposable chlorine is determined by potentiometric titration in which the reaction liquid obtained in the step (3) is diluted with a methanol/water mixed solvent, and an aqueous sodium hydroxide solution is added to the diluted liquid followed by heating, and the resultant liquid is potentiometrically titrated with a silver nitrate solution. Details will be described later.

The step (4) may use a solvent which is not particularly limited and may vary depending on the type of the compound used. The use of solvent is generally preferable, but may be omitted when the ester compound (X) is liquid or molten. Examples of the solvents include those mentioned in the step (2).

The solvent may be used in an amount of 1.5 to 200 parts by mass, preferably 2 to 20 parts by mass per part by mass of the ester compound (X). When the amount of the solvent is less than the above range, it is unfavorable because the reaction often cannot proceed smoothly and the removal of the salt formed is difficult. When the amount of the solvent exceeds the above range, it is unfavorable because it increases the amount of solvent to be disposed and can increase load on the environment.

The reaction temperature in the step (4) is not particularly limited and may vary depending on the type of the compound used. For example, the reaction temperature is in the range of 0 to 150° C., preferably 20 to 100° C. When the reaction temperature is below the above range, it is unfavorable because the reaction rate can be lowered. When the reaction temperature exceeds the above range, it is unfavorable because the unsaturated bonds formed by the dehydrochlorination can polymerize.

The inventive compound (I) obtained in the step (4) may be purified by conventional methods such as filtration, extraction, recrystallization and distillation.

(iii) Second Process for Producing Aromatic Isocyanate Compound Containing (meth)acryloyl Group Next, the second process for producing an aromatic isocyanate compound containing a (meth)acryloyl group will be described. The second process includes:

(1') a step which is the same as the step (1) of the first process;

(2') a step which is the same as the step (2) of the first process; and (3') a step of synthesizing the aromatic isocyanate compound containing a (meth)acryloyl group that is represented by Formula (I) from the isocyanate compound (VIII) obtained in the step (2') and a compound represented by Formula (XI) (hereinafter the compound (XI)).

The step (3') is illustrated in the reaction scheme below:

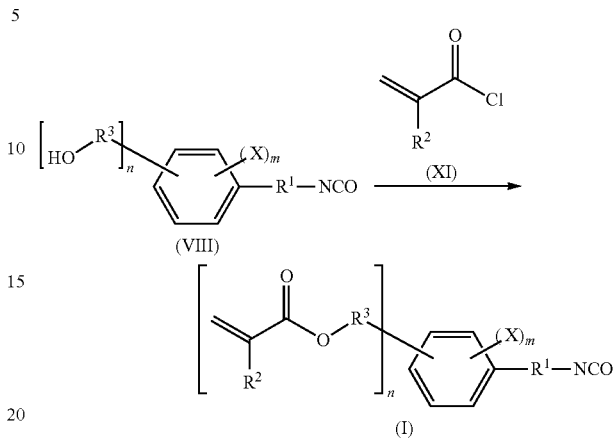

The compound (XI) used in the step (3'), for example methacrylic acid chloride, may be obtained by reacting methacrylic acid with phosgene in dimethylformamide as solvent. The compound (XI) is also available from reagent manufacturers.

The amount of the compound (XI) may vary depending on the type of the compound used. For example, the amount is in the range of 1 to 10 mol, preferably 3 to 6 mol per mol of the hydroxyphenyl isocyanate compound (VIII). When the amount of the compound (XI) is less than the above range, it is unfavorable because the yield can be lowered and impurities can be increased. When the amount of the compound (XI) exceeds the above range, it is unfavorable because it can increase wastes and consequent disposal costs.

The step (3') may use a solvent which is not particularly limited and may vary depending on the type of the compound used. The use of solvent is generally preferable, but may be omitted when the isocyanate compound (VIII) is liquid or molten. Examples of the solvents include those mentioned in the step (2) of the first process.

The solvent may be used in an amount of 1.5 to 200 parts by mass, preferably 2 to 20 parts by mass per part by mass of the compound (VIII). When the amount of the solvent is less than the above range, it is unfavorable because the reaction often cannot proceed smoothly. When the amount of the solvent exceeds the above range, it is unfavorable because it increases the amount of solvent to be disposed and can increase load on the environment.

The reaction temperature in the step (3') may vary depending on the type of the compound used. For example, the reaction temperature is generally in the range of 30 to 150° C., preferably 50 to 120° C. When the reaction temperature is below the above range, it is unfavorable because the reaction rate can be lowered. When the reaction temperature exceeds the above range, it is unfavorable because impurities can increase and unsaturated bonds can polymerize.

The inventive compound (I) obtained in the step (3') may be purified by conventional methods such as filtration, extraction, recrystallization and distillation.

The aromatic isocyanate compound containing a (meth)acryloyl group according to the present invention has functions of giving high heat resistance and high refractive index and is therefore useful in the field of functional resins. As an example, copolymerization of the compound (I) of the present invention with (meth)acrylates such as methyl methacrylate and methyl acrylate or vinyl group-containing compounds such as vinyl ether and styrene can produce functional polymer materials with functions such as high heat resistance and high refractive index.

(iv) Reactive Monomer

Reaction of the compound (I) with monomers, oligomers or polymers containing active hydrogen such as hydroxyl group, amino group or carboxyl group can produce materials corresponding to the monomers, oligomers or polymers and provided with functions such as high heat resistance and high refractive index.

Moreover, the use of the compound (I) provides possibility of a composition that is capable of high curing rate and has functions such as high heat resistance and high refractive index.

For example, the reaction between the compound (I) and a compound having a hydroxyl group in the molecule gives a urethane compound containing a (meth)acryloyl group, which is represented by Formula (XII):

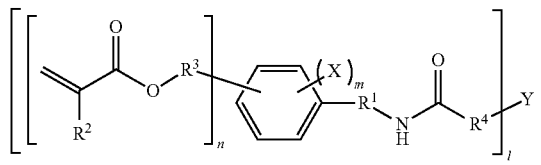

(XII)

In Formula (XII), $R^1$ is a single bond or a linear or branched alkylene group of 1 to 5 carbon atoms, with specific examples including single bond, methylene group, ethylene group, propylene group, isopropylene group, butylene group and isobutylene group. Of these, single bond, methylene group and ethylene group are preferred.

$R^2$ is a hydrogen atom or a methyl group.

$R^3$ is a single bond or a linear or branched alkylene group of 1 to 3 carbon atoms, with specific examples including single bond, methylene group, ethylene group, propylene group and isopropylene group. Of these, single bond, methylene group and ethylene group are preferred.

$R^4$ is an ether group, a thioether group or an NH group.

X is independently a halogen atom or an electron-withdrawing group.

The letter l is an integer ranging from 1 to 50; the letter m is an integer ranging from 0 to 4; the letter n is an integer ranging from 1 to 3, and is particularly preferably 1; and $1 \leq m+n \leq 5$.

Y is an aliphatic group, an aromatic ring-containing group, a heterocyclic ring-containing group, a polycarbonate residue, a polyurethane residue, a polyester residue or a residue of polyhydroxy compound having repeating units.

The aliphatic groups Y are made up of linear, branched or cyclic carbon chains and have 1 to 4 substitutable positions. Specific examples thereof include linear or branched alkyl groups, linear or branched alkylene groups, and cycloalkyl groups.

The aliphatic groups Y may have substituent groups, with specific examples including alkyl groups such as ethyl group, n-butyl group, n-hexyl group, $-CH_2CH_2(CF_2)_8F$ and $-CH_2CF_2CF_2CF_2CF_2CF_2CF_2CH_3$; and cycloalkyl groups such as cyclohexyl group, cycloalkenyl groups and norbornyl group.

The aromatic groups Y have 1 to 4 substitutable positions. Specific examples thereof include phenyl group, xylylene group, bisphenol group and fluorene group.

The heterocyclic groups Y have 1 to 4 substitutable positions. Specific examples thereof include pyridyl group, thienyl group, furyl group, piperidyl group, imidazolyl group and quinolyl group.

Particularly preferred examples of the compounds having Formula (XII) include those represented by Formula (XIV) and (XV):

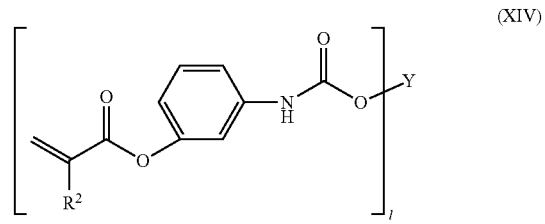

(XIV)

wherein $R^2$, Y and l are as defined in Formula (XII);

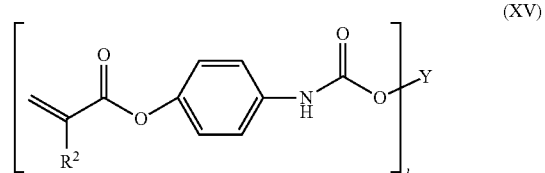

(XV)

wherein $R^2$, Y and l are as defined in Formula (XII).

The reactive monomers may be cured by light or heat that causes radical polymerization or cationic polymerization at the ethylenically unsaturated groups.

Specific examples of preferred reactive monomers in the present invention will be described for a case where $R^4$ represents an ether group, a case where $R^4$ represents a thioether group, and a case where $R^4$ represents an NH group.

<Reactive Monomer in Which $R^4$ Represents an Ether Group>

In the reactive monomer in the first example, in Formula (XII), $R^4$ represents an ether group, Y represents a fluorine-containing group, and l=1. Specific examples of the fluorine-containing group having one position which can be substituted include fluoroalkyl groups. The fluoroalkyl group preferably has 1 to 20 carbon atoms, more preferably 1 to 10 carbon atoms, and may have a straight-chain structure (for example, $-CF_2CF_3$, $-CH_2(CF_2)_4H$, $-CH_2(CF_2)_8CF_3$, $-CH_2CH_2(CF_2)_4H$, or $-CH_2CH_2(CF_2)_8F$), a branched-chain structure (for example, $-CH(CF_3)_2$, $-CH_2CF(CF_3)_2$, $-CH(CH_3)CF_2CF_3$, or $-CH(CH_3)(CF_2)_5CF_2H$), an alicyclic structure (preferably a five-membered or six-membered ring, for example, a perfluorocyclohexyl group, a perfluorocyclopentyl group, or an alkyl group substituted by the above group), or may have an ether bond. Specific examples of ether bond-containing fluoroalkyl groups include $-CH_2OCH_2CF_2CF_3$, $-CH_2CH_2OCH_2C_4F_8H$, $-CH_2CH_2OCH_2CH_2C_8F_{17}$, and $-CH_2CH_2OCF_2CF_2OCF_2CF_2H$.

A plurality of fluoroalkyl groups described above may be contained in the same molecule.

An example of preferred Y in Formula (XII) is a group represented by $-(CH_2)_p(CF_2)_qF$ wherein p is an integer of 0 to 2 and q is an integer of 0 to 8, provided that p and q do not simultaneously represent 0.

The fluorine content is preferably not less than 30% by weight based on the total amount of the reactive monomer, more preferably not less than 40% by weight, still more preferably not less than 50% by weight. When the fluorine content is excessively low, the refractive index value is increased. In this case, in some cases, properties as a low-refractive index material cannot be provided when the product is used as an antireflection film or a cladding material. For example, when the fluorine content is less than 40% by weight, in some cases, the refractive index is not less than 1.45. This refractive index is not appropriate as a low-refractive index material. The fluorine content based on the total amount of the composition can be brought to not less than 50% by weight by preparing the composition using the reactive monomer as one component.

In the reactive monomer in the second example, in Formula (XII), $R^4$ represents an ether group, Y represents a fluorine-containing group, and l=2. The fluorine-containing group having two positions which can be substituted is preferably a group obtained from a fluorine-containing diol. Specific examples of fluorine-containing diols include perfluoroalkyl diols such as 2,2,3,3,4,4-hexafluoro-1,5-pentanediol, 2,2,3,3,4,4,5,5-octafluoro-1,6-hexanediol, and 2,2,3,3,4,4,5,5,6,6,7,7-dodecafluoro-1,8-octanediol; perfluoroalkylene glycols such as perfluorotriethylene glycol and perfluorotetraethylene glycol; polyperfluoroalkylene ether diols such as α-(1,1-difluoro-2-hydroxyethyl)-ω-(2,2-difluoroethanol)poly(oxy-1,1,2,2-tetrafluoroethylene), α-(1,1-difluoro-2-hydroxyethyl)-ω-(2,2-difluoroethanol)poly(oxy-difluoromethylene), and α-(1,1-difluoro-2-hydroxyethyl)-ω-(2,2-difluoroethanol)poly(oxy-difluoromethylene) (oxy-1,1,2,2-tetrafluoroethylene); ring-opened diols of fluoroalkyl epoxides such as 3-perfluorobutyl-1,2-epoxypropane, 3-perfluorooctyl-1,2-epoxypropane, and 3-perfluorobutyl-1,2-epoxypropane; and 2,2-bis(4-hydroxycyclohexyl)hexafluoropropane. A group obtained from a diol comprising an alkylene oxide such as ethylene oxide or propylene oxide added to the fluorine-containing diol may also be used.

The preferred fluorine content range based on the total amount of the reactive monomer is the same as described above in connection with the first example.

In the reactive monomer in the third example, in Formula (XII), $R^4$ represents an ether group, Y represents a group having a fluorene skeleton, and l=2. A group represented by Formula (XVI) may be mentioned as the fluorene skeleton-containing group.

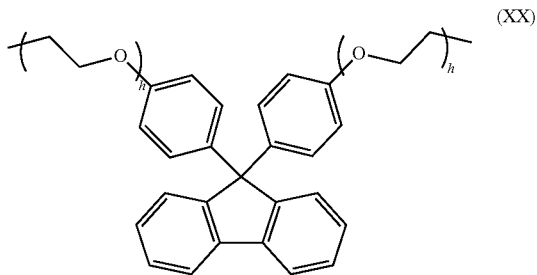
(XX)

In Formula (XVI), h is preferably 1 to 4, more preferably 1 or 2.

<Reactive Monomer in Which $R^4$ Represents NH Group>

In the reactive monomer in the first example, in Formula (XII), $R^4$ represents an NH group, Y represents a fluorine-containing group, and l=1. The same group as in the case where $R^4$ represents an ether group may be mentioned as the fluorine-containing group having one position which can be substituted. Specific examples of preferred fluorine-containing groups include aromatic groups such as $F(CF_2)_3CH_2$—, $F(CF_2)_6CH_2$—, $F(CF_2)_7CH_2$—, $F(CF_2)_8CH_2$—, and a residue of 2,6-difluoroaniline.

In the reactive monomer in the second example, in Formula (XII), $R^4$ represents an NH group, Y represents a saturated aliphatic group or aromatic group, and l=2. Saturated aliphatic groups include, for example, groups of straight-chain, branched-chain or cyclic carbon chains having two positions which can be substituted. Specific examples thereof include groups having an alkylene straight-chain structure such as ethylene, propylene, butylene, hexamethylene, and polyoxyalkylene, and groups having an alicyclic structure such as cyclohexyl and norbornane.

Aromatic groups include phenylene, xylylene, 4,4'-methylenebis(phenylamine), 2,3,5,6-tetrafluoro-phenyl, and 2,3,5,6-tetrafluoro-1,4-xylylenyl groups.

<Reactive Monomer in Which $R^4$ Represents Thioether Group>

The substituent Y in the case where $R^4$ represents a thioether group may be the same group as described above in connection with the case where $R^4$ represents an ether group or an NH group. Specific examples of the substituent Y include those obtained by adding an isocyanate group in the (meth)acryloyl group-containing isocyanate compound of Formula (I) to the following compound containing one or more mercapto group. Specific examples of compounds containing one or more mercapto groups include methyl mercaptan, ethyl mercaptan, propyl mercaptan, butyl mercaptan, amyl mercaptan, hexyl mercaptan, heptyl mercaptan, octyl mercaptan, nonyl mercaptan, cyclopentyl mercaptan, cyclohexyl mercaptan, furfuryl mercaptan, thiophenol, thiocresol, ethylthiophenol, benzyl mercaptan, 1,2-ethanedithiol, 1,2-propanedithiol, 1,3-propanedithiol, 1,4-butanedithiol, 1,6-hexanedithiol, 1,2,3-propanetrithiol, 1,1-cyclohexanedithiol, 1,2-cyclohexanedithiol, bicyclo[2,2,1]hepta-exo-cis-2,3-dithiol, 1,1-bis(mercaptomethyl)cyclohexane, bis(2-mercaptoethyl)ether, ethyleneglycol bis(2-mercaptoacetate), ethyleneglycol bis(3-mercaptopropionate), trimethylolpropanebis(2-mercaptoacetate), trimethylolpropanebis(3-mercaptopropionate), pentaerythritol tetrakis(2-mercaptoacetate), pentaerythritol tetrakis(3-mercaptopropionate), 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(2-mercaptoethyl)benzene, 1,3-bis(2-mercaptoethyl)benzene, 1,4-bis(2-mercaptoethyl)benzene, 1,2-bis(2-mercaptoethyleneoxy)benzene, 1,3-bis(2-mercaptoethyleneoxy)benzene, 1,4-bis(2-mercaptoethyleneoxy)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(2-mercaptoethyl)benzene, 1,2,4-tris(2-mercaptoethyl)benzene, 1,3,5-tris(2-mercaptoethyl)benzene, 1,2,3-tris(2-mercaptoethyleneoxy)benzene, 1,2,4-tris(2-mercaptoethyleneoxy)benzene, 1,3,5-tris(2-mercaptoethyleneoxy)benzene, 1,2,3,4-tetramercaptobenzene, 1,2,3,5-tetramercaptobenzene, 1,2,4,5-tetramercaptobenzene, 1,2,3,4-tetrakis(mercaptomethyl)benzene, 1,2,3,5-tetrakis(mercaptomethyl)benzene, 1,2,4,5-tetrakis(mercaptomethyl)benzene, 1,2,3,4-tetrakis(2-mercaptoethyl)benzene, 1,2,3,5-tetrakis(2-mercaptoethyl)benzene, 1,2,4,5-tetrakis(2-mercaptoethyl)benzene, 1,2,3,4-tetrakis(2-mercaptoethyleneoxy)benzene, 1,2,3,5-tetrakis(2-mercaptoethyleneoxy)benzene, 1,2,4,5-tetrakis(2-mercaptoethyleneoxy)benzene, 2,2'-dimercaptobiphenyl, 4,4'-thiobis-benzenethiol, 4,4'-dimercaptobiphenyl, 4,4'-dimercaptobibenzyl, 2,5-toluenedithiol, 3,4-toluenedithiol, 1,4-naphthalenedithiol, 1,5-naphthalenedithiol, 2,6-naphthalenedithiol, 2,7-naphthalenedithiol, 2,4-dimethylbenzene-1,3-dithiol, 4,5-dimethylbenzene-1,3-dithiol, 9,10-anthracenedimethanethiol, 1,3-bis(2-mercaptoethylthio)benzene, 1,4-bis(2-mercaptoethylthio)benzene, 1,2-bis(2-mercaptoethylthiomethyl)benzene, 1,3-bis(2-mercaptoethylthiomethyl)benzene, 1,4-bis(2-mercaptoethylthiomethyl)benzene, 1,2,3-tris(2-mercaptoethylthio)benzene, 1,2,4-tris(2-mercaptoethylthio)benzene, 1,3,5-tris(2-mercaptoethylthio)benzene, 1,2,3,4-tetrakis(2-mercaptoethylthio)benzene, 1,2,3,5-tetrakis(2-mercaptoethylthio)benzene, 1,2,4,5-tetrakis(2-mercaptoethylthio)benzene, bis(2-mercaptoethyl)sulfide, bis(2-mercaptoethylthio)methane, 1,2-bis(2-mercaptoethylthio)ethane, 1,3-bis(2-mercaptoethylthio)propane, 1,2,3-tris(2-mercaptoethylthio)propane, tetrakis(2-mercaptoethylthiomethyl)methane, 1,2-bis(2-mercaptoethylthio)propanethiol, 2,5-dimercapto-1,4-dithiane, bis(2-mercaptoethyl)disulfide, 3,4-thiophenedithiol, 1,2-bis(2-mercaptoethyl)thio-3-mercaptopropane, and bis-(2-mercaptoethylthio-3-mercaptopropane)sulfide. Among them, octyl mercaptan, 1,6-hexanedithiol, 2-mercaptoethyl sulfide, and 1,4-dimercaptobenzene are preferred.

(v) Production Process of Reactive Monomer

The reactive monomer of Formula (XII) may be prepared by reacting the (meth)acryloyl group-containing aromatic isocyanate compound of Formula (I) which contains two polymerizable functional groups, with the compound containing a functional group with active hydrogen such as hydroxyl, amino or mercapto group. The reaction method is not particularly limited, and, for example, mere mixing can produce the reactive monomer of Formula (XII).

As an example of the production of the compound having Formula (XII), the (meth)acryloyl group-containing aromatic isocyanate compound may be reacted with the hydroxyl group-containing compound in a solvent, in which case a urethanization catalyst is generally used. The use of the urethanization catalyst can significantly accelerate the reaction.

Examples of the urethanization catalysts include dibutyltin dilaurate, copper naphthenate, cobalt naphthenate and zinc naphthenate. However, because these catalysts contain heavy metals, the use thereof should be limited to as little as possible in view of the environment.

The reactivity of the aromatic isocyanate in the urethanization is greatly affected by the electron-withdrawing properties or substituent constant of the substituent group on the aromatic ring.

The substituent constant is a parameter defined based on the Hammett equation which quantifies the reactivity of the substituent group with active hydrogen on the aromatic ring. It is defined that when the substituent group is a hydrogen atom, the substituent constant is 0. Generally, it is accepted that the substituent constant of an electron-donating group is negative and that of an electron-withdrawing group is positive, and that the effect thereof is higher as the absolute value is larger.

In the aromatic isocyanate of Formula (I), the substituent group desirably has higher electron-withdrawing properties in view of enhancing the reactivity of the isocyanate group, and the substituent constant is desirably positive in view of accelerating the reaction.

For example, unsubstituted phenyl isocyanate or p-methylphenyl isocyanate tends to show drastically lower reactivity of the isocyanate group than that of the aromatic isocyanate of Formula (I).

The substituent constant of unsubstituted phenyl isocyanate is 0 as described above, and that of p-methylphenyl isocyanate is −0.17. Neither of the substituent constants is a positive value, and neither of the substituent groups is an electron-donating group. These will support the fact that the reactivity of the isocyanate groups of the two compounds is lower than that of the isocyanate monomer of Formula (I).

Meanwhile, the compound represented by Formula (I) has sufficient reactivity to the hydroxyl group, and the reaction for the production of the reactive monomer can be completed without a catalyst. The reaction temperature is preferably in the range of 0 to 60° C., more preferably 25 to 40° C. Any reaction temperature below 0° C. is unfavorable because the reaction will not complete and the materials will remain unreacted. Any reaction temperature exceeding 60° C. is also unfavorable because it can result in by-reaction or coloration.

The production process described above can simplify the reaction composition, eliminates the use of heavy metals to reduce the environmental load, and is thus very useful in the industry.

It is known that the above reaction proceeds even in the case of groups other than the hydroxyl, amino, and mercapto groups. For example, since the isocyanate group can also be reacted with a carboxyl group or the like, the reactive ethylenically unsaturated group can be introduced by an addition reaction.

Therefore, the (meth)acryloyl group-containing aromatic isocyanate compound of Formula (I) may be used with an isocyanate compound containing one reactive ethylenically unsaturated group for a reaction with a hydroxyl-, amino-, or mercapto-containing compound. Specific examples of isocyanate compounds containing one reactive ethylenically unsaturated group include 2-methacryloyloxyethylisocyanate, 2-acryloyloxyethylisocyanate, 2-(2-ethylbutenoyloxy)-ethylisocyanate, 2-(2-propylbutenoyloxy)ethylisocyanate, methacryloyloxymethylisocyanate, acryloyloxymethyl-isocyanate, (2-ethylbutenoyloxy)methylisocyanate, (2-propylbutenoyloxy)methylisocyanate, 3-methacryloyloxy-propylisocyanate, 3-acryloyloxypropylisocyanate, 3-(2-ethylbutenoyloxy)propylisocyanate, 3-(2-propylbutenoyloxy)-propylisocyanate, 4-methacryloyloxybutylisocyanate, 4-acryloyloxybutylisocyanate, 4-(2-ethylbutenoyloxy)-butylisocyanate, and 4-(2-propylbutenoyloxy)butylisocyanate.

(vi) Curable Composition

The curable composition according to the present invention comprises the reactive monomer of Formula (XII) and a polymerization initiator. Photopolymerization initiators may be used as the polymerization initiator. The application of an actinic radiation such as ultraviolet light or visible light can induce a polymerization reaction of the reactive monomer to prepare a cured product. Specific examples of such photopolymerization initiators include 1-hydroxycyclohexyl phenyl ketone, 2,2'-dimethoxy-2-phenylacetophenone, xanthone, fluorene, fluorenone, benzaldehyde, anthraquinone, triphenyl amine, carbazole, 3-methylacetophenone, 4-chlorobenzophenone, 4,4'-dimethoxybenzophenone, 4,4'-diaminobenzophenone, Michler's ketone, benzoylpropyl ether, benzoin ethyl ether, benzyldimethylketal, 1-(4-isopropylphenyl)-2-hydroxy-2-methylpropan-1-one, 2-hydroxy-2-methyl-1-phenylpropan-1-one, thioxanthone, diethylthioxanthone, 2-isopropylthioxanthone, 2-chlorothioxanthone, 2-methyl-1-[4-(methylthio)phenyl]-2-morpholinopropan-1-one, 2,4,6-trimethylbenzoyldiphenylphosphine oxide, 2-benzyl-2-dimethylamino-1-(4-morpholinophenyl)butan-1-one, and 1-[4-(2-hydroxyethoxy)-phenyl]-2-hydroxy-2-methylpropan-1-one.

Among them, 2,4,6-trimethylbenzoyldiphenylphosphine oxide and 1-hydroxycyclohexyl phenyl ketone are preferred.

These photopolymerization initiators may be used either solely or in a combination of two or more of them.

Further, the application of heat can induce a polymerization reaction of the reactive monomer to prepare a cured product. Specifically, a heat curable composition can be produced by adding a thermal polymerization initiator to a reactive monomer. Examples of such thermal polymerization initiators include diacyl peroxides, ketone peroxides, hydroperoxides, dialkyl peroxides, peroxy esters, azo compounds, and persulfates. They may be used either solely or in a combination of two or more of them.

The amount of the polymerization initiator used is preferably 0.1 to 20 parts by weight, more preferably 0.5 to 10 parts by weight, based on 100 parts by weight of the reactive monomer. When the amount of the polymerization initiator used is less than 0.1 part by weight, in some cases, the rate of polymerization of the reactive monomer is lowered. Further, in this case, the reactive monomer is sometimes likely to undergo inhibition of polymerization by oxygen or the like. On the other hand, when the amount of the polymerization initiator used exceeds 20 parts by weight, the polymerization reaction is suppressed, often resulting in lowered strength, adhesive strength and heat resistance of the cured film. Further, this is causative of coloring.

The curable composition according to the present invention may contain a reactive monomer other than the reactive monomer of Formula (XII). The incorporation of this reactive monomer can modify the viscosity of the composition and, at the same time, can regulate properties of the cured product, for example, mechanical properties such as reactivity, hardness, elasticity, and adhesion, and optical properties such as transparency.

Specific examples of such reactive monomers include ethylenically unsaturated aromatic compounds such as styrene, α-methylstyrene, o-methylstyrene, m-methylstyrene, p-methylstyrene, p-tert-butylstyrene, diisopropenylbenzene, o-chlorostyrene, m-chlorostyrene, p-chlorostyrene, 1,1-diphenylethylene, p-methoxystyrene, N,N-dimethyl-p-aminostyrene, N,N-diethyl-p-aminostyrene, ethylenically unsaturated pyridine, and ethylenically unsaturated imidazole;

carboxyl group-containing compounds such as (meth)acrylic acid, crotonic acid, maleic acid, fumaric acid, and itaconic acid;

alkyl (meth)acrylates such as methyl (meth)acrylate, ethyl (meth)acrylate, propyl (meth)acrylate, isopropyl (meth)acrylate, butyl (meth)acrylate, isobutyl (meth)acrylate, tert-butyl (meth)acrylate, pentyl (meth)acrylate, amyl (meth)acrylate, isoamyl (meth)acrylate, hexyl (meth)acrylate, heptyl (meth)acrylate, octyl (meth)acrylate, isooctyl (meth)acrylate, 2-ethylhexyl (meth)acrylate, nonyl (meth)acrylate, decyl (meth)acrylate, isodecyl (meth)acrylate, undecyl (meth)acrylate, dodecyl (meth)acrylate, lauryl (meth)acrylate, stearyl (meth)acrylate, and isostearyl (meth)acrylate;

fluoroalkyl (meth)acrylates such as trifluoroethyl (meth)acrylate, tetrafluoropropyl (meth)acrylate, hexafluoroisopropyl (meth)acrylate, octafluoropentyl (meth)acrylate, and heptadecafluorodecyl (meth)acrylate;

hydroxyalkyl (meth)acrylates such as hydroxyethyl (meth)acrylate, hydroxypropyl (meth)acrylate, and hydroxybutyl (meth)acrylate;

phenoxyalkyl (meth)acrylates such as phenoxyethyl (meth)acrylate, and 2-hydroxy-3-phenoxypropyl (meth)acrylate;

alkoxyalkyl (meth)acrylates such as methoxyethyl meth)acrylate, ethoxyethyl (meth)acrylate, propoxyethyl (meth)acrylate, butoxyethyl (meth)acrylate, and methoxybutyl (meth)acrylate;

polyethylene glycol (meth)acrylates such as polyethylene glycol mono(meth)acrylate, ethoxydiethylene glycol (meth)acrylate, methoxypolyethylene glycol (meth)acrylate, phenoxypolyethylene glycol (meth)acrylate, and nonylphenoxypolyethylene glycol (meth)acrylate;

polypropylene glycol (meth)acrylates such as polypropylene glycol mono(meth)acrylate, methoxypolypropylene glycol (meth)acrylate, ethoxypolypropylene glycol (meth)acrylate, and nonylphenoxypolypropylene glycol (meth)acrylate;

cycloalkyl (meth)acrylates such as cyclohexyl (meth)acrylate, 4-butylcyclohexyl (meth)acrylate, dicyclopentanyl (meth)acrylate, dicyclopentenyl (meth)acrylate, dicyclopentadienyl (meth)acrylate, bornyl (meth)acrylate, isobornyl (meth)acrylate, and tricyclodecanyl (meth)acrylate; and benzyl (meth)acrylate, tetrahydrofurfuryl (meth)acrylate, ethylene glycol di(meth)acrylate, diethylene glycol di(meth)acrylate, triethylene glycol di(meth)acrylate, polyethylene glycol di(meth)acrylate, propylene glycol di(meth)acrylate, dipropylene glycol di(meth)acrylate, tripropylene glycol di(meth)acrylate, polypropylene glycol di(meth)acrylate, neopentyl glycol di(meth)acrylate, 1,3-propanediol di(meth)acrylate, 1,4-butanediol di(meth)acrylate, 1,6-hexanediol di(meth)acrylate, hydroxy pivalic acid ester neopentyl glycol di(meth)acrylate, bisphenol A di(meth)acrylate, trimethylolpropane tri(meth)acrylate, pentaerythritol tri(meth)acrylate, trimethylolpropane trioxyethyl (meth)acrylate, tris(2-hydroxyethyl)isocyanurate tri(meth)acrylate, and dipentaerythritol hexa(meth)acrylate. These reactive monomers may be used either solely or in a combination of two or more of them.

In the production of the curable composition according to the present invention, mixing and regulation may be carried out by mixing the reactive monomer of Formula (XII) with the polymerization initiator at room temperature or with heating in a mixing machine such as a mixer, a ball mill or triple roll, or by adding and dissolving a reactive monomer, a solvent or the like as a diluent in the reaction system. Specific examples of reactive monomers usable as the diluent include the above-described reactive monomers. Specific examples of solvents include esters such as ethyl acetate, butyl acetate and isopropyl acetate; ketones such as acetone, methyl ethyl ketone, methyl isobutyl ketone and cyclohexanone; cyclic ethers such as tetrahydrofuran and dioxane; amides such as N,N-dimethylformamide; aromatic hydrocarbons such as toluene; and halogenated hydrocarbons such as methylene chloride.

The curable composition according to the present invention can be cured, for example, by coating a curable composition onto a base material to form a coating film and then applying a radiation or heat to the coating film. Both the radiation and heat may also be simultaneously applied for curing purposes.

The thickness of the coating film is preferably 1 to 200 μm for evaluation purposes but may be properly determined depending upon applications.

Coating methods usable herein include, for example, coating by a die coater, a spin coater, a spray coater, a curtain coater, or a roll coater, coating by screen printing, or coating by dipping.

An electron beam or light in the wavelength range of ultraviolet light to infrared light is preferred as the radiation for curing. For example, use may be made of ultrahigh pressure mercury light sources or metal halide light sources for ultraviolet light; metal halide light sources or halogen light sources for visual light sources; and halogen light sources for infrared light. In addition to the above light sources, light sources such as laser or LEDs may be used. The dose of the radiation may be properly determined depending upon the type of the light source, the thickness of the coating film and the like.

The curable composition according to the present invention can be used in applications such as resists (for example, solder resists, etching resists, color filter resists, and spacers), sealing (for example, waterproof sealing), paints (for example, antifouling paints, fluoropaints, and water-based paints), pressure-sensitive adhesives and adhesives (for example, adhesives and dicing tapes), printing plates (for example, CTP plates and offset plates), printing proofreading (for example, colorproof), lenses (for example, contact lenses, microlenses, and optical waveguides), dental materials, surface treatment (for example, optical fiber coating and disk coating), and battery materials (for example, solid electrolytes).

(vii) Reactive (meth)acrylate Polymer (A)

The reactive (meth)acrylate polymer (A) according to the present invention is a compound produced by reacting an isocyanate compound represented by Formula (I) with a polymer compound that includes repeating units containing a functional group with active hydrogen.

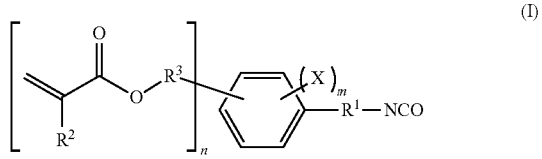

wherein $R^1$ is a single bond or a linear or branched alkylene group of 1 to 5 carbon atoms, $R^2$ is a hydrogen atom or a methyl group, $R^3$ is a single bond or a linear or branched alkylene group of 1 to 3 carbon atoms, X is independently a halogen atom or an electron-withdrawing group, m is an integer ranging from 0 to 4, n is an integer ranging from 1 to 3, and $1 \leq m+n \leq 5$.

Preferred examples of the isocyanate compounds include compounds represented by Formulae (III) and (IV).

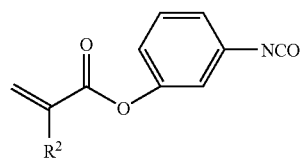

wherein $R^2$ is a hydrogen atom or a methyl group;

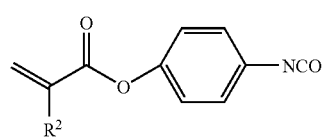

wherein $R^2$ is a hydrogen atom or a methyl group.

Here the polymer compound which is reacted with the isocyanate compound of Formula (I) includes repeating units containing a functional group with active hydrogen, such as a hydroxyl, amino, or mercapto group. The hydroxyl, amino, or mercapto group is reacted with the isocyanate group in the isocyanate compound of Formula (I) to form a urethane, urea, or thiourethane bond.

The repeating units containing a functional group with active hydrogen refer to repeating units based on a monomer(s) containing this functional group or capable of forming the functional group through a polymerization reaction. The above polymer compound is obtained by polymerizing the monomer(s). The polymer compound may be a homopolymer prepared from an identical type of monomer or a copolymer prepared from mutually different monomers.

The above polymer compound is preferably a polyhydroxy compound comprising repeating units.

The number average molecular weight (a value determined in terms of polystyrene by gel permeation chromatography (parts by mass; PC)) of the reactive (meth)acrylate polymer (A) according to the present invention is generally 500 to 100,000, preferably 8,000 to 40,000.

(viii) Production Process of Reactive (meth)acrylate Polymer (A)

The reactive (meth)acrylate polymer (A) is prepared by reacting the isocyanate compound of Formula (I) with a polymer compound that includes repeating units containing a functional group with active hydrogen. The reaction method is not particularly limited, and, for example, the reactive (meth)acrylate polymer (A) may be prepared by merely mixing these compounds together.

As an example of the production of the (meth)acrylate polymer (A), the (meth)acryloyl group-containing aromatic isocyanate compound may be reacted with the hydroxyl group-containing compound in a solvent, in which case a urethanization catalyst is generally used. The use of the urethanization catalyst can significantly accelerate the reaction.

Examples of the urethanization catalysts include dibutyltin dilaurate, copper naphthenate, cobalt naphthenate and zinc naphthenate. However, because these catalysts contain heavy metals, the use thereof should be limited to as little as possible in view of the environment.

The reactivity of the aromatic isocyanate in the urethanization is greatly affected by the electron-withdrawing properties or substituent constant of the substituent group on the aromatic ring. The substituent constant is a parameter defined based on the Hammett equation which quantifies the reactivity of the substituent group with active hydrogen on the aromatic ring. Generally, it is accepted that the substituent constant of an electron-donating group is negative and that of an electron-withdrawing group is positive, and that the effect thereof is higher as the absolute value is larger.

In the aromatic isocyanate of Formula (I) according to the invention, the substituent group desirably has higher electron-withdrawing properties in view of enhancing the reactivity of the isocyanate group, and the substituent constant is desirably positive in view of accelerating the reaction.

For example, unsubstituted phenyl isocyanate or p-methylphenyl isocyanate tends to show drastically lower reactivity of the isocyanate group than that of the aromatic isocyanate of Formula (I).

With the substituent constant of unsubstituted phenyl isocyanate being 0, that of p-methylphenyl isocyanate is −0.17. This will support the fact as described above.

Meanwhile, the compound represented by Formula (I) has sufficient reactivity to the hydroxyl group, and the reaction for the production of the reactive (meth)acrylate polymer can be completed without a catalyst. The reaction temperature is in the range of 0 to 60° C., preferably 25 to 40° C. Any reaction temperature below 0° C. is unfavorable because the reaction will not complete and the materials will remain unreacted. Any reaction temperature exceeding 60° C. is also unfavorable because it can result in by-reaction or coloration.

(ix) Polyhydroxy Compound Comprising Repeating Units

Polyhydroxy compounds comprising repeating units usable in the present invention include polyester polyol compounds, polycarbonate polyol compounds, polyether polyol compounds, polyurethane polyol compounds, homo- or copolymers of hydroxyalkyl (meth)acrylate, or epoxy (meth) acrylate compounds.

(ix-a) Polyester Polyol Compound

The polyester polyol compound used in the present invention is a compound having two or more hydroxyl groups and one or more ester bonds per molecule, and specific examples thereof include polyester polyols prepared from polyhydric alcohols and esters of polybasic acids, and polylactonediols such as polycaprolactonediols and polybutyrolactonediols. Further, polyester polyol compounds which have been synthesized so that the carboxyl group remains unchanged may also be used.

(ix-b) Polycarbonate Polyol Compound

The polycarbonate polyol used in the present invention is a compound having two or more hydroxyl groups and one or more carbonate bonds per molecule. Among others, compounds represented by Formula (XXI) are preferred:

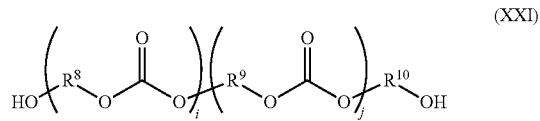

(XXI)

wherein $R^8$, $R^9$, and $R^{10}$ each independently represent a straight-chain, branched-chain or cyclic hydrocarbon group which may contain a hydroxyl group and/or a carboxyl group and have 2 to 30 carbon atoms; and i and j are each independently an integer of 0 to 100.

$R^8$, $R^9$, and $R^{10}$ preferably represent an alkylene group having 2 to 12 carbon atoms, and specific examples thereof include ethylene, trimethylene, tetramethylene, pentamethylene, hexamethylene, propylene, 2,2-dimethyl-1,3-propylen, 1,2-cyclohexylene, 1,3-cyclohexylene, and 1,4-cyclohexylene groups.

The polycarbonate polyol compound may be prepared, for example, by reacting a diaryl carbonate such as diphenyl carbonate with a polyol such as ethylene glycol, tetramethylene glycol, hexamethylene glycol, trimethylolethane, trimethylolpropane, glycerin, or sorbitol.

(ix-c) Polyether Polyol Compound

The polyether polyol compound used in the present invention is preferably a compound having a structure formed by dehydrocondensation of two or more alkylene glycols. This compound is produced, for example, by condensation of an alkylene glycol or ring-opening polymerization of an alkylene oxide.

Specific examples of alkylene glycols include ethylene glycol, propylene glycol, 1,4-butanediol, 1,3-butanediol, 1,5-pentanediol, neopentylglycol, 3-methyl-1,5-pentanediol, 1,6-hexanediol, and 1,4-cyclohexanedimethanol.

Specific examples of alkylene oxides include ethylene oxide, propylene oxide, tetrahydrofuran, styrene oxide, and phenyl glycidyl ether.

Specific examples of polyether polyol compounds include polyethylene glycol, polypropylene glycol, ethylene oxide/propylene oxide copolymer, polytetramethylene glycol, and polyhexamethylene glycol.

(ix-d) Polyurethane Polyol Compound

The polyurethane polyol compound used in the present invention has two or more hydroxyl groups and one or more urethane bonds per molecule. They may be produced by reacting a polyisocyanate with a polyol by any proper method. In this reaction, the isocyanate compound of Formula (I) may also be charged into the reaction system to produce the reactive (meth)acrylate polymer (A).

Specific examples of polyisocyanates include diisocyanates such as 2,4-toluene diisocyanate, 2,6-toluene diisocyanate, isophorone diisocyanate, hexamethylene diisocyanate, diphenylmethylene diisocyanate (o, m, or p)-xylene diisocyanate, methylenebis(cyclohexylisocyanate), trimethylhexamethylene diisocyanate, cyclohexane-1,3-dimethylene diisocyanate, cyclohexane-1,4-dimethylene diisocyanate, and 1,5-naphthalene diisocyanate. These polyisocyanates may be used either solely or in a combination of two or more of them.

Specific examples of polyols include ethylene glycol, propylene glycol, diol compounds such as 1,4-butanediol, 1,3-butanediol, 1,5-pentanediol, neopentylglycol, 3-methyl-1,5-pentanediol, 1,6-hexanediol, 1,4-cyclohexanedimethanol, glycerin, triol compounds such as trimethylol propane, pentaerythritol, dipentaerythritol, and diglycerin.

Polyol compounds usable herein include carboxyl-containing polyol compounds such as dihydroxy aliphatic carboxylic acids. These compounds are preferred because an alkali developing property can be imparted by introducing a carboxyl group into the reactive (meth)acrylate polymer (A).

Such carboxyl-containing polyol compounds include dimethylolpropionic acid and dimethylolbutanoic acid. They may be used either solely or in a combination of two or more of them.

Polyester polyol compounds in the above (ix-a), polycarbonate polyol compounds in the above (ix-b), and polyether polyol compounds in the above (ix-c) may be used as the polyol.

(ix-e) Homo- or Copolymer of Hydroxyalkyl (meth)acrylate

The homo- or copolymer of the hydroxyalkyl(meth)acrylate used in the present invention is a polymer produced by homopolymerizing or copolymerizing one or more hydroxyalkyl (meth)acrylates by any proper method. Specific examples of hydroxyalkyl (meth)acrylates usable herein include 2-hydroxyethyl (meth)acrylate, hydroxypropyl (meth)acrylate, hydroxybutyl (meth)acrylate, glycerin mono (meth)acrylate, glycerin di(meth)acrylate, trimethylol propane mono(meth)acrylate, pentaerythritol mono(meth)acrylate, dipentaerythritol mono(meth)acrylate, ditrimethylol propane mono(meth)acrylate, trimethylolpropane-alkylene oxide adduct-mono(meth)acrylate, 2-hydroxy-3-phenoxypropylacrylate, polyethylene glycol (meth)acrylate, and 6-hydroxyhexanoyloxyethyl (meth)acrylate.

Among them, 2-hydroxyethyl (meth)acrylate, hydroxypropyl (meth)acrylate, and hydroxybutyl (meth)acrylate are preferred, and 2-hydroxyethyl (meth)acrylate is more preferred. These hydroxyl-containing (meth)acrylates may be used either solely or in a combination of two or more of them.

The constituent(s) other than the hydroxyalkyl (meth)acrylate constituting the copolymer is an unsaturated compound copolymerizable therewith, and specific examples thereof include alkyl (meth)acrylates such as methyl (meth)acrylate, ethyl (meth)acrylate, propyl (meth)acrylate, butyl (meth) acrylate, isobutyl (meth)acrylate, sec-butyl (meth)acrylate, tert-butyl (meth)acrylate, hexyl (meth)acrylate, octyl (meth) acrylate, isooctyl (meth)acrylate, 2-ethylhexyl (meth)acrylate, decyl (meth)acrylate, lauryl (meth)acrylate, and stearyl (meth)acrylate; alicyclic (meth)acrylates such as cyclohexyl (meth)acrylate, bornyl (meth)acrylate, isobornyl (meth)acrylate, dicyclopentenyl (meth)acrylate, and dicyclopentenyloxyethyl (meth)acrylate; aromatic (meth)acrylates such as benzyl (meth)acrylate, phenyl (meth)acrylate, phenyl carbitol (meth)acrylate, nonylphenyl (meth)acrylate, nonylphenyl carbitol (meth)acrylate, and nonylphenoxy (meth)acrylate; amino group-containing (meth)acrylates such as 2-dimethylaminoethyl (meth)acrylate, 2-diethylaminoethyl (meth)acrylate, and 2-tert-butylaminoethyl (meth)acrylate; phosphorus-containing methacrylates such as methacryloxy ethylphosphate, bis-methacryloxy ethylphosphate, and methacryloxy ethyl phenyl acid phosphate (phenyl P); glycidyl (meth)acrylates; allyl (meth)acrylates; and phenoxyethyl acrylates.

Other unsaturated compounds usable herein include carboxyl- or acid anhydride-containing unsaturated compounds such as (meth)acrylic acid, itaconic acid, maleic anhydride, itaconic anhydride, polycaprolactone (meth)acrylate, (meth)acryloyloxyethyl phthalate, and (meth)acryloyloxyethyl succinate.

The expression "(meth)acrylate" or the like as used herein refers to methacrylate and/or acrylate.

Further, N-vinyl compounds such as N-vinylpyrrolidone, N-vinylformamide, N-vinylacetamide, and vinyl aromatic compounds such as styrene and vinyltoluene are also preferred.

(ix-f) Epoxy (meth)acrylate Compound

The epoxy (meth)acrylate compound is a compound comprising an unsaturated monocarboxylic acid added to an epoxy group in an epoxy resin. In some cases, a polybasic acid anhydride is further reacted. Specific examples of epoxy resins usable herein include bisphenol A-type epoxy resins, bisphenol F-type epoxy resins, bisphenol S-type epoxy resins, novolac epoxy resins, (o-, m-, or p-)cresol novolac epoxy resins, phenol novolac epoxy resins, naphthol modified novolac epoxy resins, and halogenated phenol novolac epoxy resins.

Among them, carboxylic acid group-containing epoxy (meth)acrylate resins prepared using, as a starting material, novolac-type epoxy resins such as novolac epoxy resins, (o-, m-, or p-) cresol novolac epoxy resins, phenol novolac epoxy resins, naphthol modified novolac epoxy resins, and halogenated phenol novolac epoxy resins are preferred from the viewpoint of photosensitivity.

The number average molecular weight (a value determined in terms of polystyrene as determined by gel permeation chromatography (parts by mass; PC)) of the reactive (meth)acrylate polymer (A) according to the present invention is generally 500 to 100,000, preferably 8,000 to 40,000. When the number average molecular weight is less than 500, the film strength is significantly lowered. On the other hand, when the number average molecular weight exceeds 40,000, the developing property and flexibility are deteriorated.

When the reactive (meth)acrylate polymer (A) according to the present invention is used in the resist, the acid value is preferably 5 to 150 mgKOH/g, more preferably 30 to 120 mgKOH/g. When the acid value is less than 5 mgKOH/g, the alkali developing property is sometimes deteriorated. On the other hand, when the acid value exceeds 150 mgKOH/g, the alkali resistance, electrical characteristics and the like of the cured film are sometimes deteriorated.

For the carboxyl-containing compounds among the polyhydroxy compounds comprising repeating units, the isocyanate of Formula (I) is reacted with the carboxyl group under certain reaction conditions to form an amide bond. The compound of Formula (I) may also be added through this reaction.

Further, the isocyanate compound of Formula (I) may be used with an isocyanate compound containing one reactive ethylenically unsaturated group for a reaction with a hydroxyl- (or amino- or mercapto-)containing polymer compound. Specific examples of isocyanate compounds containing one reactive ethylenically unsaturated group include 2-methacryloyloxyethylisocyanate, 2-acryloyloxyethylisocyanate, 2-(2-ethylbutenoyloxy)-ethylisocianate, 2-(2-propylbutenoyloxy)ethylisocyanate, methacryloyloxymethylisocyanate, acryloyloxymethyl-isocyanate, (2-ethylbutenoyloxy)methylisocyanate, (2-propylbutenoyloxy)methylisocyanate, 3-methacryloyloxy-propylisocyanate, 3-acryloyloxypropylisocyanate, 3-(2-ethylbutenoyloxy)propylisocyanate, 3-(2-propylbutenoyloxy)-propylisocyanate, 4-methacryloyloxybutylisocyanate, 4-acryloyloxybutylisocyanate, 4-(2-ethylbutenoyloxy)-butylisocyanate, and 4-(2-propylbutenoyloxy)butylisocyanate.

(x) Curable Composition

The curable composition is prepared by incorporating other components in addition to the reactive (meth)acrylate polymer (A) according to the present invention. This curable composition can be used in applications such as resists (for example, solder resists, etching resists, color filter resists, and spacers), sealing (for example, waterproof sealing), paints (for example, antifouling paints, fluoropaints, and water-based paints), pressure-sensitive adhesives and adhesives (for example, adhesives and dicing tapes), printing plates (for example, CTP plates and offset plates), printing proofreading (for example, colorproof), lenses (for example, contact lenses, microlenses, and optical waveguides), dental materials, surface treatment (for example, optical fiber coating and disk coating), and battery materials (for example, solid electrolytes).

Specific examples of curable compositions suitable for color filters and curable compositions suitable for solder resists are as follows. The reactive (meth)acrylate polymer (A) which is particularly preferred for use in the curable composition is a urethane (meth)acrylate polymer prepared by reacting a polyhydroxy compound with an isocyanate compound of Formula (I).

(x-a) Curable Composition Suitable for Color Filter

This curable composition contains a reactive (meth)acrylate polymer (A), a pigment (B), a photopolymerization initiator (D), an ethylenically unsaturated monomer (F), and an organic solvent (G).

(x-a-a) Reactive (meth)acrylate Polymer (A)

The content of the reactive (meth)acrylate polymer (A) in the curable composition is generally not less than 10% by mass, preferably not less than 20% by mass, more preferably 30 to 90% by mass. The mass ratio of reactive (meth)acrylate polymer (A)/other curable component such as ethylenically unsaturated monomer (F) is preferably 30/70 to 90/10, more preferably 40/60 to 85/15, from the viewpoints of balance between strength and photosensitivity. When the mass ratio of the reactive (meth)acrylate polymer (A) is smaller than 30/70, the film strength is lowered. On the other hand, when the mass ratio of the reactive (meth)acrylate polymer (A) is larger than 90/10, the cure shrinkage is increased.

(x-a-b) Pigment (B)

Red, green, and blue pigments may be used as the pigment (B). Black pigments may be mentioned as pigments which exhibits the maximum level of radiation shielding. Such black pigments may be conventional black pigments, and specific examples thereof include carbon black, acetylene black, lamp black, carbon nanotubes, graphite, iron black, iron oxide black pigments, aniline black, cyanine black, and titanium black. Black-based pigments prepared by mixing three organic pigments of red, green, and blue together may also be used.

Among them, carbon black and titanium black are preferred. Carbon black is particularly preferred from the viewpoints of light shielding and image properties.

The carbon black may be commercially available one, and the particle diameter of the carbon black is preferably 5 to 200 nm, more preferably 10 to 100 nm, from the viewpoints of dispersibility and resolution. When the particle diameter is less than 5 nm, homogeneous dispersion is difficult. On the other hand, when the particle diameter exceeds 200 nm, the resolution is lowered.

Specific examples of carbon blacks include Special Black 550, Special Black 350, Special Black 250, Special Black 100, Special Black 4 manufactured by Degussa, MA 100, MA 220, MA 230 manufactured by Mitsubishi Chemical Corporation, BLACKPEARLS 480 manufactured by Cabot Corporation, and RAVEN 410, RAVEN 420, RAVEN 450, and RAVEN 500 manufactured by Columbian Carbon.

(x-a-c) Photopolymerization Initiator (D)

The photopolymerization initiator (D) is a compound that, upon excitation by an actinic radiation, generates radicals which induce polymerization of the ethylenically unsaturated bond. Such photopolymerization initiators are required to generate radicals under high light shielding conditions. Therefore, high-sensitivity photopolymerization initiators are preferred. Specific examples of photopolymerization initiators include hexaarylbiimidazole compounds, triazine compounds, aminoacetophenone compounds, a combination of a sensitizing dye with an organic boron salt compound, titanocene compounds, and oxadiazole compounds.

Among them, hexaarylbiimidazole compounds, triazine compounds, aminoacetophenone compounds, glyoxy ester compounds, bisacylphosphine oxide compounds, and combinations thereof are preferred.

Specific examples of hexaarylbiimidazole compounds include 2,2'-bis(o-chlorophenyl)-4,4',5,5'-tetraphenyl-1,2'-biimidazole, 2,2'-bis(o-bromophenyl)-4,4',5,5'-tetraphenyl-1,2'-biimidazole, 2,2'-bis(o-chlorophenyl)-4,4',5,5'-tetra(o,p-dichlorophenyl)-1,2'-biimidazole, 2,2'-bis(o,p-dichlorophenyl)-4,4',5,5'-tetra(o,p-dichlorophenyl)-1,2'-biimidazole, 2,2'-bis(o-chlorophenyl)-4,4',5,5'-tetra(m-methoxyphenyl)-1,2'-biimidazole, and 2,2'-bis(o-methylphenyl)-4,4',5,5'-tetraphenyl-1,2'-biimidazole.

In order to further enhance the sensitivity, for example, benzophenone compounds such as benzophenone, 2,4,6-trimethylbenzophenone, 4-phenylbenzophenone, 4,4'-bis(dimethylamino)benzophenone, and 4,4'-bis(diethylamino) benzophenone, and thioxanthone compounds such as 2,4-diethylthioxanthone, isopropylthioxanthone, 2,4-diisopropylthioxanthone, and 2-chlorothioxanthone may be added as sensitizers.

Specific examples of triazine compounds include 2,4,6-tris(trichloromethyl)-s-triazine, 2,4,6-tris(tribromomethyl)-s-triazine, 2-propionyl-4,6-bis(trichloromethyl)-s-triazine, 2-benzoyl-4,6-bis(trichloromethyl)-s-triazine, 2-(4-chorophenyl)-4,6-bis(trichloromethyl)-s-triazine, 2,4-bis(4-methoxyphenyl)-6-trichloromethyl-s-triazine, 2-(4-methoxyphenyl)-2,6-bis(trichloromethyl)-s-triazine, 2-(4-methoxystyryl)-4,6-bis(trichloromethyl)-s-triazine, 2-(4-chlorostyryl)-4,6-bis(trichloromethyl)-s-triazine, 2-(4-aminophenyl)-4,6-bis(trichloromethyl)-s-triazine, 2,4-bis(3-chlorophenyl)-6-trichloromethyl-s-triazine, and 2-(4-aminostyryl)-4,6-bis(dichloromethyl)-s-triazine.

Specific examples of aminoacetophenone compounds include 2-methyl-1-[4-(methylthio)phenyl]-2-morpholino-propan-1-one, and 2-benzyl-2-dimethylamino-1-(4-morpholinophenyl)-butanone-1.

Specific examples of benzophenone compounds include benzophenone, 4-methylbenzophenone, 2,4,6-trimethylbenzophenone, benzoylbenzoic acid, 4-phenylbenzophenone, 3,3'-dimethyl-4-methoxybenzophenone, 4-benzoyl-4'-methyldiphenylsulfide, 4,4'-bis(dimethylamino)benzophenone, 4,4'-bis(diethylamino)benzophenone, (2-acryloyloxyethyl) (4-benzoylbenzyl)dimethylammoniumbromide, de, 4-(3-dimethylamino-2-hydroxypropoxy)-benzophenonemethochloride monohydrate, and (4-benzoylbenzyl)trimethylammoniumchloride.

Specific examples of thioxanthone compounds include thioxanthone, 2,4-diethylthioxanthone, isopropylthioxanthone, 2,4-diisopropylthioxanthone, 2-chlorothioxanthone, 1-chloro-4-propoxythioxanthone, and 2-(3-dimethylamimo-2-hydroxypropoxy)-3,4-dimethyl-9H-thioxanthen-9-one methochloride.

Specific examples of quinone compounds include 2-ethylanthraquinone and 9,10-phenanthrenequinone.

Specific examples of titanocene compounds include those described, for example, in Japanese Patent Laid-Open Nos. 152396/1984, 151197/1986, 10602/1988, 41484/1988, 291/1990, 12403/1991, 20293/1991, 27393/1991, 52050/1991, 221958/1992, and 21975/1992. Specific examples thereof include dicyclopentadienyl-Ti-dichloride, dicyclopentadienyl-Ti-diphenyl, dicyclopentadienyl-Ti-bis(2,3,4,5,6-pentafluorophenyl), dicyclopentadienyl-Ti-bis(2,3,5,6-tetrafluorophenyl), dicyclopentadienyl-Ti-bis(2,4,6-trifluorophenyl), dicyclopentadienyl-Ti-bis(2,6-difluorophenyl), dicyclopentadienyl-Ti-bis(2,4-difluorophenyl), bis(methylcyclopentadienyl)-Ti-bis(2,3,4,5,6-pentafluorophenyl), bis(methylcyclopentadienyl)-Ti-bis(2,3,5,6-tetrafluorophenyl), and bis(methylcyclopentadienyl)-Ti-bis(2,6-difluorophenyl).

Specific examples of oxadiazole compounds include halomethyl-containing 2-phenyl-5-trichloromethyl-1,3,4-oxadiazole, 2-(p-methylphenyl)-5-trichloromethyl-1,3,4-oxadiazole, 2-(p-methoxyphenyl)-5-trichloromethyl-1,3,4-oxadiazole, 2-styryl-5-trichloromethyl-1,3,4-oxadiazole, 2-(p-methoxystyryl)-5-trichloromethyl-1,3,4-oxadiazole, and 2-(p-butoxystyryl)-5-trichloromethyl-1,3,4-oxadiazole.

Specific examples of glyoxy ester compounds include benzyldimethylketal, benzoinethyl ether, and benzoin isopropyl ether.

Specific examples of bisacylphosphine oxide compounds include bis(2,6-dimethoxybenzoyl)-2,4,4-trimethylpentyl phosphineoxide, bis(2,6-dichlorobenzoyl)-phenylphosphineoxide, bis(2,6-dichlorobenzoyl)-2,5-dimethylphenylphosphineoxide, and bis(2,4,6-trimethylbenzoyl)phenylphosphineoxide.

(x-a-d) Ethylenically Unsaturated Monomer (F)

The ethylenically unsaturated monomer (F) is a compound that causes crosslinking by radicals generated from the photopolymerization initiator (D) upon exposure to an actinic radiation and functions, for example, to modify the viscosity of the composition. Specifically, (meth)acrylic esters are preferred.

Specific examples of (meth)acrylic esters include alkyl (meth)acrylates such as methyl (meth)acrylate, ethyl (meth)acrylate, propyl (meth)acrylate, butyl (meth)acrylate, isobutyl (meth)acrylate, sec-butyl (meth)acrylate, tert-butyl (meth)acrylate, hexyl (meth)acrylate, octyl (meth)acrylate, isooctyl (meth)acrylate, 2-ethylhexyl (meth)acrylate, decyl (meth)acrylate, lauryl (meth)acrylate, and stearyl (meth) acrylate;

alicyclic (meth)acrylates such as cyclohexyl (meth)acrylate, bornyl (meth)acrylate, isobornyl (meth)acrylate, dicyclopentenyl (meth)acrylate, and dicyclopentenyloxyethyl (meth)acrylate;

aromatic (meth)acrylates such as benzyl (meth)acrylate, phenyl (meth)acrylate, phenylcarbitol (meth)acrylate, nonylphenyl (meth)acrylate, nonylphenylcarbitol (meth)acrylate, and nonylphenoxy (meth)acrylate;

hydroxyl group-containing (meth)acrylates such as 2-hydroxyethyl (meth)acrylate, hydroxypropyl (meth)acrylate, hydroxybutyl (meth)acrylate, butanediol mono(meth)acrylate, glycerol (meth)acrylate, phenoxyhydroxypropyl (meth)acrylate, polyethylene glycol (meth)acrylate, and glycerol di(meth)acrylate;

amino group-containing (meth)acrylates such as 2-dimethylaminoethyl (meth)acrylate, 2-diethylaminoethyl (meth)acrylate, and 2-tert-butylaminoethyl (meth)acrylate;

phosphorus atom-containing methacrylates such as methacryloxyethyl phosphate, bis-methacryloxyethyl phosphate, and methacryloxyethylphenyl acid phosphate (phenyl-P);

diacrylates such as ethylene grycol di(meth)acrylate, diethylene grycol di(meth)acrylate, triethylene grycol di(meth)acrylate, tetraethylene di(meth)acrylate, polyethylene glycol di(meth)acrylate, propylene glycol di(meth)acrylate, dipropylene glycol di(meth)acrylate, tripropylene glycol di(meth)acrylate, 1,4-butanediol di(meth)acrylate, 1,3-butanediol di(meth)acrylate, neopentyl glycol di(meth)acrylate, 1,6-hexanediol di(meth)acrylate, and bis-glycidyl (meth)acrylate;

polyacrylates such as trimethylolpropane tri(meth)acrylate, pentaerythritol tri(meth)acrylate, and dipentaerythritol hexa(meth)acrylate;

modified polyol polyacrylates such as ethylene oxide (4 mol)-modified diacrylate of bisphenol S, ethylene oxide (4 mol)-modified diacrylate of bisphenol A, fatty acid-modified pentaerythritol diacrylate, propylene oxide (3 mol)-modified triacrylate of trimethylolpropane, and propylene oxide (6 mol)-modified triacrylate of trimethylolpropane;

polyacrylates having an isocyanuric acid skeleton, such as bis(acryloyloxyethyl)monohydroxyethyl isocyanurate, tris(acryloyloxyethyl) isocyanurate, and ε-caprolactone-modified tris(acryloylokyethyl) isocyanurate;

polyester acrylates such as α,ω-diacryloyl-(bisethylene glycol)-phthalate, or α,ω-tetraacryloyl-(bistrimethylolpropane)-tetrahydrophthalate; glycidyl (meth)acrylate;

allyl (meth)acrylate; ω-hydroxyhexanoyloxyethyl (meth)acrylate; polycaprolactone (meth)acrylate; (meth)acryloyloxyethyl phthalate; (meth)acryloyloxyethyl succinate; 2-hydroxy-3-phenoxypropyl acrylate; and phenoxyethyl acrylate.

Further, for example, N-vinyl compounds such as N-vinyl pyrrolidone, N-vinylformamide, or N-vinylacetamide, and polyester acrylate, urethane acrylate or epoxy acrylate may also be used as the ethylenically unsaturated monomer (F).

Among these compounds, hydroxyl-containing (meth)acrylate, glycidyl (meth)acrylate, and urethane acrylate are preferred. From the viewpoint of increased curability and heat resistance, the above compounds containing three or more ethylenically unsaturated groups are preferred.

(x-a-e) Organic Solvent (G)

Specific examples of the organic solvent (G) include ethers such as diisopropyl ether, ethyl isobutyl ether, and butyl ether; esters such as ethyl acetate, isopropyl acetate, butyl acetate (n, sec, tert), amyl acetate, 3-ethoxy ethyl propionate, 3-methoxy methyl propionate, 3-methoxy ethyl propionate, 3-methoxy propyl propionate, and 3-methoxy butyl propionate; ketones such as methyl ethyl ketone, isobutyl ketone, diisopropyl ketone, ethylamyl ketone, methyl butyl ketone, methyl hexyl ketone, methyl isoamyl ketone, methyl isobutyl ketone, and cyclohexanone; and glycols such as ethylene glycol monomethyl ether, ethylene glycol monoethyl ether, ethylene glycol diethyl ether, ethylene glycol monomethyl ether acetate, ethylene glycol monoethyl ether acetate, diethylene glycol monoethyl ether acetate, propylene glycol mono-t-butyl ether, propylene glycol monomethyl ether, propylene glycol monoethyl ether, propylene glycol monomethyl ether acetate, propylene glycol monoethyl ether acetate, dipropylene glycol monoethyl ether, dipropylene glycol monomethyl ether, dipropylene glycol monomethyl ether acetate, dipropylene glycol monoethyl ether acetate, ethylene glycol monobutyl ether, and tripropylene glycol methyl ether; and mixtures of the above compounds.

The organic solvent (G) can dissolve or disperse other components and has a boiling point of preferably 100 to 200° C., more preferably 120 to 170° C. The amount of the organic solvent (G) used is such that the solid content of the curable composition is brought to 5 to 50% by mass, preferably 10 to 30% by mass.

(x-a-f) Polyfunctional Thiol (H)

The curable composition may contain a polyfunctional thiol (H). The polyfunctional thiol (H) is a compound containing two or more thiol groups, and specific examples thereof include hexanedithiol, decanedithiol, butanediol bisthiopropionate, butanediol bisthioglycolate, ethylene glycol bisthioglycolate, ethylene glycol bisthiopropionate, trimethylolpropane tristhioglycolate, trimethylolpropane tristhiopropionate, pentaerythritol tetrakisthioglycolate, pentaerythritol tetrakisthiopropionate, trimercaptopropionate tris(2-hydroxyethyl)isocyanurate, 1,4-dimethylmercaptobenzene, 2,4,6-trimercapto-s-triazine, and 2-(N,N-dibutylamino)-4,6-dimercapto-s-triazine.

(x-a-g) Content of Each Component

Preferably, in the curable composition, the components other than the organic solvent (G) have the following respective contents.

The content of the reactive (meth)acrylate polymer (A) is preferably 10 to 40% by mass, more preferably 15 to 35% by mass based on the total amount of the composition. When the content is less than 10% by mass, the film strength is sometimes lowered. On the other hand, when the content exceeds 40% by mass, in some cases, the optical density is unsatisfactory.

The content of the pigment (B) is preferably 25 to 60% by mass, more preferably 30 to 55% by mass, based on the total amount of the composition. When the content is less than 25% by mass, the optical density is sometimes unsatisfactory. On the other hand, when the content exceeds 60% by mass, in some cases, the film strength is lowered.

The content of the photopolymerization initiator (D) is preferably 2 to 25% by mass, more preferably 5 to 20% by mass, based on the total amount of the composition. When the content is less than 2% by mass, the photosensitivity is sometimes unsatisfactory. On the other hand, when the content exceeds 25% by mass, the photosensitivity is so high that the resolution is disadvantageously sometimes lowered.

The content of the ethylenically unsaturated monomer (F) is preferably 5 to 20% by mass, more preferably 8 to 18% by mass, based on the total amount of the composition. When the content is less than 5% by mass, the photosensitivity is sometimes unsatisfactory. On the other hand, when the content exceeds 20% by mass, in some cases, the optical density is unsatisfactory.

When the polyfunctional thiol (H) is added, the content of the photopolymerization initiator (D) is preferably 2 to 20% by mass, more preferably 3 to 15% by mass, based on the total amount of the composition. When the content is less than 2% by mass, the photosensitivity is sometimes unsatisfactory. On the other hand, when the content exceeds 20% by mass, in some cases, the photosensitivity is so high that the resolution is disadvantageously lowered. The content of the polyfunctional thiol (F) is preferably 2 to 20% by mass, more preferably 3 to 15% by mass, based on the total amount of the composition. When the content is less than 2% by mass, the effect of the polyfunctional thiol does not sometimes occur. On the other hand, when the content exceeds 20% by mass, in some cases, the photosensitivity is so high that the resolution is disadvantageously lowered.

In addition to the above components, for example, pigment dispersants, adhesion improvers, leveling agents, development improvers, antioxidants, and thermal polymerization inhibitors may be added to the curable composition. In particular, since what is important for quality stabilization is to finely disperse the coloring material and to stabilize the dispersion state, preferably, the pigment dispersant is incorporated according to need.

(x-a-h) Production Process of Curable Composition

The curable composition may be produced by mixing the components together by any proper method. The mixing may be carried by either a method in which the components are simultaneously mixed together or a method in which the components are successively mixed.

Mixing of all the formulating components together at a time followed by dispersion treatment leads to a fear of causing denaturation of highly reactive components due to heat generation during dispersion treatment. To avoid this unfavorable phenomenon, mixing is preferably carried out by a method in which the pigment (B) such as a black pigment, either together with the solvent (G) and the pigment dispersant, or together with a mixture of the solvent (G) and the pigment dispersant with the reactive (meth)acrylate polymer (A), is previously dispersed and the remaining components are then mixed.

The dispersion treatment may be carried out with a paint conditioner, a bead mill, a ball mill, a triple roll mill, a stone mill, a jet mill, a homogenizer or the like.

When the dispersion is carried out with a bead mill, glass beads or zirconia beads having a diameter of 0.1 to several millimeters are preferred. The dispersion is generally carried out at a temperature of 0 to 100° C., preferably room temperature to 80° C. A proper dispersion time is determined by taking into consideration, for example, the formulation of the colored composition (coloring materials, solvents, dispersant, and binder polymer), and apparatus size of the bead mill.

When the dispersion is carried out with a triple roll mill, the dispersion temperature is generally 0 to 60° C. When the frictional heat of the rolls is so large that the temperature exceeds 60° C., the inside of the roll is cooled with circulating water. The number of times of passage of the ink through the triple roll mill depends upon conditions such as linear velocity of rolls, pressure between rolls, and the viscosity of the materials and may be, for example, 2 to 10 times.

The composition prepared by the dispersion treatment is mixed with the remaining components by any proper method to produce the curable composition.

(x-a-i) Production Process of Color Filter

A color filter is produced by coating the curable composition onto a transparent substrate, drying the solvent in an oven or the like, then exposing and developing the dried coating to form a pattern, and then postbaking the patterned coating.

Specific examples of the transparent substrate include films or sheets of inorganic glasses such as quartz glass, borosilicate glass, and lime-soda glass with a silica-coated surface; thermoplastics, for example, polyesters such as polyethylene terephthalate, polyolefins such as polypropylene and polyethylene, polycarbonate, polymethylmethacrylate, and polysulfone; and thermosetting plastics such as epoxy polymers and polyester polymers. In order to improve properties such as surface adhesion, such transparent substrates may be previously subjected to corona discharge treatment, ozone treatment, and thin film treatment with silane coupling agents, urethane polymers or other various polymers.

The curable composition may be coated onto the transparent substrate with a coater such as a dip coater, a roll coater, a wire bar, a flow coater, a die coater, a spray coater, or a spin coater.

After coating, the coating may be dried by any proper method to remove the solvent. A drying device such as a hot plate, an IR oven, or a convection oven may be used for drying. The drying temperature is preferably 40 to 150° C., and the drying time is preferably 10 sec to 60 min. The solvent may be removed by drying in vacuum.

The exposure is carried out by placing a photomask on a sample and then exposing the dried coating image-wise through the photomask. Specific examples of light sources usable in the exposure include lamp light sources such as xenon lamps, high-pressure mercury lamps, ultrahigh-pressure mercury lamps, metal halide lamps, medium-pressure mercury lamps, and low-pressure mercury lamps, and laser beam sources such as argon ion lasers, YAG lasers, excimer lasers, and nitrogen lasers. When only irradiating light with a specific wavelength is used, an optical filter may be utilized.

The development treatment is carried out with a developing solution, and the resist is developed, for example, by a dipping, shower or paddle method. The developing solution may be a solvent that can dissolve the resist film in its unexposed areas, and specific examples thereof include organic solvents such as acetone, methylene chloride, trichlene, and cyclohexanone.

Further, an alkali developing solution may be used as the developing solution. Specific examples of such alkali developing solutions include aqueous solutions containing inorganic alkali chemicals such as sodium carbonate, potassium carbonate, sodium silicate, potassium silicate, sodium hydroxide, and potassium hydroxide, or organic alkali chemicals such as diethanolamine, triethanolamine, and tetraalkylammonium hydroxide. The alkali developing solution may if necessary contain, for example, surfactants, water soluble organic solvents, hydroxyl- or carboxyl-containing low-molecular compounds. In particular, a number of surfactants have the effect of improving developing properties, resolution, smudge and the like, and, thus, the addition of such surfactants is preferred.

Specific examples of surfactants usable for the developing solution include anionic surfactants containing sodium naphthalenesulfonate, sodium benzenesulfonate or other groups, nonionic surfactants containing polyalkyleneoxy groups, and cationic surfactants containing tetraalkylammonium groups.

The development treatment is generally carried out at a development temperature of 10 to 50° C., preferably 15 to 45° C., for example, by dip development, spray development, brush development, or ultrasonic development.

Postbaking is generally carried out with the same apparatus as drying for solvent removal at a temperature of 150 to 300° C. for 1 to 120 min. The film thickness of the matrix thus obtained is preferably 0.1 to 2 µm, more preferably 0.1 to 1.5 µm, still more preferably 0.1 to 1 µm. In order that the film functions as the matrix, the optical density in the above thickness range is preferably not less than 3.

In the black matrix pattern produced by the above method, in general, an opening having a size of about 20 to 200 μm is provided between patterns. In the post-process, pixels of R, G, and B are formed in this space. In general, the pixels are of three colors of R, G, and B and may be formed using a curable composition comprising a reactive (meth)acrylate polymer (A) and colored with the above pigment or dye in the same manner as in the formation of the black matrix.

(x-b) Curable Composition Suitable for Solder Resist

This curable composition comprises a reactive (meth)acrylate polymer (A), a thermosetting polymer (C), a photopolymerization initiator (D), an ethylenically unsaturated monomer (F), and a thermal polymerization catalyst (E).

(x-b-a) Heat-curable Polymer (C)

The heat-curable polymer (C) is incorporated as a thermosetting component in the composition. The heat-curable polymer (C) per se may be cured by heating, or alternatively may be thermally reacted with the carboxyl group in the reactive (meth)acrylate polymer (A).

Specific examples of the heat-curable polymer (C) include epoxy polymers; phenol polymers; silicone polymers; melamine derivatives such as hexamethoxymelamine, hexabutoxymelamine, and condensed hexamethoxymelamine; urea compounds such as dimethylolurea; bisphenol A compounds such as tetramthylol-bisphenol A; oxazoline compounds; and oxetane compounds. They may be used either alone or in a combination of two or more of them.

Among them, epoxy polymers are preferred. Specific examples of epoxy polymers include epoxy compounds containing two or more epoxy groups per molecule such as bisphenol A epoxy polymers, hydrogenated bisphenol A epoxy polymers, brominated bisphenol A epoxy polymers, bisphenol F epoxy polymers, novolak epoxy polymers, phenol novolak epoxy polymers, cresol novolak epoxy polymers, N-glycidyl epoxy polymers, bisphenol A novolak epoxy polymers, chelate epoxy polymers, glyoxal epoxy polymers, amino-containing epoxy polymers, rubber-modified epoxy polymers, dicyclopentadiene phenolic epoxy polymers, silicone-modified epoxy polymers, and ε-caprolactone-modified epoxy polymers; and bisphenol S epoxy polymers, diglycidyl phthalate polymers, heterocyclic epoxy polymers, bixylenol epoxy polymers, biphenyl epoxy polymers, and tetraglycidylxylenoylethane polymers.

In order to impart flame retardancy, use may be made of epoxy polymers in which a halogen such as chlorine or bromine, phosphorus or other atom has been introduced into the structure in such a bound state that is less likely to be decomposed by heat or water. These epoxy polymers may be used either solely or in a combination of two or more of them.

The content of the heat-curable polymer (C) is preferably 10 to 150 parts by mass, more preferably 10 to 50 parts by mass, based on 100 parts by mass in total of the photocurable components. When the content of the heat-curable polymer (C) is less than 10 parts by mass, soldering heat resistance of the cured film is sometimes unsatisfactory. On the other hand, when the content of the heat-curable polymer (C) exceeds 150 parts by mass, the shrinkage of the cured film is increased. In this case, when the cured film is used in an insulating protective film in an FPC substrate, the warpage is likely to be increased.

(x-b-b) Photopolymerization Initiator (D)

The same photopolymerization initiators as used in the curable composition suitable for color filters may be used as the photopolymerization initiator (D).

The content of the photopolymerization initiator (D) is preferably 0.1 to 20 parts by mass, more preferably 0.2 to 10 parts by mass, based on 100 parts by mass in total of the urethane (meth)acrylate polymer (A), the ethylenically unsaturated monomer (F), and the carboxyl-containing epoxy (meth)acrylate compound which is optionally incorporated. When the content of the photopolymerization initiator (D) is less than 0.1 part by mass, in some cases, the curing of the composition is unsatisfactory.

(x-b-c) Thermal Polymerization Catalyst (E)

The thermal polymerization catalyst (E) functions to thermally cure the heat-curable polymer (C), and specific examples thereof include amines; amine salts or quaternary ammonium salts such as chlorides of the amines; acid anhydrides such as cyclic aliphatic acid anhydrides, aliphatic acid anhydrides, and aromatic acid anhydrides; nitrogen-containing heterocyclic compounds such as polyamides, imidazoles, and triazine compounds; and organometal compounds. They may be used either solely or in a combination of two or more of them.

Specific examples of amines include aliphatic or aromatic primary, secondary, and tertiary amines.

Specific examples of aliphatic amines include polymethylenediamine, polyetherdiamine, diethylenetriamine, triethylenetriamine, tetraethylenepentamine, triethylenetetramine, dimethylaminopropylamine, menthenediamine, aminoethylethanolamine, bis(hexamethylene)triamine, 1,3,6-trisaminomethylhexane, tributylamine, 1,4-diazabicyclo[2,2,2]octane, and 1,8-diazabicyclo[5,4,0]undecen-7-ene.

Specific examples of aromatic amines include metaphenylenediamine, diaminodiphenylmethane, and diaminodiphenylsulfone.

Specific examples of acid anhydrides include aromatic acid anhydrides such as phthalic anhydride, trimellitic anhydride, benzophenone tetracarboxylic acid anhydride, ethylene glycol bis(anhydro trimellitate), and glycerol tris(anhydro trimellitate), and maleic anhydride, succinic acid anhydride, methylnadic anhydride, hexahydrophthalic anhydride, tetrahydrophthalic anhydride, polyadipic acid anhydride, chlorendic anhydride, and tetrabromophthalic anhydride.

Specific examples of polyamides include primary amino- or secondary amino-containing polyaminoamides produced by condensing a dimeric acid with a polyamine such as diethylenetriamine or triethylenetetramine.

Specific examples of imidazoles include imidazole, 2-ethyl-4-methylimidazole, N-benzyl-2-methylimidazole, 1-cyanoethyl-2-undecylimidazolium-trimellitate, and 2-methylimidazolium-isocyamurate.

The triazine compound is a compound with a six-membered ring containing three nitrogen atoms, and specific examples thereof include melamine compounds such as melamine, N-ethylenemelamine, and N,N',N''-triphenylmelamine; cyanuric acid compounds such as cyanuric acid, isocyanuric acid, trimethyl cyanurate, isocyanurate, triethyl cyanurate, trisethyl isocyanurate, tri(n-propyl)cyanurate, tris(n-propyl)isocyanurate, diethyl cyanurate, N,N'-diethyl isocyanurate, methyl cyanurate, and methyl isocyanurate; and cyanuric acid melamine compounds such as a reaction product between equimolar amounts of a melamine compound and a cyanuric acid compound.

Specific examples of organometallic compounds include metal salts of organic acids such as dibutyltin dilaurate, dibutyltin maleate, and zinc 2-ethylhexanoate; 1,3-diketone metal complex salts such as nickel acetyl acetonate, zinc acetylacetonate; and metal alkoxides such as titanium tetrabutoxide, zirconium tetrabutoxide, and aluminum butoxide.

The amount of the thermal polymerization catalyst (E) used is preferably 0.5 to 20 parts by mass, more preferably 1 to 10 parts by mass, based on 100 parts by mass of the heat-curable polymer (C). When the amount of the thermal polymerization catalyst (E) used is less than 0.5 part by mass, the curing reaction does not proceed satisfactorily. In this case, in some cases, the heat resistance is deteriorated. Further, curing at an elevated temperature for a long period of time is necessary, and this is sometimes causative of lowered working efficiency. On the other hand, when the amount of the thermal polymerization catalyst (E) used exceeds 20 parts by mass, the thermal polymerization catalyst (E) is likely to react with the carboxyl group in the composition to cause gelation, often leading to a problem of deteriorated storage stability.

(x-b-d) Ethylenically Unsaturated Monomer (F)

The same ethylenically unsaturated monomer as used in the curable composition suitable for color filters may be used as the ethylenically unsaturated monomer (F).

The mixing ratio of the reactive (meth)acrylate polymer (A) to other ethylenically unsaturated monomer (F) is preferably 95:5 to 50:50, more preferably 90:10 to 60 to 40, still more preferably 85:15 to 70:30, in terms of mass ratio. When the mixing ratio of the reactive (meth)acrylate polymer (A) exceeds 95, the heat resistance of the cured film formed of the composition is sometimes deteriorated. On the other hand, when the mixing ratio of the reactive (meth)acrylate polymer (A) is less than 5, the solubility of the composition in alkali is likely to be lowered.

If necessary, carboxyl-containing epoxy (meth)acrylate compounds may be used as the curable component. Such carboxyl-containing epoxy (meth)acrylate compounds include, for example, those described in the above (ix-f). The acid value of these carboxyl-containing epoxy (meth)acrylate compounds is preferably not less than 10 mgKOH/g, more preferably 45 to 160 mgKOH/g, still more preferably 50 to 140 mgKOH/g. The use of the epoxy (meth)acrylate compounds having the above acid value can improve balance between the alkali solubility of the composition and the alkali resistance of the cured film. When the acid value is less than 10 mgKOH/g, the alkali solubility is deteriorated. On the other hand, when the acid value is excessively large, in some cases, for some formulation of the composition, the alkali resistance of the cured film and properties as a resist such as electrical characteristics are deteriorated. When the carboxyl-containing epoxy (meth)acrylate compound is used, preferably, this compound is used in an amount of not more than 100 parts by mass based on 100 parts by mass of the carboxyl-containing reactive (meth)acrylate polymer (A).

(x-b-e) Production Process of Curable Composition

As with the curable composition suitable for color filters, the above curable composition may be produced by mixing the above-described components together by a conventional method. The mixing method is not particularly limited, and examples thereof include a method in which a part of the components is mixed and the remaining components are then mixed and a method in which all the components are mixed at a time.

An organic solvent may be if necessary added to the composition for viscosity modification purposes or the like. The viscosity modification facilitates coating or printing onto an object, for example, by roller coating, spin coating, screen coating, or curtain coating. Organic solvents usable herein include ketone solvents such as ethyl methyl ketone, methyl isobutyl ketone, and cyclohexanone; ester solvents such as ethyl acetoacetate, γ-butyrolactone, and butyl acetate; alcohol solvents such as butanol and benzyl alcohol; cellosolve solvents and carbitol solvents such as carbitol acetate and methylcellosolve acetate, and their ester and ether derivative solvents; amide solvents such as N,N-dimethylformamide, N,N-dimethylacetamide, N,N-dimethylformamide, and N-methyl-2-pyrrolidone; dimethyl sulfoxide; phenol solvents such as phenol and cresol; nitro compound solvents; and aromatic or alicylic solvents of hydrocarbons such as toluene, xylene, hexamethylbenzene, cumene aromatic solvents, tetralin, decalin and dipentene. They may be used either solely or in a combination of two or more of them.

The amount of the organic solvent used is preferably such that the viscosity of the composition is 500 to 500,000 mPa·s, more preferably 1,000 to 500,000 mPa·s (as measured at 25° C. with Brookfield viscometer). When the viscosity of the composition is in the above-defined range, the composition is more suitable and easier to use for coating or printing on an object. The amount of the organic solvent used for bringing the viscosity to fall within the above-defined range is preferably not more than 1.5 times by mass the amount of the solid matter other than the organic solvent. When the amount of the organic solvent exceeds 1.5 times by mass, the solid content is lowered. In this case, when the composition is printed on a substrate or the like, a satisfactory film thickness cannot be provided by single printing and, thus, in some cases, printing should be carried out a plurality of times.

Further, a colorant may be added to the composition for use of the composition as ink. Specific examples of colorants usable herein include phthalocyanine blue, phthalocyanine green, iodine green, disazo yellow, crystal violet, titanium oxide, carbon black, and naphthalene black. Also when the composition is used as ink, the viscosity is preferably 500 to 500,000 mPa·s.

A flow modifier may be further added to the composition for flow modification purposes. The addition of the flow modifier can realize proper modification of the fluidity of the composition, for example, in the case where the composition is coated onto an object by roller coating, spin coating, screen coating, curtain coating or the like.

Specific examples of flow modifiers include inorganic or organic fillers, waxes, and surfactants. Specific examples of inorganic fillers include talc, barium sulfate, barium titanate, silica, alumina, clay, magnesium carbonate, calcium carbonate, aluminum hydroxide, and silicate compounds. Specific examples of organic fillers include silicone resins, silicone rubbers, and fluororesins. Specific examples of waxes include polyamide wax and polyethylene oxide wax. Specific examples of surfactants include silicone oils, higher fatty acid esters, and amides. These flow modifiers may be used either solely or in a combination of two or more.

If necessary, additives such as thermal polymerization inhibitors, thickeners, defoamers, leveling agents, and tackifiers can be added to the composition. Specific examples of thermal polymerization inhibitors include hydroquinone, hydroquinone monomethyl ether, tert-butyl catechol, pyrogallol, and phenothiazine. Specific examples of thickeners include asbestos, orben, bentone, and montmorillonite. The antifoamer is used to remove foam formed during printing, coating or curing, and specific examples thereof include surfactants such as acrylic and silicone surfactants. The leveling agent is used to render a film surface with concaves and convexes formed by printing or coating even, and specific examples thereof include surfactants such as acrylic and silicone surfactants. Specific examples of tackifiers include imidazole, thiazole, and triazole tackifiers and silane coupling agents.

Other additives usable herein include, for example, ultraviolet absorbers and plasticizers for storage stabilization purposes.

A coating film may be formed by coating the above curable composition onto a substrate or the like by screen printing to a suitable thickness and heat drying the coating. Thereafter, the coating film can be brought to a cured product by exposing and developing the coating film and heat curing the developed coating film.

The above curable composition can be used in various applications. In particular, the curable composition is excellent in photosensitivity and developing properties. Further, the curable composition can be cured to form a thin film which is also excellent in adhesion to substrate, insulating properties, heat resistance, warpage deformation, flexibility and appearance and thus is suitable for use as an insulating protective film in printed wiring boards. The insulating protective film may be formed by coating the composition or ink onto a substrate with a circuit formed thereon to a thickness of 10 to 100 μm and then heat treating the coating at a temperature of 60 to 100° C. for about 5 to 30 min to dry the coating and thus to bring the thickness to 5 to 70 μm. Next, the dried coating is exposed through a negative mask having a desired exposure pattern and is then developed with a developing solution to remove unexposed areas, followed by heat curing at a temperature of 100 to 180° C. for about 10 to 40 min.

This curable composition can be cured to form a cured product which is excellent particularly in flexibility. By virtue of excellent flexibility, the cured product is particularly suitable for use as an insulating protective film in an FPC substrate and can provide an FPC substrate which is less likely to curl and has good handleability. Further, the cured product may also be used as an insulating resin layer between layers, for example, in a multilayer printed wiring board.

Actinic light generated, for example, from conventional actinic light sources, for example, carbon arc, mercury vapor arc, and xenon arc may be used as an actinic light source used in the exposure.

Developing solutions usable herein include aqueous solutions of alkalis such as potassium hydroxide, sodium hydroxide, sodium carbonate, potassium carbonate, sodium phosphate, sodium silicate, ammonia, and amines.

Further, the curable composition may be used in a photosensitive layer in a dry film resist. The dry film resist comprises a photosensitive layer formed of the composition on a support formed of a polymer film or the like. The thickness of the photosensitive layer is preferably 10 to 70 μm. Specific examples of polymer films suitable as the support include films of polyester resins such as polyethylene terephthalate and aliphatic polyesters and polyolefin resins such as polypropylene and low-density polyethylene.

The dry film resist may be formed by coating the curable composition onto a support and then drying the coating to form a photosensitive layer. Further, a dry film resist, which comprises a support, a photosensitive layer, and a cover film stacked on top of one another, that is, which has films provided respectively on both sides of the photosensitive layer, may be formed by providing a cover film on the formed photosensitive layer. In use of the dry film resist, the cover film is peeled off. Until use of the dry film resist, the cover film provided on the photosensitive layer can protect the photosensitive layer, that is, the dry film resist has an excellent pot life.

In the formation of an insulating protective film on a printed wiring board using the dry film resist, the dry film resist is first laminated onto a substrate so that the photosensitive layer faces the substrate. Here when the dry film resist provided with the cover film is used, the cover film is removed to expose the photosensitive layer before contact with the substrate.

Next, the photosensitive layer and the substrate are thermocompression bonded to each other through a pressure roller or the like at about 40 to 120° C. to stack the photosensitive layer onto the substrate. Thereafter, the photosensitive layer is exposed through a negative mask having a desired exposure pattern, and the support is removed from the photosensitive layer. Development is carried out with a developing solution to remove the unexposed areas, and the photosensitive layer is then heat cured to prepare a printed wiring board comprising an insulating protective film provided on the surface of the substrate. Further, the above dry film resist may be used to form an insulating resin layer between layers in a multilayer printed wiring board.

EXAMPLES

The present invention will be described with reference to the following examples, but it should be construed that the invention is in no way limited to the examples. The examples employed the following analytical instruments and conditions.

<Gas Chromatography>
Chromatograph: GC14A manufactured by Shimadzu Corporation
Column: DB-1 (30 m×0.53 mm×1.5 μm) manufactured by J&W
Column temperature: Raised from 70° C. to 250° C. at 10° C./min and held at 250° C. for 18 min
Integrator: CR7A manufactured by Shimadzu Corporation
Injection temperature: 220° C.
Detector temperature: 270° C. FID
Detector: FID $H_2$ 40 ml/min Air 400 ml/min
Carrier gas: He 10 ml/min
<Automatic Titrator>
Titrator: COM-550 manufactured by Hiranuma Sangyo Co., Ltd.
<Infrared Spectroscopic Analysis>
Spectrometer: AVATAR 360 FT-IR manufactured by Thermo Nicolet Japan
Method: Reflection method
<Nuclear Magnetic Resonance>
Analytical instrument: JNM-AL400 manufactured by JEOL Example 1

[Step (1)]
A 300-ml four-necked flask equipped with a stirrer, a thermometer, a dropping funnel and a reflux condenser was charged with 10 g (0.09 mol) of 4-aminophenol (reagent manufactured by TOKYO KASEI KOGYO Co., Ltd.) and 100 ml of 1,4-dioxane as solvent in a nitrogen atmosphere. Subsequently, the temperature was raised to 50° C. and hydrogen chloride gas was fed at 100 ml/min for 1 hour.
[Step (2)]
The liquid obtained was heated to 55° C., and 27.1 g (0.27 mol) of carbonyl chloride was fed over a period of 6 hours. The temperature was maintained for another 3 hours. After the completion of the reaction, nitrogen was introduced to remove dissolved carbonyl chloride. A sample was obtained and analyzed by gas chromatography (hereinafter GC), which showed that 4-isocyanate phenol had been obtained in 90% yield.
[Step (3)]
To the liquid obtained, 100 ml of o-dichlorobenzene was added. Further, 31.0 g (0.25 mmol) of 3-chloropropionic acid chloride was added, followed by heating at 130° C. for 9 hours. During the reaction, 1,4-dioxane was distilled away from the system. The resultant reaction liquid was analyzed for alkali decomposable chlorine content by the following method.

Approximately 0.5 g of the sample was precisely weighed in a 300-ml stoppered conical flask, to which 100 ml of a methanol/purified water mixed liquid (70/30 by volume) and 10 ml of a 30% aqueous sodium hydroxide solution were added in sequence. A condenser tube was attached to the conical flask, and the mixture was heated under reflux for 1 hour in an 80° C. water bath and was cooled to room temperature. The resultant solution was transferred to a measuring flask, and purified water was added to make the volume 200 ml.

Exactly 10 ml of the resultant liquid was weighed in a 200-ml beaker, and 100 ml of purified water was added. Further, 1 ml of (1+1) nitric acid was added. The liquid obtained was potentiometrically titrated with one-fiftieth normal silver nitrate solution to determine the concentration of alkali decomposable chlorine from the following equation in which A was a titer (ml) of silver nitrate and B was a factor of the aqueous silver nitrate solution.

$$\text{Chlorine concentration (\%)} = A \times B \times 35.5/50 \times (\text{sample mass}) \times 100$$

Distilling away o-dichlorobenzene from the reaction liquid resulted in 29.2 g of the reaction liquid, of which the alkali decomposable chlorine concentration accounted for 4.1%. That is, the reaction liquid contained 1.20 g (0.03 mol) of alkali decomposable chlorine.

[Step (4)]

The reaction liquid and 90 ml of toluene were introduced into a 200-ml flask, to which 4.4 g (0.04 mol) of triethylamine was added dropwise over a period of 1 hour. Subsequently, the mixture was heated at 50° C. for 6 hours with stirring and was cooled to room temperature. The solid formed was filtered off and 95 g of a filtrate was obtained.

[Purification Step]

To the filtrate were added 0.02 g of phenothiazine (reagent manufactured by TOKYO KASEI KOGYO Co., Ltd.) and 0.02 g of 2,6-bis-t-butylhydroxytoluene (reagent manufactured by SIGMA-ALDRICH JAPAN). The pressure was then reduced to 10 kPa with a vacuum pump, and the solvent was distilled away. Thereafter, the concentrate obtained was introduced into a 100-ml flask and was distilled at a reduced pressure of 0.5 kPa to afford 5.0 g of a 100-110° C. fraction.

The fraction obtained was identified to be 4-acryloyloxyphenyl isocyanate by infrared spectroscopic analysis (hereinafter IR) and nuclear magnetic resonance (hereinafter NMR). The IR and NMR charts are given in FIGS. 1 and 2. The yield of 4-acryloyloxyphenyl isocyanate was 24%.

Example 2

[Step (1)]

A 300-ml four-necked flask equipped with a stirrer, a thermometer, a dropping funnel and a reflux condenser was charged with 15 g (0.14 mol) of 3-aminophenol (reagent manufactured by TOKYO KASEI KOGYO Co., Ltd.) and 100 ml of ethyl acetate in a nitrogen atmosphere. Subsequently, the temperature was raised to 50° C. and hydrogen chloride gas was fed at 100 ml/min for 1 hour.

[Step (2)]

The liquid obtained was heated to 55° C., and 40.6 g (0.41 mol) of carbonyl chloride was fed over a period of 6 hours, followed by heating at 60° C. for 3 hours. After the completion of the reaction, nitrogen was introduced to remove dissolved carbonyl chloride. A sample was obtained and analyzed by GC, which showed that 4-isocyanate phenol had been obtained in 90% yield.

[Step (3)]

To the reaction liquid obtained, 100 ml of o-dichlorobenzene was added. Further, 46.5 g (0.37 mmol) of 3-chloropropionic acid chloride was added, followed by heating at 130° C. for 1 hour. During the reaction, ethyl acetate was distilled away from the system. After the completion of the reaction, the reaction liquid was distilled at a reduced pressure of 0.5 kPa to recover a 100-110° C. fraction. Consequently, 25 g of 3-chloropropionyloxy-1-isocyanate-benzene was obtained.

The liquid obtained was analyzed for alkali decomposable chlorine content by the above method, resulting in 6.4% alkali decomposable chlorine concentration. That is, the liquid weighing 25 g contained 1.60 g (0.04 mol) of alkali decomposable chlorine.

[Step (4)]

25 Grams of the liquid was introduced into a 100-ml flask, and 50 g of toluene was further added, to which 5.1 g (0.05 mol) of triethylamine was added dropwise over a period of 1 hour. Subsequently, the mixture was heated at 50° C. for 6 hours with stirring and was cooled to room temperature. The solid formed was filtered off and 72.5 g of a filtrate was obtained.

[Purification Step]

To the filtrate were added 0.02 g of phenothiazine and 0.02 g of 2,6-bis-t-butylhydroxytoluene. The pressure was then reduced to 10 kPa with a vacuum pump, and the solvent was distilled away. Thereafter, the concentrate obtained was introduced into a 50-ml flask and was distilled at a reduced pressure of 0.5 kPa to afford 6.1 g of a 100-110° C. fraction.

The fraction obtained was identified to be 3-acryloyloxyphenyl isocyanate by IR and NMR. The IR and NMR charts are given in FIGS. 3 and 4. The yield of 3-acryloyloxyphenyl isocyanate was 23.9%.

Example 3

[Step (1')]

A 300-ml four-necked flask equipped with a stirrer, a thermometer, a dropping funnel and a reflux condenser was charged with 10 g (0.09 mol) of 4-aminophenol and 100 ml of 1,4-dioxane in a nitrogen atmosphere. Subsequently, the temperature was raised to 50° C. and hydrogen chloride gas was fed at 100 ml/min for 1 hour.

[Step (2')]

The liquid obtained was heated to 55° C., and 27.1 g (0.27 mol) of carbonyl chloride was fed over a period of 6 hours, followed by heating at 60° C. for 3 hours. After the completion of the reaction, nitrogen was introduced to remove dissolved carbonyl chloride. A sample was obtained and analyzed by GC, which showed that 4-isocyanate phenol had been obtained in 90% yield.

[Step (3')]

To the liquid obtained, 22.3 g (0.25 mmol) of methacrylic acid chloride (reagent manufactured by TOKYO KASEI KOGYO Co., Ltd.) was added, followed by heating at 110° C. for 6 hours. During the reaction, 1,4-dioxane was distilled away from the system.

[Purification Step]

To the reaction liquid were added 0.02 g of phenothiazine and 0.02 g of 2,6-bis-t-butylhydroxytoluene. The pressure was then reduced to 10 kPa with a vacuum pump, and the solvent was distilled away. Thereafter, the concentrate obtained was introduced into a 100-ml flask and was distilled at a reduced pressure of 0.5 kPa to afford 6.4 g of a 100-110° C. fraction. The fraction obtained was identified to be 4-methacryloyloxyphenyl isocyanate, and the yield was 31%.

Examples 4

[Step (1')]

A 500-ml four-necked flask equipped with a stirrer, a thermometer, a dropping funnel and a reflux condenser was charged with 30 g (0.275 mol) of 3-aminophenol (reagent manufactured by Mitsui Chemicals, Inc.) and 350 ml of 1,4-dioxane in a nitrogen atmosphere. Subsequently, the temperature was raised to 60° C. and hydrogen chloride gas was fed at 100 ml/min for 70 minutes.

[Step (2')]

The liquid obtained was heated to 60° C., and 54.0 g (0.54 mol) of carbonyl chloride was fed over a period of 5 hours. The temperature was maintained for another 3 hours. After the completion of the reaction, nitrogen was introduced to remove carbonyl chloride. A sample was obtained and analyzed by GC, which showed that 3-isocyanate phenol had been obtained in 90% yield.

absorption peak intensity of the isocyanate group around 2272 cm$^{-1}$ was determined, and the time to disappearance of the peak was measured. Measurement was carried out similarly for 3-methacryloyloxyphenyl isocyanate. The results are shown in Table 1.

Comparative Example 1

(2) Reactivity of Isocyanate Group of Phenyl Isocyanate

A reactor was charged with 0.477 g of phenyl isocyanate, 0.721 g of 2-propanol and 5 ml of toluene, followed by stirring in an oil bath at 60° C. A small portion was sampled every predetermined time period, and the samples were analyzed by IR using a NaCl plate. The absorption peak intensity of the isocyanate group around 2272 cm$^{-1}$ was determined, and an attempt was made to measure the time to complete disappearance of the peak. The results are shown in Table 1.

TABLE 1

| | Isocyanate | Reaction temperature (° C.) | NCO group content (mmol)) | OH group content (mmol) | NCO group disappearance time (min) |
|---|---|---|---|---|---|
| Ex. 5 | 4-methacryloyloxyphenyl isocyanate | 25 | 5 | 15 | 240 |
| Ex. 6 | 3-methacryloyloxyphenyl isocyanate | 25 | 5 | 15 | 180 |
| Comp. Ex. 1 | phenyl isocyanate | 25 | 5 | 15 | 450 (98%) |

[Step (3')]

To the liquid obtained, 300 ml of o-dichlorobenzene was added. Further, 200 g (1.91 mol) of methacrylic acid chloride and 1.0 g of phenothiazine were added, followed by heating at 110° C. for 48 hour2.

[Purification Step]

To the reaction liquid were added 1.0 g of phenothiazine and 0.5 g of 2,6-bis-t-butylhydroxytoluene. The pressure was then reduced to 10 kPa with a vacuum pump, and the solvent was distilled away. Thereafter, the concentrate obtained was introduced into a 100-ml flask and was distilled at a reduced pressure of 0.1 kPa to afford 13.8 g of a 123-125° C. fraction. The fraction obtained was identified to be 3-methacryloyloxyphenyl isocyanate, and the yield was 25%.

Examples 5 and 6

(1) Reactivity of Isocyanate Group of Compound Represented by Formula (I)

A reactor was charged with 0.613 g of 4-methacryloyloxyphenyl isocyanate, 0.721 g of 2-propanol and 5 ml of toluene, followed by stirring in an oil bath at 60° C. A small portion was sampled every predetermined time period, and the samples were analyzed by IR using a NaCl plate. The

Production Example 1

(1) Synthesis of Urethane (meth)acrylate (U-1)

A reaction vessel equipped with a stirrer, a thermometer and a condenser was charged with 3.66 g of polycarbonate diol (C3090 manufactured by KURARAY CO., LTD., average molecular weight: 3000) and 0.521 g of 4-methacryloyloxyphenyl isocyanate, and further with 10 ml of methylene chloride as a solvent, followed by stirring for 1 hour. Thereafter, 0.0174 g of dibutyltin dilaurate was added, and stirring was performed continuously. The reaction was completed when the absorption peak (2280 cm$^{-1}$) of the isocyanate group in the infrared absorption spectrum substantially disappeared. Consequently, a viscous liquid urethane (meth)acrylate (U-1) was obtained. A NMR chart of the urethane (meth)acrylate (U-1) is given in FIG. 5.

Comparative Production Example 1

(2) Synthesis of Urethane (meth)acrylate (U-2)

A reaction vessel equipped with a stirrer, a thermometer and a condenser was charged with 30.089 g of polycarbonate diol (C3090 manufactured by KURARAY CO., LTD., average molecular weight: 3000) and 3.149 g of 2-methacryloyloxyethyl isocyanate, and further with 100 ml of methylene chloride as a solvent, followed by stirring for 1 hour. Thereafter, 0.133 g of dibutyltin dilaurate was added, and stirring was performed continuously. The reaction was completed when the absorption peak (2280 cm$^{-1}$) of the isocyanate group in the infrared absorption spectrum substantially disappeared. Consequently, a viscous liquid urethane (meth)acrylate (U-2) was obtained. A NMR chart of the urethane (meth)acrylate (U-2) is given in FIG. 6.

Production Example 2

Synthesis of (meth)acrylic Copolymer (XVI)

A four-necked flask equipped with a dropping funnel, a thermometer, a condenser tube and a stirrer was charged with 9.917 g of hydroxyethyl acrylate, 48.533 g of butyl methacrylate, 0.133 g of mercapto ethanol and 62.97 g of propylene glycol monomethoxy acetate (hereinafter, PMA). The four-necked flask was then purged with nitrogen for 1 hour. After the temperature was raised to 90° C. in an oil bath, a liquid mixture of 0.84 g and 62.97 g of azobisisobutyronitrile and PMA, respectively, was added dropwise over a period of 1 hour. After polymerization was carried out for 3 hours, a liquid mixture of 0.27 g and 7.00 g of azobisisobutyronitrile and PMA, respectively, was added, the temperature was raised to 100° C. and polymerization was performed for 1.5 hours. The reaction liquid was cooled at room temperature, and a predetermined amount of the solvent was removed by evaporation at reduced pressure. The polymer component was separated in 1.5 L of methanol, and was purified in hexane to afford 55.29 g of a white (meth)acrylic copolymer (XVI). GPC provided that the mass-average molecular weight in terms of polystyrene was 25,000.

Production Example 3

(1) Synthesis of Reactive Acrylic Copolymer (P1-MPI)

A reaction vessel was charged with 0.215 g of 4-methacryloyloxyphenyl isocyanate, 1.454 g of (meth)acrylic copolymer (XVI), 0.0067 g of dibutyltin dilaurate and 5 ml of methylene chloride, followed by stirring. The reaction was completed when the absorption peak (2280 cm$^{-1}$) of the isocyanate group in the infrared absorption spectrum substantially disappeared. Consequently, a reactive acrylic copolymer (P1-MPI) was obtained. A NMR chart of the reactive acrylic copolymer (P1-MPI) is given in FIG. 7.

Comparative Production Example 2

(2) Synthesis of Reactive Acrylic Copolymer (P1-MOI)

A reaction vessel was charged with 0.180 g of 2-methacryloyloxyethyl isocyanate, 1.614 g of (meth)acrylic copolymer (XVI), 0.0067 g of dibutyltin dilaurate and 5 ml of methylene chloride, followed by stirring. The reaction was completed when the absorption peak (2280 cm$^{-1}$) of the isocyanate group in the infrared absorption spectrum substantially disappeared. Consequently, a reactive acrylic copolymer (P1-MOI) was obtained. A NMR chart of the reactive acrylic copolymer (P1-MOI) is given in FIG. 8.

Examples 7 to 12, and Comparative Examples 2 to 5

(1) Preparation of Curable Composition and Evaluation Sample

A reactive urethane compound as shown in Tables 2-1 and 2-2, a bisphenol A type diterminal bisacrylate monomer (BPE4-A manufactured by DAI-ICHI KOGYO SEIYAKU CO., LTD.) as a reactive monomer, in amounts shown in Tables 2-1 and 2-2, and 1-hydroxy-cyclohexyl-phenyl-ketone (IRGACURE 184 manufactured by Ciba Specialty Chemicals) as a photopolymerization initiator, in amounts shown in Tables 2-1 and 2-2, were added to 20 g of dichloromethane (product from JUNSEI CHEMICAL CO., LTD.). These were mixed together by stirring at room temperature to give a uniform solution of a curable composition. The resultant curable composition solution was applied to a glass plate (50 mm×50 mm) such that the dry thickness would be about 200 μm, and the solvent was dried at 50° C. for 30 minutes. Consequently, an evaluation sample was prepared.

The reactive urethane compound used in Example 12 was the urethane (meth)acrylate (U-1) obtained in Production Example 1, and the reactive urethane compounds used in Example 7 to 11 were prepared by altering raw materials and the like in Production Example 1. The reactive urethane compound used in Comparative Example 5 was the urethane (meth)acrylate (U-2) obtained in Comparative Production Example 1, and the reactive urethane compounds used in Comparative Example 2 to 4 were prepared by altering raw materials and the like in Comparative Production Example 1.

TABLE 2-1

| | Reactive urethane compound Type |
|---|---|
| Ex. 7 | 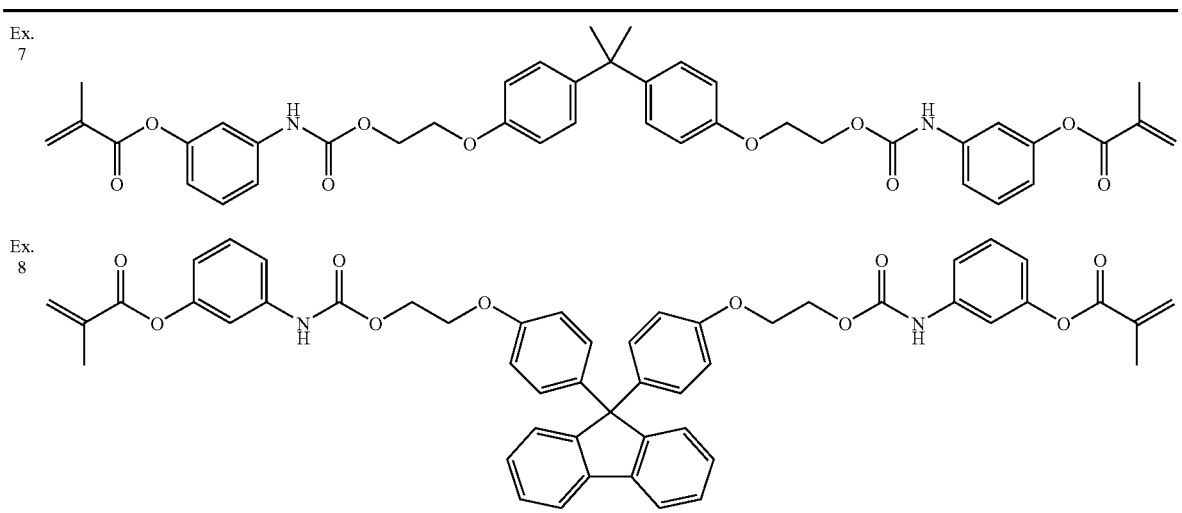 |
| Ex. 8 | |

TABLE 2-1-continued
Ex. 9
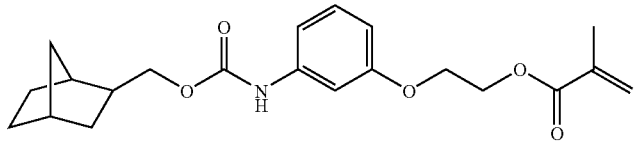
Ex. 10
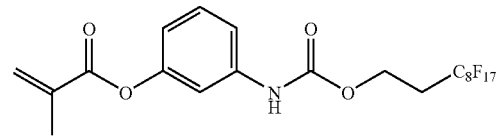
Ex. 11
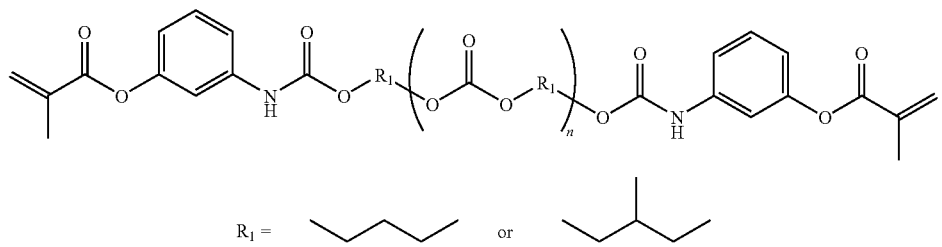
Ex. 12
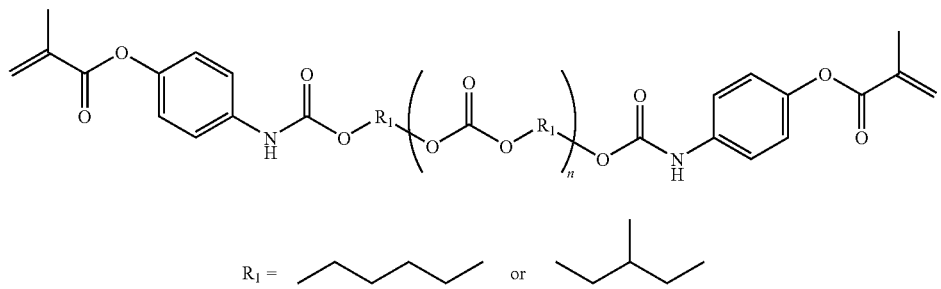
|  | Reactive urethane compound (g) | Reactive monomer (g) | Polymerization initiator (g) |
| --- | --- | --- | --- |
| Ex. 7 | 5 | 5 | 0.2 |
| Ex. 8 | 5 | 5 | 0.2 |
| Ex. 9 | 5 | 5 | 0.2 |
| Ex. 10 | 10 | — | 0.2 |
| Ex. 11 | 10 | — | 0.2 |
| Ex. 12 | 10 | — | 0.2 |
TABLE 2-2
Reactive urethane compound
Type
Comp. Ex. 2
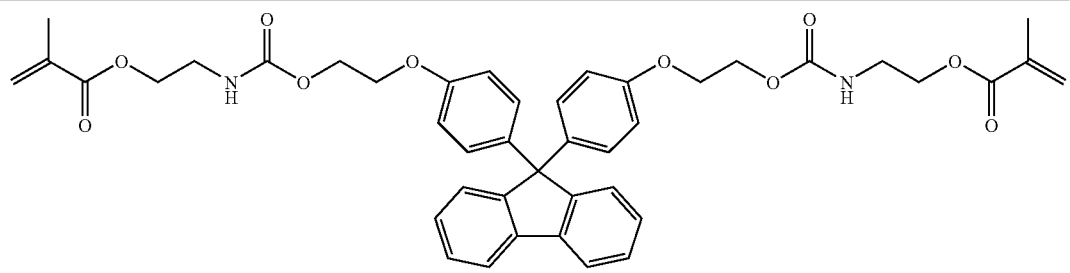

TABLE 2-2-continued

Comp. Ex. 3

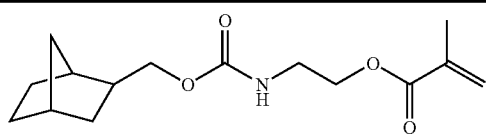

Comp. Ex. 4

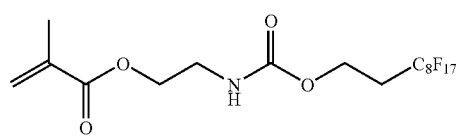

Comp. Ex. 5

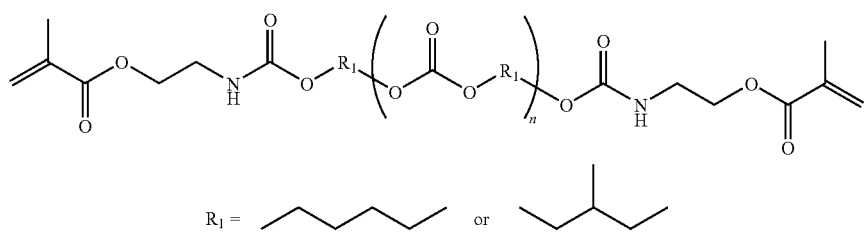

|  | Reactive urethane compound (g) | Reactive monomer (g) | Polymerization initiator (g) |
|---|---|---|---|
| Comp. Ex. 2 | 5 | 5 | 0.2 |
| Comp. Ex. 3 | 5 | 5 | 0.2 |
| Comp. Ex. 4 | 10 | — | 0.2 |
| Comp. Ex. 5 | 10 | — | 0.2 |

(2) Evaluation of Curable Composition of Reactive Monomer

<Curing Properties>

The evaluation sample obtained in (1) was exposed to light using an exposure apparatus fitted with an ultrahigh pressure mercury lamp (MULTI LIGHT ML-251A/B manufactured by USHIO INC), at 500 mJ/cm² such that the reaction would be in a steady state. During the exposure, a spectrum was obtained with an infrared spectrometer (FT/IR7000 manufactured by JASCO Corporation), and an absorption peak assigned to ethylenically unsaturated group was observed at 810 cm⁻¹. The change of absorption peak before and after the exposure was obtained to determine the reactivity of ethylenically unsaturated group (absorption peak intensity after exposure/absorption peak intensity before exposure×100 (%)). The results are shown in Table 3.

<Adhesive Strength>

The evaluation sample obtained in (1) was exposed to light at 3 J/cm² using the exposure apparatus fitted with an ultrahigh pressure mercury lamp. The surface of the cured sample film was polished with sand paper. Further, a holding tool in an adhesion tester (Elcometor manufactured by Elcometer Instrument Ltd) was cured with an epoxy adhesive (HC-1210 manufactured by Mitsui Chemicals Inc.), and the adhesive strength was measured with an adhesion tester. The results are shown in Table 3.

<Heat Resistance>

The evaluation sample obtained in (1) was exposed to light at 3 J/cm² using the exposure apparatus fitted with an ultrahigh pressure mercury lamp. The cured sample was measured for decomposition temperature using a differential scanning calorimeter (EXSTAR 6000 manufactured by Seiko instruments inc.) to evaluate the heat resistance. The results are shown in Table 3.

<Refractive Index>

The curable composition prepared in (1) was applied to a PET film such that the dry thickness would be about 200 μm, and solvent was dried at 50° C. for 30 minutes. The resultant evaluation sample was exposed at an exposure of 3 J/cm² using the exposure apparatus fitted with an ultrahigh pressure mercury lamp. The cured samples was peeled off as a film, and the refractive index of the cured films was measured with an Abbe's refractometer. The results are shown in Tables 3.

<Curing Shrinkage>

The curable composition prepared in (1) was applied to a PET film such that the dry thickness would be about 200 μm, and solvent was dried at 50° C. for 30 minutes. The thickness of the resultant evaluation sample was measured, and then was exposed at an exposure of 3 J/cm² using the exposure apparatus fitted with an ultrahigh pressure mercury lamp. The thickness of the cured sample was measured again, and the reduction of the thickness was obtained to determine the curing shrinkage. The results are shown in Tables 3.

TABLE 3

|  | Adhesive strength (N/mm²) | Curing shrinkage (%) | decomposition temperature (° C.) | Refractive index |
|---|---|---|---|---|
| Ex. 7 | 3.5 | 6.9 | >400 | 1.573 |
| Ex. 8 | 3.5 | 6.2 | >400 | 1.584 |
| Ex. 9 | 3.4 | 8.3 | 390 | 1.572 |
| Ex. 10 | 1.2 | 7.6 | 225 | 1.435 |
| Ex. 11 | 3.5 | 1.7 | 285 | 1.493 |
| Ex. 12 | 3.8 | 1.6 | 288 | 1.493 |
| Comp. Ex. 2 | 0.7 | 12.6 | 310 | 1.560 |
| Comp. Ex. 2 | 1.1 | 15.6 | 265 | 1.544 |
| Comp. Ex. 2 | 0.2 | 10.0 | 175 | 1.397 |
| Comp. Ex. 2 | 2.4 | 2.1 | 230 | 1.484 |

Examples 13 and 14, and Comparative Examples 6 and 7

(1) Preparation of Curable Composition and Evaluation Sample

A reactive polymer as shown in Table 4 and 1-hydroxy-cyclohexyl-phenyl-ketone (IRGACURE 184 manufactured by Ciba Specialty Chemicals) as a photopolymerization initiator, in amounts shown in Table 3, were added to 20 g of dichloromethane (product from JUNSEI CHEMICAL CO., LTD.). These were mixed together by stirring at room temperature to give a uniform solution of a curable composition. The resultant curable composition solution was applied to a glass plate (50 mm×50 mm) such that the dry thickness would be about 200 μm, and the solvent was dried at 50° C. for 30 minutes. Consequently, an evaluation sample was prepared.

The reactive polymer used in Example 14 was the reactive acrylic copolymer (P1-MPI) obtained in Production Example 3, and the reactive polymer used in Example 13 was prepared by altering raw materials and the like in Production Example 3. The reactive polymer used in Comparative Example 7 was the reactive acrylic copolymer (P1-MOI) obtained in Comparative Production Example 2, and the reactive polymer used in Comparative Example 6 was prepared by altering raw materials and the like in Comparative Production Example 2.

TABLE 4

| | Reactive urethane polymer | | Polymerization inhibitor |
|---|---|---|---|
| | Type | (g) | (g) |
| Ex. 13 | 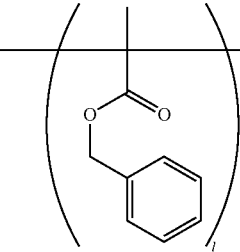 | 10 | 0.2 |
| | $R_2 =$ 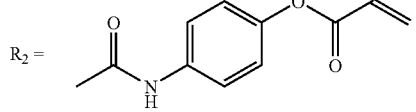 | | |
| Ex. 14 |  | 10 | 0.2 |

TABLE 4-continued

| | Reactive urethane polymer | | Polymerization inhibitor |
|---|---|---|---|
| | Type | (g) | (g) |
| Comp. Ex. 6 | 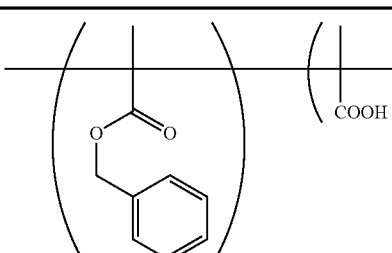 | 10 | 0.2 |
| Comp. Ex. 7 | 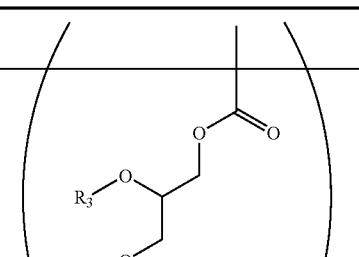 | 10 | 0.2 |

(2) Evaluation of Curable Composition of Reactive Polymer

<Heat Resistance>

The evaluation sample obtained in (1) was exposed to light at 3 J/cm² using the exposure apparatus fitted with an ultra-high pressure mercury lamp. The cured sample was measured for decomposition temperature using a differential scanning calorimeter (EXSTAR 6000 manufactured by Seiko instruments inc.) to evaluate the heat resistance. The results are shown in Table 5.

TABLE 5

| | Ex. 14 | Ex. 15 | Comp. Ex. 3 | Comp. Ex. 4 |
|---|---|---|---|---|
| Heat resistance (° C.) | 310 | 275 | 250 | 230 |

The invention claimed is:

1. A process for producing an aromatic isocyanate compound containing a (meth)acryloyl group, the compound being represented by Formula (I):

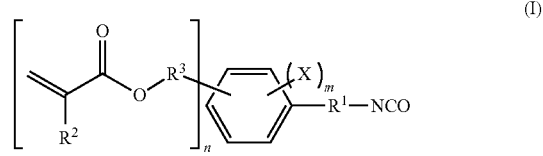

(I)

wherein $R^1$ is a single bond or a linear or branched alkylene group of 1 to 5 carbon atoms, $R^2$ is a hydrogen atom or a methyl group, $R^3$ is a single bond, X is independently a halogen atom or an electron-withdrawing group, m is an integer ranging from 0 to 4, n is an integer ranging from 1 to 3, and $1 \leq m+n \leq 5$, the process comprising the following steps (1') to (3'):

(1') a step of reacting a hydroxyphenylamine compound and a mineral acid to obtain a hydroxyphenylamino mineral acid salt compound, the hydroxyphenylamine compound being represented by Formula (V):

(V)

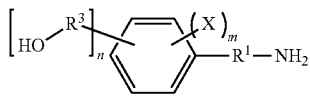

wherein $R^1$, $R^3$, X, m and n are as defined in Formula (I),
the hydroxyphenylamino mineral acid salt compound being represented by Formula (VI):

(VI)

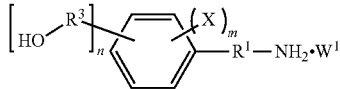

wherein $R^1$, $R^3$, X, m and n are as defined in Formula (I), and $W^1$ is the mineral acid;

(2') a step of reacting the hydroxyphenylamino mineral acid salt compound obtained in the step (1') and a compound represented by Formula (VII) to obtain a hydroxyphenyl isocyanate compound:

(VII)

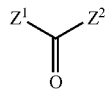

wherein $Z^1$ and $Z^2$ are each a fluorine atom, a chlorine atom, a bromine atom, an imidazole, a pyrazole or R'O— wherein R' is an alkyl or alkenyl group of 1 to 6 carbon atoms that is a straight chain or has a branch, or an aryl group that is unsubstituted or is substituted with a substituent group,
the hydroxyphenyl isocyanate compound being represented by Formula (VIII):

(VIII)

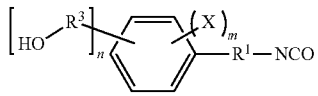

wherein $R^1$, $R^3$, X, m and n are as defined in Formula (I); and
(3') a step of reacting the hydroxyphenyl isocyanate compound obtained in the step (2') with a compound represented by Formula (XI):

(XI)

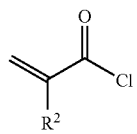

wherein $R^2$ is as defined in Formula (I).

2. The process for producing an aromatic isocyanate compound containing a (meth)acryloyl group according to claim 1, wherein the mineral acid is at least one acid selected from the group consisting of sulfuric acid, nitric acid, hydrochloric acid, carbonic acid and phosphoric acid.

3. The process for producing an aromatic isocyanate compound containing a (meth)acryloyl group according to claim 1, wherein the reactions in the steps (1') to (3') are performed in solvents.

4. The process for producing an aromatic isocyanate compound containing a (meth)acryloyl group according to claim 3, wherein the solvent used in the step (1') is at least one solvent selected from the group consisting of water, alcohols, esters, ethers, aromatic hydrocarbons, aliphatic hydrocarbons and halogenated hydrocarbons.

5. The process for producing an aromatic isocyanate compound containing a (meth)acryloyl group according to claim 3, wherein the solvent used in the steps (2') and (3') is at least one solvent selected from the group consisting of esters, ethers, aromatic hydrocarbons, aliphatic hydrocarbons and halogenated hydrocarbons.

6. The process for producing an aromatic isocyanate compound containing a (meth)acryloyl group according to claim 4, wherein the step (2') is performed after the solvent used in the step (1') is distilled away.

7. The process for producing an aromatic isocyanate compound containing a (meth)acryloyl group according to claim 1, wherein a basic nitrogen compound is added as catalyst in the step (3').

\* \* \* \* \*